(12) United States Patent
Liu et al.

(10) Patent No.: US 11,667,629 B2
(45) Date of Patent: Jun. 6, 2023

(54) ISOXAZOLE DERIVATIVE, PREPARATION METHOD THEREFOR, AND USE THEREOF

(71) Applicant: SICHUAN KELUN-BIOTECH BIOPHARMACEUTICAL CO., LTD., Chengdu (CN)

(72) Inventors: Jinming Liu, Chengdu (CN); Jiaqiang Cai, Chengdu (CN); Yongyong Wu, Chengdu (CN); Wei Yin, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 288 days.

(21) Appl. No.: 16/758,232

(22) PCT Filed: Dec. 7, 2018

(86) PCT No.: PCT/CN2018/119715
§ 371 (c)(1),
(2) Date: Apr. 22, 2020

(87) PCT Pub. No.: WO2019/120088
PCT Pub. Date: Jun. 27, 2019

(65) Prior Publication Data
US 2020/0339558 A1    Oct. 29, 2020

(30) Foreign Application Priority Data

Dec. 22, 2017  (CN) .......................... 201711402082.2
Jan. 16, 2018  (CN) .......................... 201810038649.0

(51) Int. Cl.
C07D 417/14    (2006.01)
C07D 451/02    (2006.01)
C07D 413/14    (2006.01)
B65D 85/00     (2006.01)

(52) U.S. Cl.
CPC .......... *C07D 417/14* (2013.01); *B65D 85/70* (2013.01); *C07D 413/14* (2013.01); *C07D 451/02* (2013.01)

(58) Field of Classification Search
CPC ... C07D 413/14; C07D 417/14; C07D 451/02
See application file for complete search history.

(56) References Cited

U.S. PATENT DOCUMENTS

2010/0152166 A1* 6/2010 Genin .................. C07D 413/12
                                                 546/202
2014/0039007 A1* 2/2014 Tully ..................... A61K 45/06
                                                 546/209

FOREIGN PATENT DOCUMENTS

| CN | 104045635 A   | 9/2014  |
|----|---------------|---------|
| EP | 2 128 158 A1  | 12/2009 |
| EP | 3 034 499 A1  | 6/2016  |
| JP | 2010-533722 A | 10/2010 |
| JP | 2014-500319 A | 1/2014  |
| JP | 2018-500305 A | 1/2018  |
| WO | 2009/012125 A1| 1/2009  |
| WO | 2009/149795 A2| 12/2009 |
| WO | 2012/087521 A1| 6/2012  |
| WO | 2012087519    | 6/2012  |
| WO | 2012087521    | 6/2012  |
| WO | 2016/096116 A1| 6/2016  |
| WO | 2016097933    | 6/2016  |
| WO | 2017145031    | 8/2017  |
| WO | 2017145040    | 8/2017  |

OTHER PUBLICATIONS

Stella (J. Pharmaceutical Sciences, 2010, 99(12), pp. 4755-4765).*
European Patent Office; Communication and Extended European Search Report; EP Application No. 18892613.3; dated May 7, 2021.
International Application No. PCT/CN2018/119715, International Search Report and Written Opinion dated Mar. 13, 2019, 8 pages.
CN Patent Office; Notice of the First Examination Opinion; CN Application No. 2018800687301; dated Jan. 20, 2023; 12 pgs.

* cited by examiner

*Primary Examiner* — Susanna Moore
(74) *Attorney, Agent, or Firm* — Kilpatrick Townsend & Stockton LLP

(57) ABSTRACT

The present invention generally relates to an isoxazole derivative, a preparation therefor, and a use thereof. In particular, the present invention provides a farnesoid X receptor (FXR) agonist compound, and a stereoisomer, a tautomer, a polymorph, a solvate (e.g., a hydrate), a pharmaceutically acceptable salt, an ester, a metabolite, and an N-oxide, and the chemically protected forms and prodrugs thereof. The present invention further provides a preparation method for the compound, an intermediate thereof, and a pharmaceutical composition and kit containing the same and used thereof for treating FXR-mediated diseases or conditions.

16 Claims, No Drawings

ISOXAZOLE DERIVATIVE, PREPARATION METHOD THEREFOR, AND USE THEREOF

CROSS-REFERENCE TO RELATED APPLICATIONS

This application is a National Phase Entry of PCT/CN2018/119715, filed Dec. 7, 2018, which claims the benefit of priority to CN Patent Application No. 201711402082.2, filed Dec. 22, 2017 and CN Patent Application No. 201810038649.0, filed on Jan. 16, 2018, the teachings of which are hereby incorporated by reference in their entireties for all purposes.

FIELD OF THE INVENTION

The present invention generally relates to a compound for use in the treatment of a disease or disorder mediated by the farnesoid X receptor (FXR), and more specifically relates to a compound as a FXR agonist, and a stereoisomer, tautomer, polymorph, solvate (e.g., hydrate), pharmaceutically acceptable salt, ester, metabolite, N-oxide thereof, as well as its chemically protected form or prodrug. The present invention further relates to a method for preparing the compound, an intermediate, a pharmaceutical composition and kit comprising the compound as well as the therapeutic use thereof.

BACKGROUND OF THE INVENTION

The farnesoid X receptor (FXR, NR1H4) is expressed in the liver, throughout the entire gastrointestinal tract including the esophagus, stomach, duodenum, small intestine and colon, kidney and adrenal gland (Kuipers, F. et al., The Farnesoid X Receptor (FXR) as Modulator of Bile Acid Metabolism, Rev. Endocrine Metab. Disorders, 2004, 5: 319-326). FXR is a member of the ligand-activated transcription factors known as nuclear receptors. Bile acids such as chenodeoxycholic acid (CDCA) or its taurine or glycine amide conjugate are endogenous ligands of FXR. FXR is activated upon binding with bile acids, and controls the expression of a variety of genes through a heterodimer complex with a retinoid X receptor (RXR), including the gene expressions involved in the homeostasis of bile acid, cholesterol, triglyceride and lipoprotein in the liver and circulatory system (Kalaany, N. Y.; Mangelsdorf, D. J.; LXRS and FXR: the yin and yang of cholesterol and fat metabolism, Annu. Rev. Physiol., 2006, 68, 159-191; Calkin, A. C.; Tontonoz, P.; Transcriptional integration of metabolism by the nuclear sterol-activated receptors LXR and FXR, Nat. Rev. Mol. Cell Biol., 2012, 13, 213-224). FXR also seems to be involved in paracrine and endocrine signaling by upregulating the expression of the cytokine Fibroblast Growth Factor 15 (rodents) or 19 (monkeys, humans) (T. Inagaki et al., Fibroblast growth factor 15 functions as an enterohepatic signal to regulate bile acid homeostasis. Cell Metab., 2005, 2 (4), 217-225).

Bile acids are amphipathic molecules that form micelles and emulsify dietary lipids. This property also makes bile acids cytotoxic if sufficient concentrations are achieved and thus mechanisms have evolved to ensure bile acid concentrations are tightly regulated. FXR plays a key role in regulating bile acid homeostasis (Makishima, M.; Nuclear Receptors as Targets for Drug Development: Regulation of Cholesterol and Bile Acid Metabolism by Nuclear Receptors, J. Pharmacol. Sci., 2005, 97: 177-183).

In addition, FXR has been shown to regulate complex biological processes beyond metabolism, such as liver regeneration or intestinal barrier integrity. FXR also controls the immune system of the intestine and liver, and has certain anti-inflammatory effects (Modica, S.; Gadaleta, R. M.; Moschetta, A.; Deciphering the nuclear bile acid receptor FXR paradigm, Nucl. Recept. Signal., 2010, 8, e005).

Obeticholic acid (6-Et CDCA) is a FXR receptor agonist that is more active than the endogenous ligand CDCA, and has been shown in a phase IIa clinical study of the non-alcoholic fatty liver disease (NAFLD) to achieve significant improvement in insulin sensitivity and other metabolic benefits (Mudaliar, S.; Henry, R. R.; Sanyal, A. J. et al., Efficacy and safety of the farnesoid X receptor agonist obeticholic acid in patients with type 2 diabetes and nonalcoholic fatty liver disease, Gastroenterology, 2013, 145, 574-582). A phase IIb study of obeticholic acid showed that 72-week treatment was also beneficial for the improvement of the histopathology of non-alcoholic steatohepatitis (NASH). In a primary biliary cirrhosis (PBC) phase III study, the liver function impairment in patients was ameliorated (Nevens, F., Andreone, P., Mazzella, G. et al., The first primary biliary cirrhosis (PBC) phase 3 trial in two decades—an international study of the FXR agonist obeticholic acid in PBC patients, J. Hepatol., 2014, 60, S525-S526).

WO2012087519 discloses an agonist or partial agonist of FXR for the treatment of a disorder mediated by FXR. However, the FXR agonist compounds disclosed in the prior art still have deficiencies in pharmacodynamic or pharmacokinetic properties.

SUMMARY OF THE INVENTION

The present invention generally relates to a compound of general formula (I), or a stereoisomer, tautomer, polymorph, solvate (e.g., hydrate), pharmaceutically acceptable salt, ester, metabolite, N-oxide thereof, its chemically protected form or prodrug,

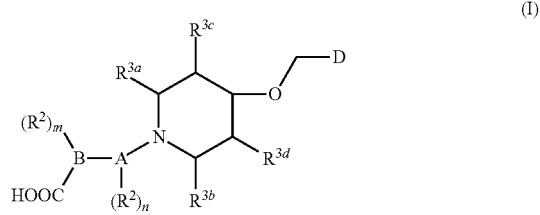

wherein:
A is selected from the group consisting of thiazolylene, phenylene and pyridylene;
B is selected from the group consisting of $C_{6-10}$ aryl and 5- to 10-membered heteroaryl containing 1, 2, 3 or 4 heteroatoms independently selected from the group consisting of N, O and S;
D is

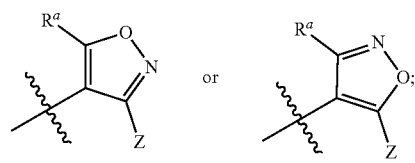

Z is

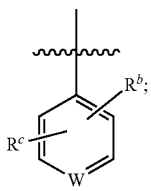

W is selected from the group consisting of N and $CR^d$, preferably is $CR^d$;

$R^a$ is selected from the group consisting of hydrogen, $C_{1-6}$ alkyl, $C_{2-6}$ alkenyl, $C_{2-6}$ alkynyl, $C_{3-8}$ cycloalkyl, 3- to 14-membered heterocyclyl, $C_{1-6}$ alkyl-O—, $C_{1-6}$ haloalkyl, $C_{3-8}$ halocycloalkyl and $C_{1-6}$ haloalkyl-O—;

$R^b$, $R^c$ and $R^d$ are each independently selected from the group consisting of hydrogen, halogen, hydroxyl, cyano, —$NH_2$, nitro, $C_{1-6}$ alkyl, $C_{1-6}$ haloalkyl, $C_{1-6}$ alkyl-O—, $C_{1-6}$ haloalkyl-O—, $C_{3-8}$ cycloalkyl, $C_{3-8}$ halocycloalkyl, $C_{3-8}$ cycloalkyl-O— and $C_{3-8}$ halocycloalkyl-O—;

$R^1$ and $R^2$ are each independently selected from the group consisting of hydrogen, halogen, cyano, hydroxyl, —$NH_2$, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl, $C_{3-8}$ halocycloalkyl, $C_{1-6}$ alkyl-NH— and $(C_{1-6}$ alkyl$)_2$-N—;

$R^{3a}$, $R^{3b}$, $R^{3c}$ and $R^{3d}$ are each independently selected from the group consisting of hydrogen, halogen, cyano, hydroxyl, —$NH_2$, oxo, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl and $C_{3-8}$ halocycloalkyl; alternatively, any two of $R^{3a}$, $R^{3b}$, $R^{3c}$ and $R^{3d}$ together form $C_{1-6}$ alkylene, preferably, any two of $R^{3a}$, $R^{3b}$, $R^{3c}$ and $R^{ad}$ together form $C_{2-6}$ alkylene, and more preferably, $R^{3a}$ and $R^{3b}$ together form $C_{2-6}$ alkylene;

m and n are each independently 0, 1, 2, 3 or 4, preferably 0, 1 or 2; and the above alkyl, alkylene, alkenyl, alkynyl, cycloalkyl, heterocyclyl, aryl and heteroaryl are each optionally substituted with 1, 2, or 3 substituents independently selected from the group consisting of halogen, hydroxyl, oxo, cyano, —$NH_2$, nitro, $C_{1-6}$ alkyl, $C_{1-6}$ haloalkyl, $C_{1-6}$ alkyl-O—, $C_{1-6}$ haloalkyl-O—, $C_{3-6}$ cycloalkyl, $C_{3-6}$ halocycloalkyl, $C_{1-6}$ alkyl-NH—, $(C_{1-6}$ alkyl$)_2$-N—, $C_{1-6}$ hydroxyalkyl, cyano-$C_{1-6}$ alkyl, 3- to 14-membered heterocyclyl, $C_{6-14}$ aryl and 5- to 14-membered heteroaryl.

Another aspect of the present invention is a pharmaceutical composition comprising the compound of general formula (I) or a stereoisomer, tautomer, polymorph, solvate (e.g., hydrate), pharmaceutically acceptable salt, ester, metabolite, N-oxide thereof, its chemically protected form or prodrug, and one or more pharmaceutically acceptable carriers. The pharmaceutical composition can further comprise one or more additional therapeutic agents suitable for the prophylaxis or treatment of a disease or disorder mediated by FXR.

The present invention further encompasses a method for the prophylaxis or treatment of a disease or disorder mediated by FXR, comprising administering to a subject in need thereof a therapeutically effective amount of the compound of general formula (I) or a stereoisomer, tautomer, polymorph, solvate (e.g., hydrate), pharmaceutically acceptable salt, ester, metabolite, N-oxide thereof, its chemically protected form or prodrug, or the pharmaceutical composition.

The present invention further encompasses a kit for the prophylaxis or treatment of a disease or disorder mediated by FXR, comprising:

a) a first container containing at least one compound of general formula (I) or a stereoisomer, tautomer, polymorph, solvate (e.g., hydrate), pharmaceutically acceptable salt, ester, metabolite, N-oxide thereof, its chemically protected form or prodrug as a first therapeutic agent, or the pharmaceutical composition as a first pharmaceutical composition;

b) an optional second container containing at least one additional therapeutic agent as a second therapeutic agent, or a pharmaceutical composition comprising the additional therapeutic agent as a second pharmaceutical composition; and c) an optional package insert.

The present invention further encompasses the compound of general formula (I) or a stereoisomer, tautomer, polymorph, solvate (e.g., hydrate), pharmaceutically acceptable salt, ester, metabolite, N-oxide thereof, its chemically protected form or prodrug, or the pharmaceutical composition, for use in the prophylaxis or treatment of a disease or disorder mediated by FXR.

The present invention further encompasses use of the compound of general formula (I) or a stereoisomer, tautomer, polymorph, solvate (e.g., hydrate), pharmaceutically acceptable salt, ester, metabolite, N-oxide thereof, its chemically protected form or prodrug, or the pharmaceutical composition, in the manufacture of a medicament for the prophylaxis or treatment of a disease or disorder mediated by FXR.

The present invention further encompasses methods for preparing the compounds of the present invention and corresponding intermediates.

The compound of general formula (I) of the present invention has excellent in vivo or in vitro pharmacodynamic or pharmacokinetic properties, exhibits good FXR activation activity and activation effect, as well as excellent plasma drug exposure and bioavailability, and thus has good pharmaceutical activity and in vivo metabolic advantages.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literatures, patents and similar materials differs from or contradicts this application, including but not limited to defined terms, term usage, described techniques, or the like, this application controls.

Definitions

Unless otherwise defined in the context, all technical and scientific terms used herein are intended to have the same meaning as commonly understood by a person skilled in the art.

The terms "contain", "include", "comprise", "have", or "relate to", as well as other variations used herein are inclusive or open-ended, and do not exclude additional unenumerated elements or method steps.

The term "alkyl" as used herein refers to a saturated straight-chain or branched hydrocarbon radical of one to twelve carbon atoms ($C_{1-12}$), wherein the alkyl group may be optionally substituted with one or more (e.g., 1, 2, 3 or 4) suitable substituents. In some embodiments, an alkyl group has one to eight carbon atoms ($C_{1-8}$), particularly one to six carbon atoms ($C_{1-6}$). In other embodiments, an alkyl group has one to four carbon atoms ($C_{1-4}$), particularly one to three carbon atoms ($C_{1-3}$) or one to two carbon atoms ($C_{1-2}$). Exemplary alkyl groups include but are not limited to methyl (Me), ethyl (Et), 1-propyl (n-Pr), 2-propyl (i-Pr or isopropyl), 1-butyl (n-Bu or n-butyl), 2-methyl-1-propyl (i-Bu or isobutyl), 2-butyl (s-Bu or s-butyl), 2-methyl-2-propyl (t-Bu or tert-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl ($—C(CH_3)_2CH_2CH_2CH_3$), 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

As used herein, the term "alkenyl" refers to a linear or branched monovalent hydrocarbyl, which contains one double bond and 2-6 carbon atoms ("$C_{2-6}$ alkenyl"). Said alkenyl group is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic carbon ring having 3 to 12 carbon atoms ($C_{3-12}$), particularly 3 to 10 carbon atoms ($C_{3-10}$) or 3 to 8 carbon atoms ($C_{3-8}$). In some embodiments, a cycloalkyl group has 3 to 6 carbon atoms ($C_{3-6}$), such as 3, 4, 5, or 6 carbon atoms. Examples of cycloalkyl include but are not limited to cyclopropyl, cyclobutyl, cyclopentyl, cyclohexyl, cycloheptyl, cyclooctyl, cyclononyl, cyclodecyl, cycloundecyl, cyclododecyl, and the like. Cycloalkyl can be optionally substituted with one or more (e.g., one, two, three, or four) suitable substituents.

The term "aryl" as used herein refers to a $C_{6-14}$ aromatic monocyclic or polycyclic (especially bicyclic) group ($C_{6-14}$ aryl), suitably including a $C_{6-12}$ aryl group, more suitably including a $C_{6-10}$ monocyclic or bicyclic aryl group, and preferably refers to a $C_6$ aryl group (i.e., phenyl). The aryl group contains at least one aromatic ring (such as one ring or two rings), but may also comprise a non-aromatic additional ring. An example of a typical aryl group comprising one aromatic ring is phenyl. An example of a typical aryl group comprising two aromatic rings is naphthyl. Phenyl fused to a $C_{5-8}$ carbocyclyl group (suitably a $C_{5-6}$ carbocyclyl group) (such as indan) is also an example of an aryl group. The aryl group is optionally substituted with one or more (e.g., one, two, three, or four) suitable substituents.

The terms "heterocyclic" and "heterocyclyl" are used interchangeably herein and refer to a saturated (i.e., heterocycloalkyl) or partially unsaturated (i.e., having one or more double and/or triple bonds within the ring) cyclic group having, e.g., 3 to 14 (suitably 3 to 8, more suitably 3, 4, 5, or 6) ring atoms, wherein at least one ring atom is a heteroatom selected from the group consisting of N, O and S and the remaining ring atoms are C. For example, "3- to 14-membered heterocyclyl" is a saturated or partially unsaturated heterocyclyl group having 2 to 13 (e.g., 2, 3, 4, 5, 6, 7, 8, 9, 10, 11, 12 or 13) ring carbon atoms and one or more (e.g., 1, 2, 3, or 4) heteroatoms independently selected from the group consisting of N, O and S. Examples of saturated heterocyclyl (i.e., heterocycloalkyl) include but are not limited to oxiranyl, aziridinyl, azetidinyl, oxetanyl, tetrahydrofuranyl, pyrrolidinyl, pyrrolidinonyl, imidazolidinyl, pyrazolidinyl, tetrahydropyranyl, piperidinyl, morpholinyl, dithianyl, thiomorpholinyl, piperazinyl or trithianyl; and examples of partially unsaturated heterocyclyl include but are not limited to dioxolinyl and pyrrolinyl. Heterocyclyl can be optionally substituted with one or more (e.g., one, two, three, or four) suitable substituents.

The term "heteroaryl" as used herein refers to a monocyclic or polycyclic (e.g., bicyclic or tricyclic) aromatic ring system having 5 to 14 ring atoms, e.g., 5, 6, 7, 8, 9, 10, 11, 12, 13 or 14 ring atoms, specifically having 1, 2, 3, 4, 5, 6, 7, 8, 9, 10, 11, 12 or 13 carbon atoms and 1, 2, 3, 4 or 5 same or different heteroatoms independently selected from the group consisting of N, O and S.

Heteroaryl can be benzo-fused. Examples of heteroaryl include but are not limited to pyridyl, pyrimidinyl, pyrazinyl, pyridazinyl, thiazolyl, thienyl, oxazolyl, furyl, pyrrolyl, pyrazolyl, triazolyl, tetrazolyl, isoxazolyl, isothiazolyl, imidazolyl, triazinyl, oxadiazolyl, thiadiazolyl, benzothiazolyl, benzoisothiazolyl, imidazopyridyl, quinolinyl, indolyl, pyrrolopyridazinyl, benzofuranyl, benzothienyl, indazolyl, benzoxazolyl, benzoisoxazolyl, quinazolinyl, pyrrolopyridyl, pyrazolopyrimidyl, imidazopyridazinyl, pyrazolopyridyl, triazolopyridyl, isoquinolinyl, tetrahydroisoquinolinyl, benzimidazolyl, cinnolinyl, indolizinyl, phthalazinyl, isoindolyl, pteridinyl, purinyl, furazanyl, benzofurazanyl, quinoxalinyl, naphthyridinyl and furopyridinyl. Preferably, the heteroaryl group is selected from the group consisting of pyridyl, pyrimidinyl, pyrazinyl, pyridazinyl, thiazolyl, oxazolyl, benzothiazolyl, benzo[d]isothiazolyl, imidazo[1,2-a]pyridyl, quinolinyl, 1H-indolyl, pyrrolo[1,2-b]pyridazinyl, benzofuranyl, benzo[b]thienyl, 1H-indazolyl, benzo[di]oxazolyl, benzo[di]isoxazolyl, quinazolinyl, 1H-pyrrolo[3,2-c]pyridyl, pyrazolo[1,5-a]pyrimidinyl, imidazo[1,2-b]pyridazinyl, pyrazolo[1,5-a]pyridyl and 1H-[1,2,3]triazolo[4,5-b]pyridyl. Heteroaryl can be optionally substituted with one or more (e.g., one, two, three or four) suitable substituents.

The heterocyclyl (e.g., heterocycloalkyl) or heteroaryl groups may be carbon (carbon-linked) or nitrogen (nitrogen-linked) bonded where possible. By way of example and not as a limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7 or 8 of a quinoline or position 1, 3, 4, 5, 6, 7 or 8 of an isoquinoline.

By way of example and not as a limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole or isoindoline, position 4 of a morpholine and position 9 of a carbazole or β-carboline.

As used herein, the term "halo" or "halogen" includes F, Cl, Br or I. "Halo" includes but is not limited to mono-substitution, di-substitution or tri-substitution, and the halogen atom for the substitution can be same or different.

The term "substituted" means that one or more (e.g., one, two, three or four) hydrogen(s) on a designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means (1) unsubstituted, or (2) substituted with a specified group, radical or moiety.

When a bond to a substituent is shown as crossing a bond connecting two atoms in a ring, then such substituent may be bonded to any of the ring-forming atoms in that ring that are substitutable.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. In one aspect, a stereoisomer of this invention can be present in predominant form, e.g. greater than 50% ee (enantiomeric excess), greater than 80% ee, greater than 90% ee, greater than 95% ee, or greater than 99% ee.

Where the processes for the preparation of the compounds according to the invention give rise to a mixture of stereoisomers, these isomers may be separated by conventional techniques such as preparative chromatography. The compounds may be prepared in a racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic purification and removal of the chiral auxiliary. Alternatively, the compounds may be resolved using a chiral HPLC column.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention encompasses all possible crystalline forms or polymorphs of the compound of general formula (I), either as a single polymorph, or as a mixture of more than one polymorphs, in any ratio.

It should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, metabolite N-oxide as well as a chemically protected form and prodrug, which can directly or indirectly provide the compound of the present invention or a metabolite or residue thereof after being administered to a patient in need thereof.

Therefore, "compound of general formula (I)", "compound of the present invention" or "compound of general formula (I) of the present invention" mentioned herein also means to encompass a solvate (e.g., hydrate), pharmaceutically acceptable salt, ester, metabolite, N-oxide, as well as chemically protected form and prodrug of the compound of general formula (I).

The phrase "pharmaceutically acceptable salt" as used herein, refers to pharmaceutically acceptable organic or inorganic salts of a compound of the invention. Exemplary salts include but are not limited to sulfate, acetate, chloride, iodide, nitrate, bisulfate, acid phosphate, isonicotinate, salicylate, acid citrate, oleate, tannate, pantothenate, bitartrate, ascorbate, gentisinate, gluconate, glucuronate, saccharate, formate, benzoate, glutamate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ions.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid (such as glucuronic acid or galacturonic acid), an alpha hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid) or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include but are not limited to organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

As used herein, the term "ester" refers to those derived from the compounds of general formula (I) in the present application, which include physiologically-hydrolyzable esters (which may be hydrolyzed under physiological conditions to release the compounds of general formula (I) of the present invention in the form of free acids or alcohols). The compound of general formula (I) of the present invention itself may be an ester as well.

The compound of the present invention may exist in the form of a solvate (e.g., hydrate), wherein the compound of the present invention contains a polar solvent, in particular water, methanol or ethanol, for example, as a structural element of the crystal lattice of the compound. Polar solvents, in particular water, may exist in a stoichiometric or non-stoichiometric amount.

A "metabolite" is a product produced through metabolism in the body of a specified compound or salt thereof. Metabolites of a compound may be identified using routine techniques known in the art and their activities determined using tests such as those described herein. Such products can result for example from the oxidation, reduction, hydrolysis, amidation, deamidation, esterification, enzymatic cleavage, and the like, of the administered compound. Accordingly, the present invention includes metabolites of the compounds of the present invention, including compounds produced by a process comprising contacting a compound of general formula (I) of the present invention with a mammal for a period of time sufficient to yield a metabolic product thereof.

As can be appreciated by a person skilled in the art, not all nitrogen-containing heterocycles can form N-oxides since the nitrogen requires an available lone-pair electron for oxidation to the oxide; a person skilled in the art will recognize those nitrogen-containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (m-CPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; S. V. Ley, Ed., Pergamon Press; M. Tisler and B. Stanovnik, *Comprehensive Heterocyclic Chemistry*, vol. 3, pp 18-20.

During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The present invention further includes prodrugs of the compounds of this invention within its scope. In general, such prodrugs will be functional derivatives of the compounds which are readily convertible in vivo into the desired therapeutically active compound. Thus, in these cases, the term "administering" in the methods of treatment of the present invention shall encompass the treatment of the various diseases or disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Any general formula or structure given herein, including the compound of general formula (I), is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of formula (I). The concentration of such a heavier isotope, specifically deuterium, may be defined by an isotopic enrichment factor. In the compounds of the present invention, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of the present invention, any atom specifically designated as a deuterium (D) is meant to represent deuterium.

The term "pharmaceutical composition" as used herein includes a product comprising a therapeutically effective amount of a compound of general formula (I) of the present invention, as well as any product produced directly or indirectly from a combination of a compound of general formula (I) of the present invention.

Compound

In some embodiments, the present invention provides a compound of general formula (I) or a stereoisomer, tautomer, polymorph, solvate (e.g., hydrate), pharmaceutically acceptable salt, ester, metabolite, N-oxide thereof, its chemically protected form or prodrug,

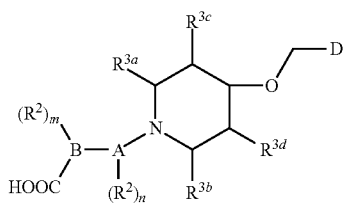

(I)

wherein:

A is selected from the group consisting of thiazolylene, phenylene and pyridylene;

B is selected from the group consisting of $C_{6-10}$ aryl and 5- to 10-membered heteroaryl containing 1, 2, 3 or 4 heteroatoms independently selected from the group consisting of N, O and S;

D is

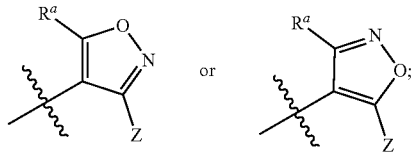

Z is

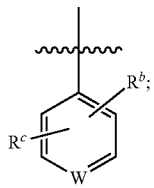

W is selected from the group consisting of N and $CR^d$, preferably is $CR^d$;

$R^a$ is selected from the group consisting of hydrogen, $C_{1-6}$ alkyl, $C_{2-6}$ alkenyl, $C_{2-6}$ alkynyl, $C_{3-8}$ cycloalkyl, 3- to 14-membered heterocyclyl, $C_{1-6}$ alkyl-O—, $C_{1-6}$ haloalkyl, $C_{3-8}$ halocycloalkyl and $C_{1-6}$ haloalkyl-O—;

$R^b$, $R^c$ and $R^d$ are each independently selected from the group consisting of hydrogen, halogen, hydroxyl, cyano, —$NH_2$, nitro, $C_{1-6}$ alkyl, $C_{1-6}$ haloalkyl, $C_{1-6}$ alkyl-O—, $C_{1-6}$ haloalkyl-O—, $C_{3-8}$ cycloalkyl, $C_{3-8}$ halocycloalkyl, $C_{3-8}$ cycloalkyl-O— and $C_{3-8}$ halocycloalkyl-O—;

$R^1$ and $R^2$ are each independently selected from the group consisting of hydrogen, halogen, cyano, hydroxyl, —$NH_2$, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl, $C_{3-8}$ halocycloalkyl, $C_{1-6}$ alkyl-NH— and $(C_{1-6}$ alkyl$)_2$-N—;

$R^{3a}$, $R^{3b}$, $R^{3c}$ and $R^{3d}$ are each independently selected from the group consisting of hydrogen, halogen, cyano, hydroxyl, —$NH_2$, oxo, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl and $C_{3-8}$ halocycloalkyl; alternatively, any two of $R^{3a}$, $R^{3b}$, $R^{3c}$ and $R^{3d}$ together form $C_{1-6}$ alkylene, preferably, any two of $R^{3a}$, $R^{3b}$, $R^{3c}$ and $R^{3d}$ together form $C_{2-6}$ alkylene, and more preferably, $R^{3a}$ and $R^{3b}$ together form $C_{2-6}$ alkylene;

m and n are each independently 0, 1, 2, 3 or 4, preferably 0, 1 or 2; and the above alkyl, alkylene, alkenyl, alkynyl, cycloalkyl, heterocyclyl, aryl and heteroaryl are each optionally substituted with 1, 2, or 3 substituents independently selected from the group consisting of halogen, hydroxyl, oxo, cyano, —$NH_2$, nitro, $C_{1-6}$ alkyl, $C_{1-6}$ haloalkyl, $C_{1-6}$ haloalkyl-O—, $C_{3-6}$ cycloalkyl, $C_{3-6}$ halocycloalkyl, $C_{1-6}$ alkyl-NH—, $(C_{1-6}$ alkyl$)_2$-N—, $C_{1-6}$ hydroxyalkyl, cyano-$C_{1-6}$ alkyl, 3- to 14-membered heterocyclyl, $C_{6-14}$ aryl and 5- to 14-membered heteroaryl.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein A is selected from the group consisting of

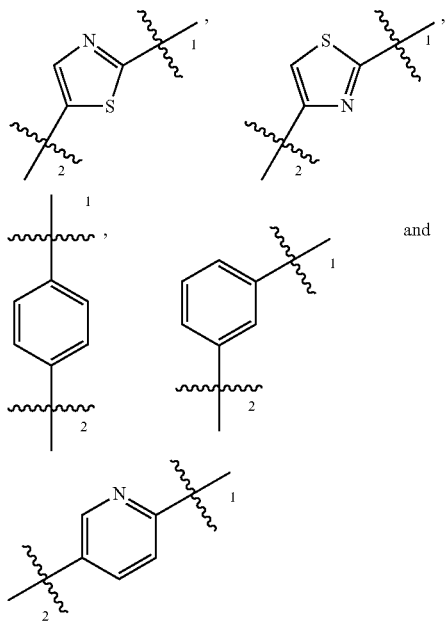

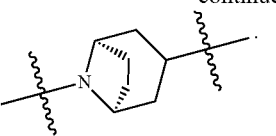

and

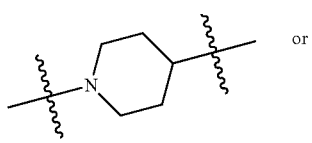

attached to the ring nitrogen atom in general formula (I) at either of the two positions labeled 1 or 2, and attached to group B at the other position.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein B is selected from the group consisting of phenyl and 5- to 6-membered heteroaryl containing 1, 2, 3 or 4 heteroatoms independently selected from the group consisting of N, O and S; particularly, the heteroaryl is selected from the group consisting of pyridyl, pyrimidinyl, pyrazinyl, pyridazinyl, thiazolyl, thienyl, oxazolyl, furyl, pyrrolyl, pyrazolyl, triazolyl, tetrazolyl, isoxazolyl, isothiazolyl, imidazolyl, triazinyl, oxadiazolyl and thiadiazolyl; and B is preferably selected from the group consisting of phenyl, pyridyl, furyl, thienyl and pyrazolyl.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the group

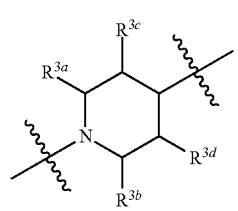

in general formula (I) is

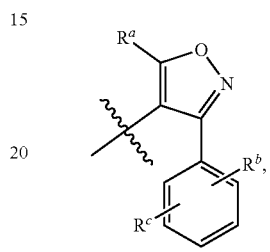

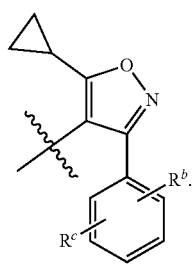

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein D is preferably In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the $C_{1-6}$ alkyl is selected from the group consisting of methyl, ethyl, n-propyl, isopropyl, n-butyl, isobutyl and tert-butyl.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the halogen is selected from the group consisting of F, Cl, Br and I, and preferably is F or Cl.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the $C_{1-6}$ haloalkyl is selected from the group consisting of $CF_3$, $CHF_2$, $CH_2F$, $CCl_3$ and $CH_2CF_3$.

In preferred embodiments, $R^a$ is cyclopropyl.

In preferred embodiments, $R^b$, $R^c$ and $R^d$ are each independently selected from the group consisting of hydrogen, F, Cl, Br, I, $CH_3$, $OCH_3$, $CF_3$ and $OCF_3$.

In preferred embodiments, $R^1$ and $R^2$ are each independently selected from the group consisting of hydrogen, F, Cl, Br, I, $CH_3$, $CF_3$ and $CH(CH_3)_2$; preferably, $R^1$ and $R^2$ are each independently selected from the group consisting of hydrogen, F, Cl, Br, I and $CH_3$.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the compound a compound of general formula (Ia), (Ib), (Ic) or (Id):

(Ia)
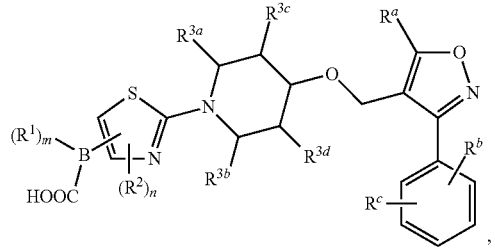

, (Ib)
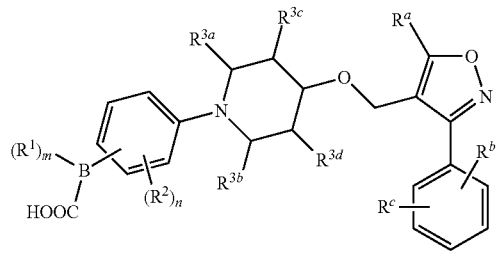

, (Ic)
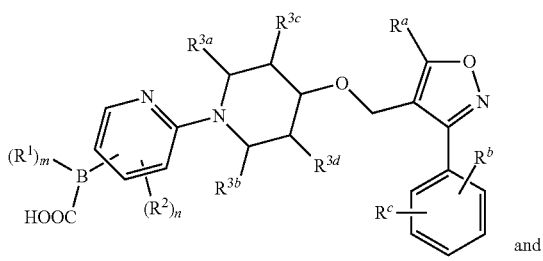

and (Id)
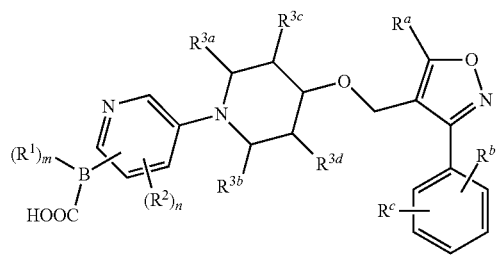

.

In some embodiments, the present invention provides the compound or a stereoisomer, tautomer, polymorph, solvate (e.g., hydrate), pharmaceutically acceptable salt, ester, metabolite, N-oxide thereof, its chemically protected form or prodrug, wherein the compound is selected from the group consisting of:

C1
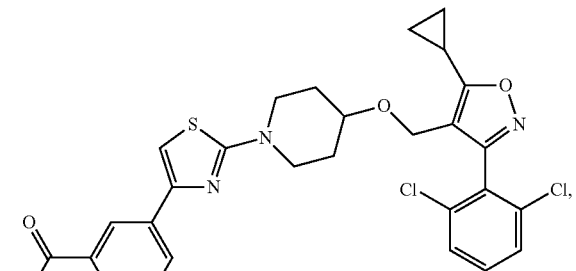

,

C2
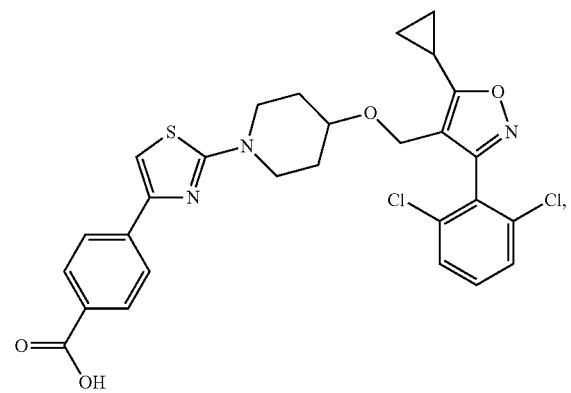

,

C3
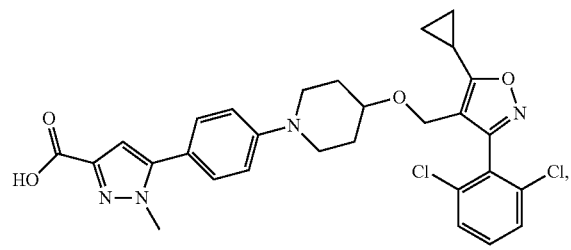

,

C4
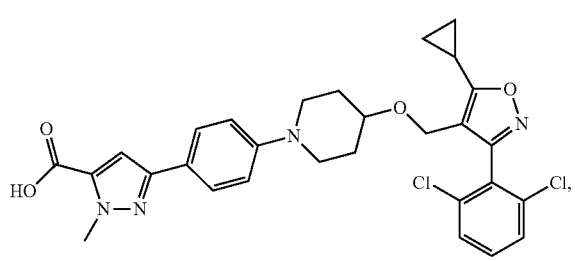

,

-continued
C5
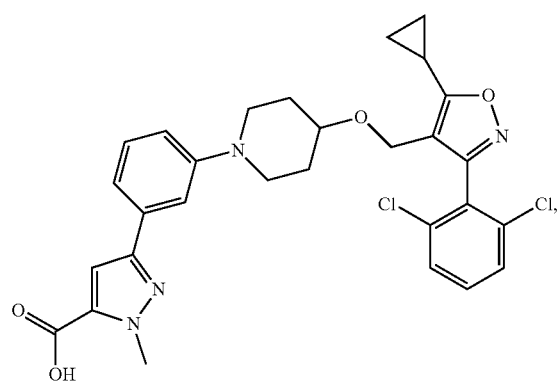
C6
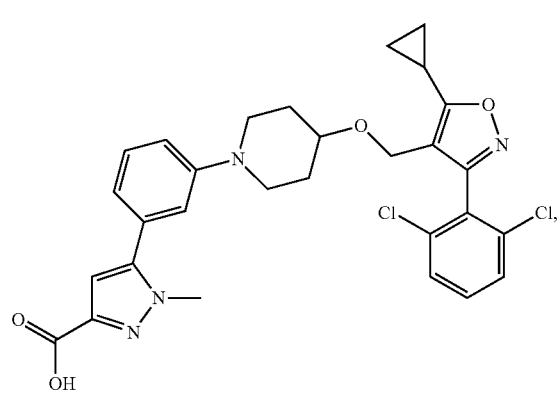
C7
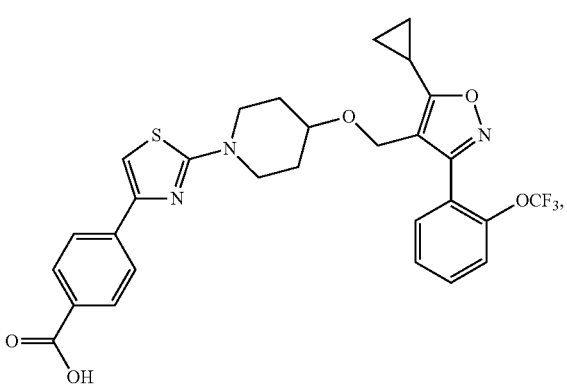
C8
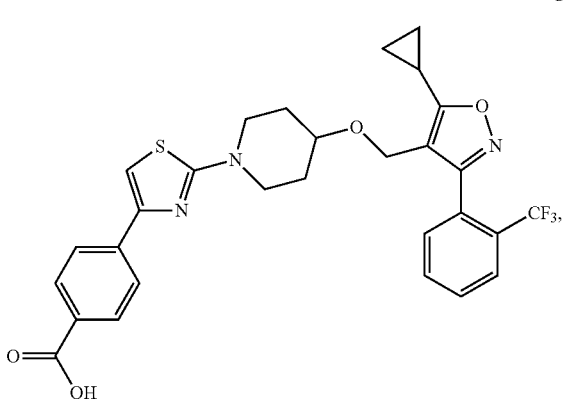
-continued
C9
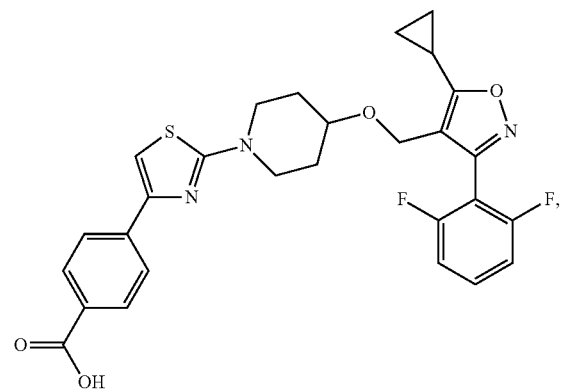
C10
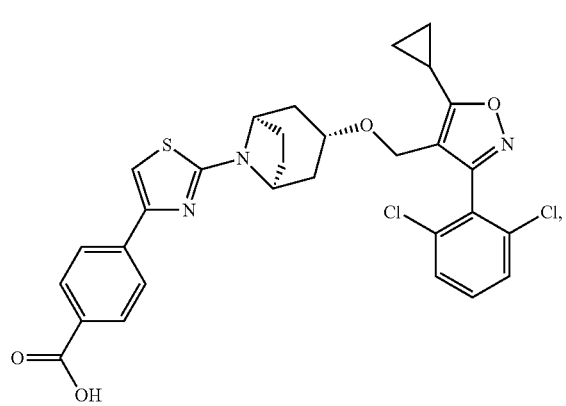
C11
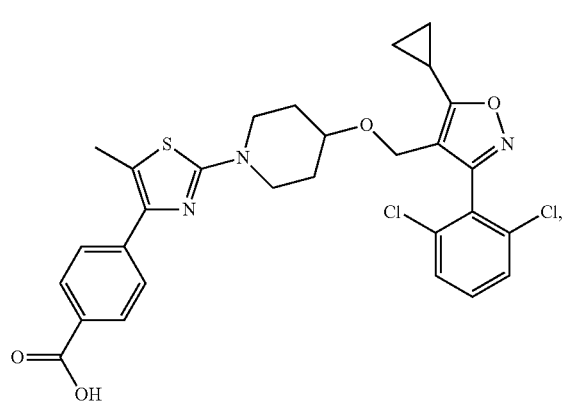
C12
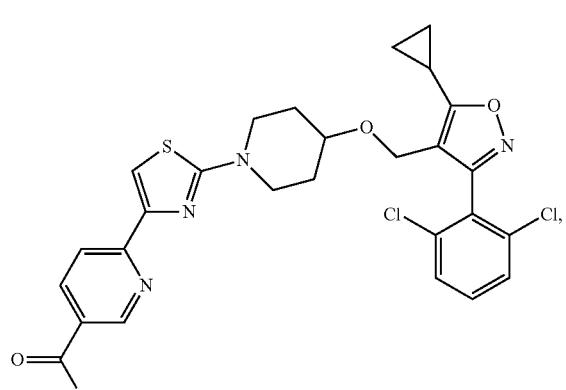

C13
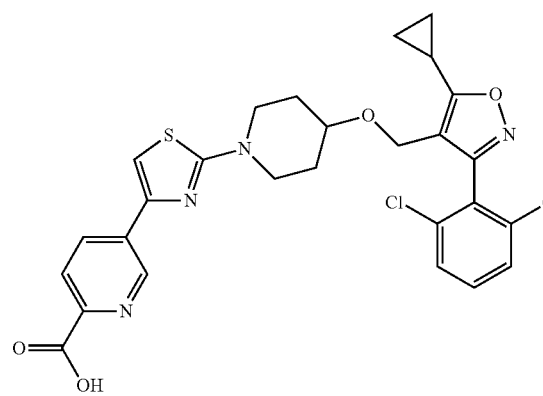
C14
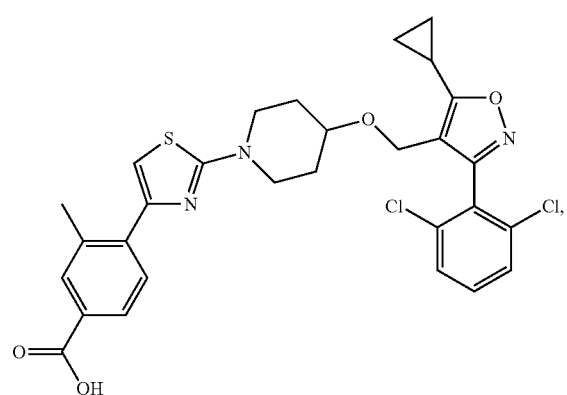
C15
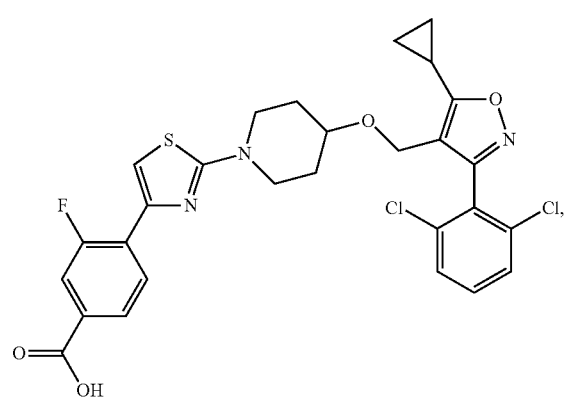
C16
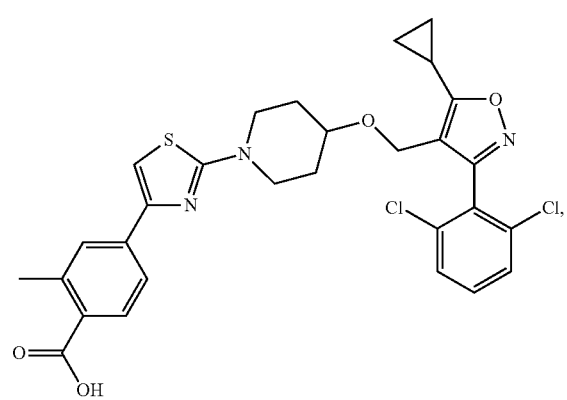
C17
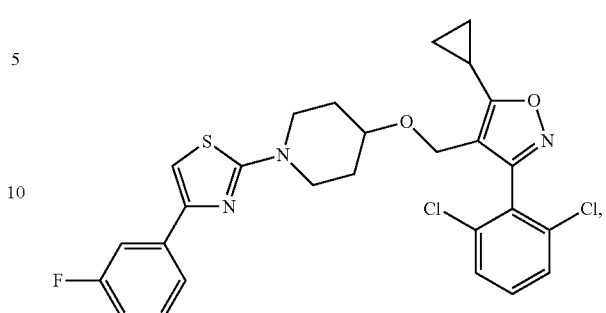
C18
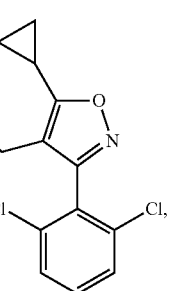
C19
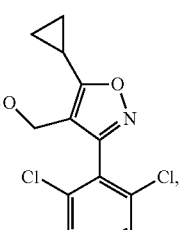
C20
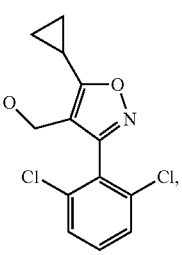
C21

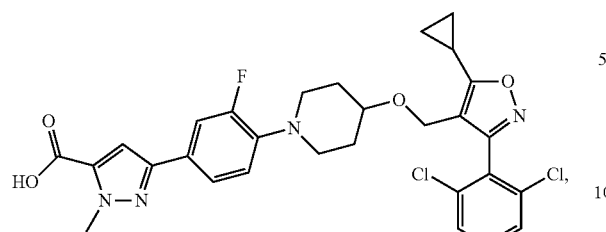
C22
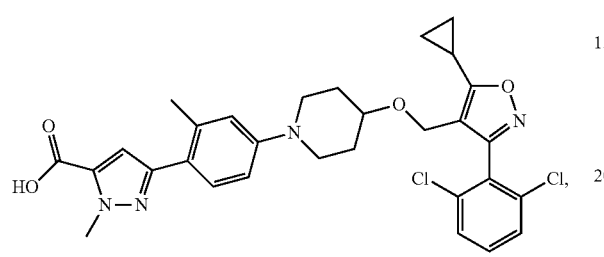
C23
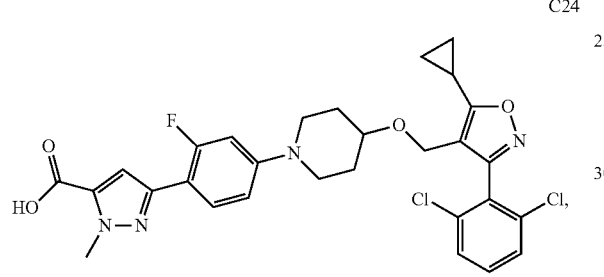
C24
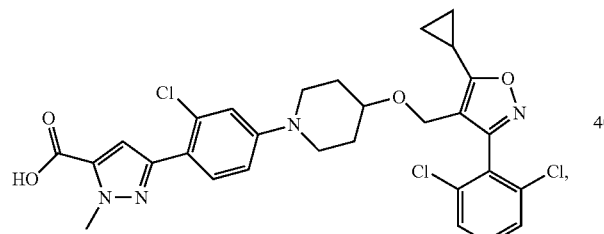
C25
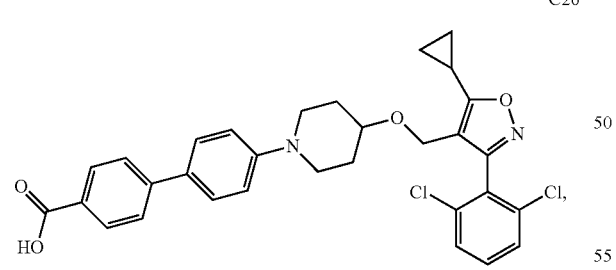
C26
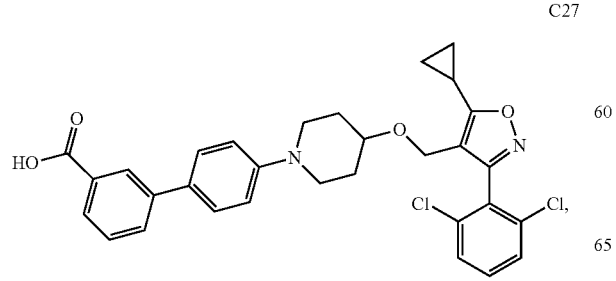
C27
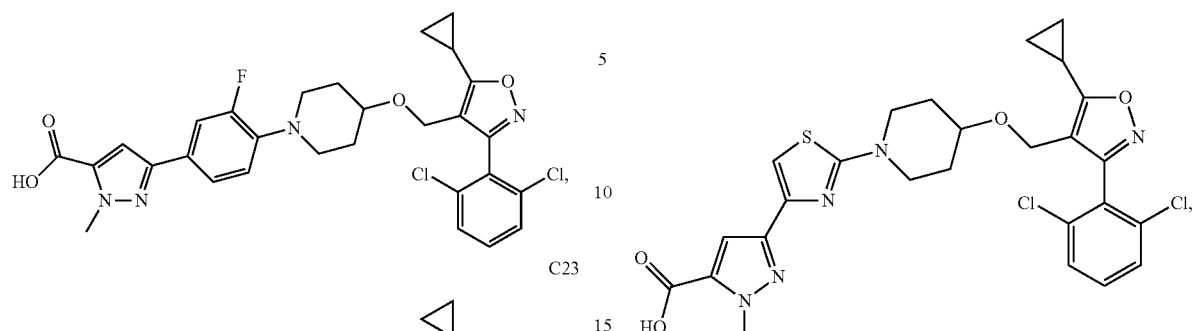
C28
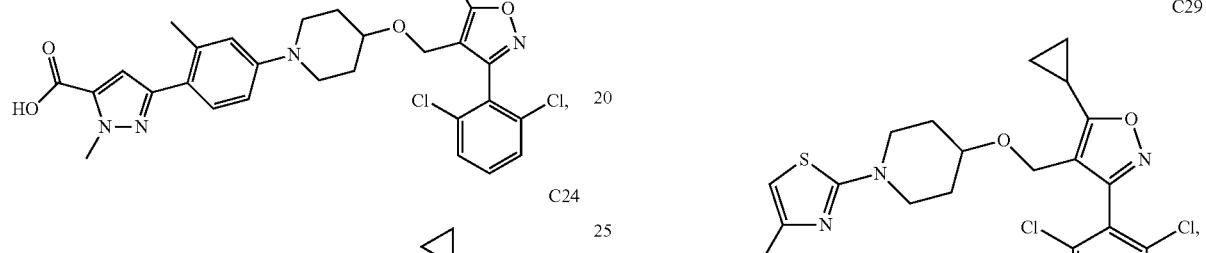
C29
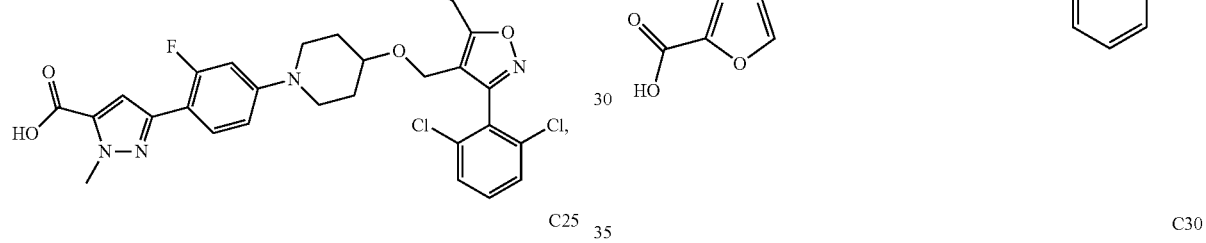
C30
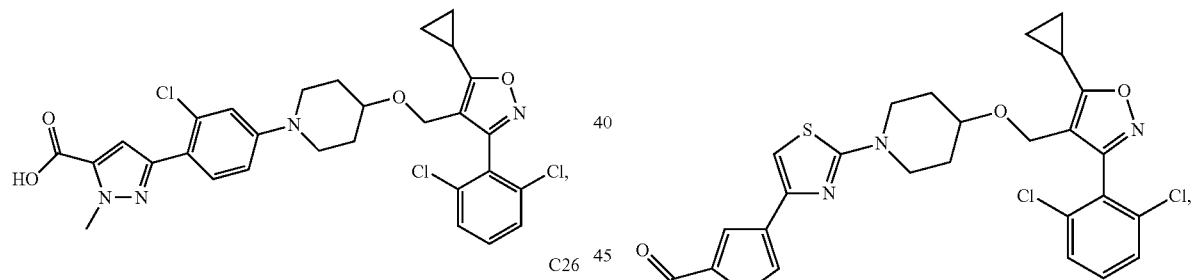
C31

C32
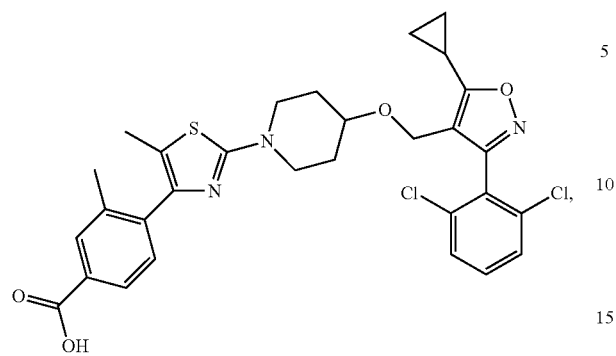
C33
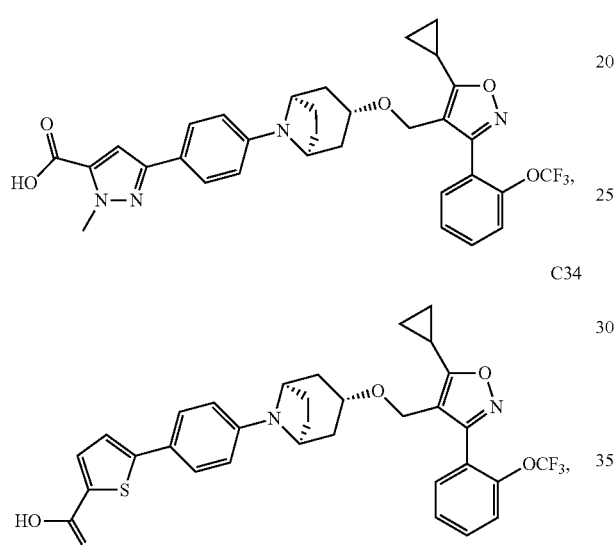
C34
C35
C36
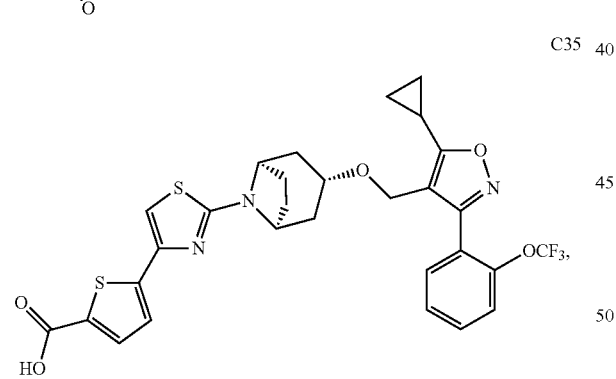
C37
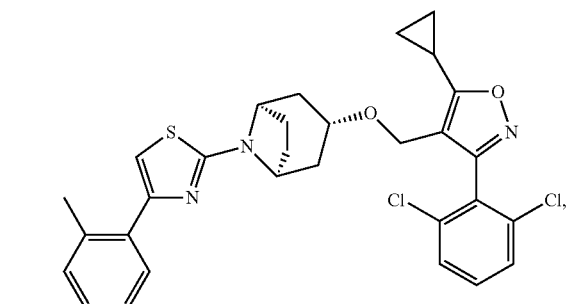
C38
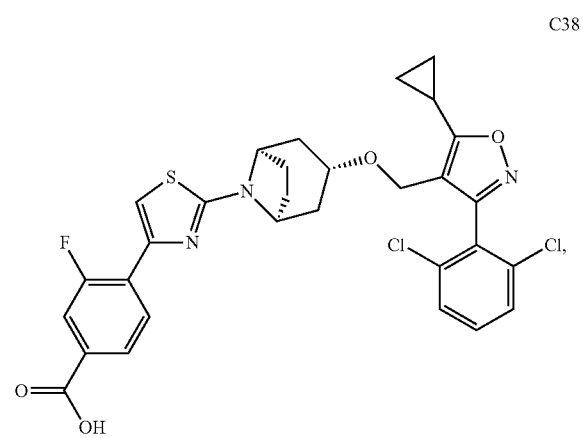
C39
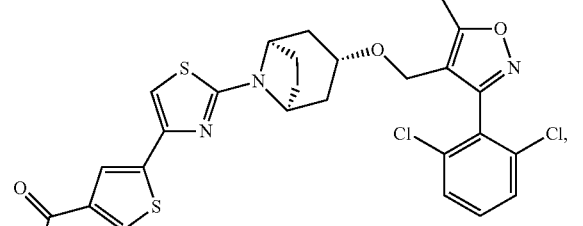
C40
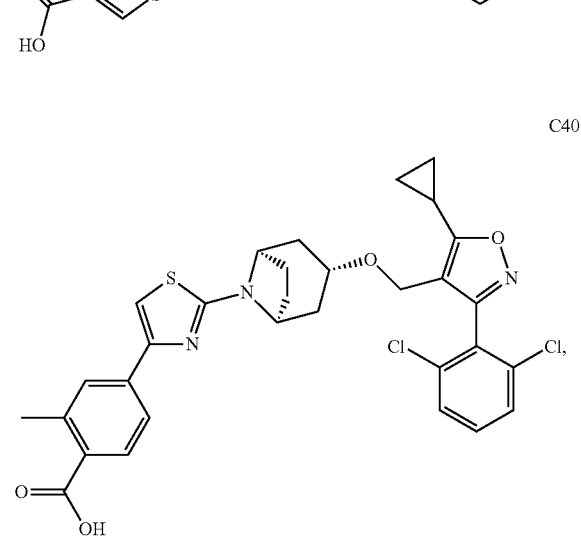

25
-continued
C41
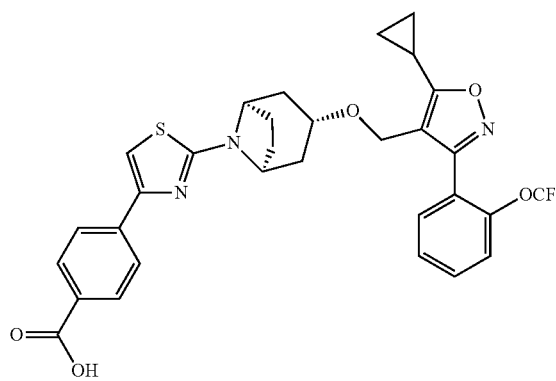
C42
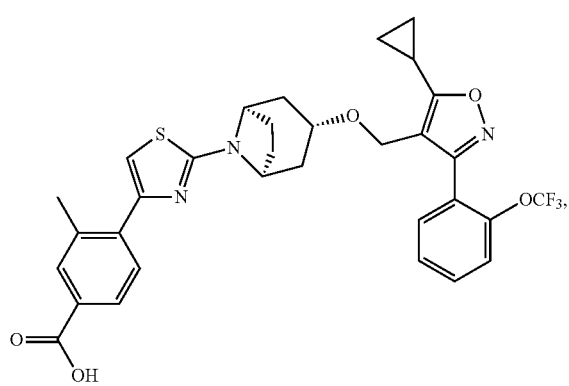
C43
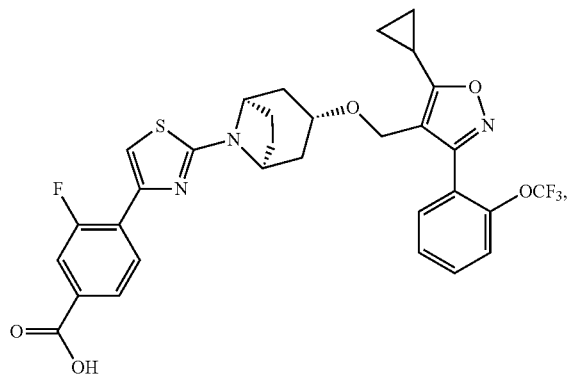
C44
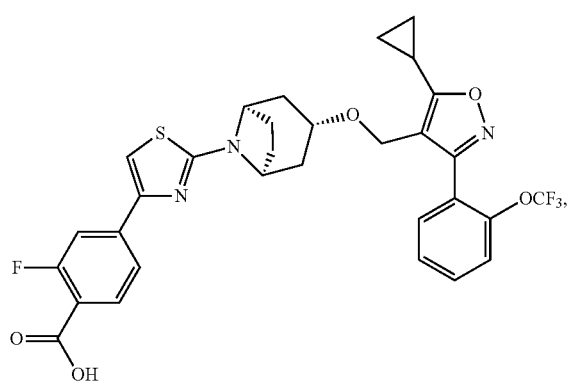
26
-continued
C45
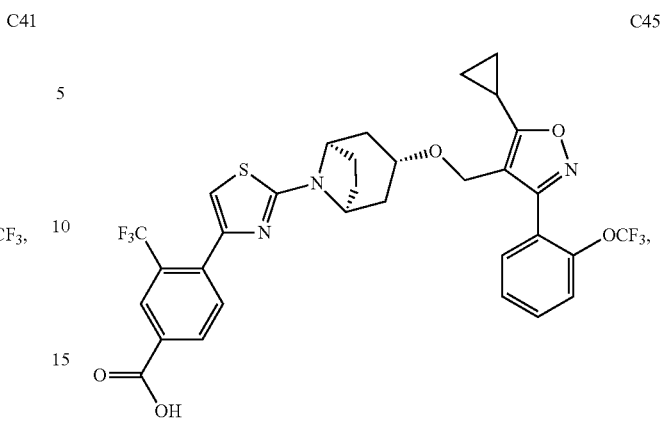
C46
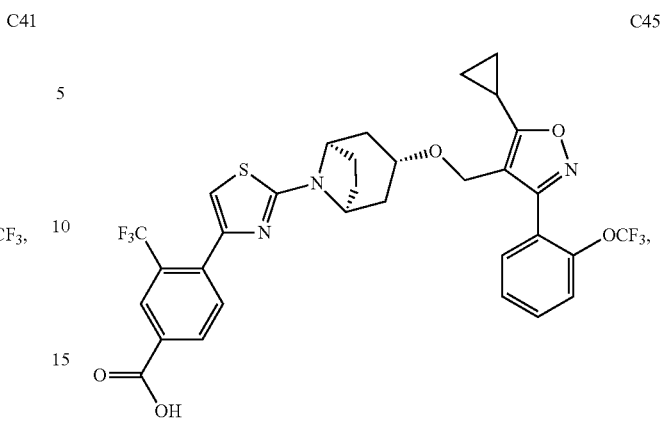
C47
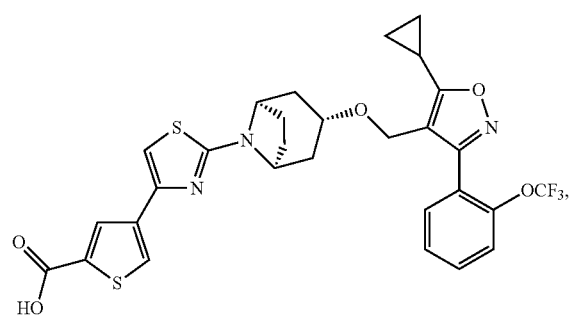
C48
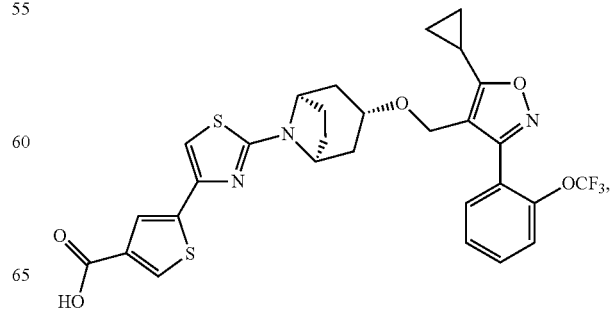

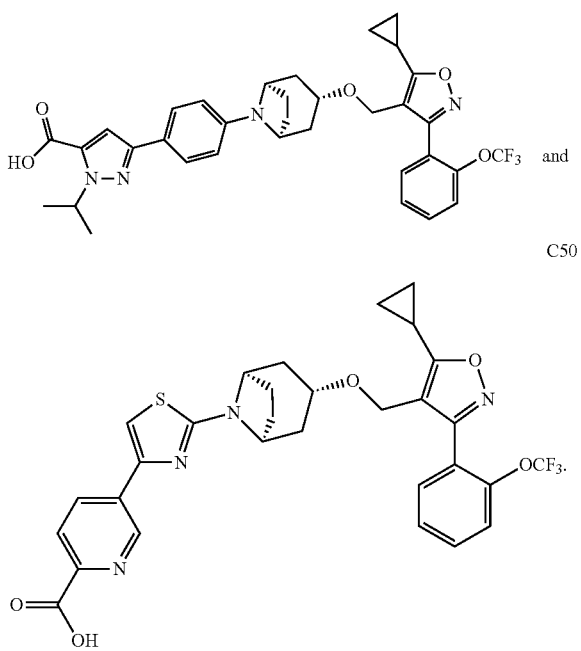

The compound of general formula (I) of the present invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if the compound of general formula (I) incorporates a double bond or a fused ring, the cis- and trans-forms, as well as mixtures thereof, are embraced within the scope of the invention. In the structures shown herein, where the stereochemistry of any particular chiral atom is not specified, then all stereoisomers are contemplated and included as the compounds of the present invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embraces both solvated and unsolvated forms.

The compounds of the present invention may also exist in different tautomeric forms, and all such forms are embraced within the scope of the invention.

It should also be understood that combinations of any two or more of the embodiments are also included within the scope of the present invention.

Pharmaceutical Composition

Another aspect of the present invention provides a pharmaceutical composition comprising at least one compound of general formula (I) of the present invention as described above or a stereoisomer, tautomer, polymorph, solvate (e.g., hydrate), pharmaceutically acceptable salt, ester, metabolite, N-oxide thereof, its chemically protected form or prodrug, and one or more pharmaceutically acceptable carriers. In some embodiments, the pharmaceutical composition can further comprise one or more additional therapeutic agents, e.g., those suitable for the prophylaxis or treatment of a disease or disorder mediated by FXR.

The term "pharmaceutically acceptable carrier" in the present invention refers to a diluent, auxiliary material, excipient, or vehicle with which an active ingredient is administered, and it is, within the scope of sound medical judgment, suitable for contact with the tissues of human beings and/or other animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to, sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical acceptable carriers are described in e.g., Remington's Pharmaceutical Sciences (1990).

The pharmaceutical composition of the present invention can act systemically and/or topically. To this end, it can be administered through a suitable route, such as through injection, intravenous, intraarterial, subcutaneous, intraperitoneal, intramuscular or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablet, capsule, lozenge, hard candy, powder, spray, cream, salve, suppository, gel, paste, lotion, ointment, aqueous suspension, injectable solution, elixir, and syrup.

Therapeutic Use

Another aspect of the present invention provides therapeutic use of the compound and pharmaceutical composition.

Accordingly, in some embodiments, the present invention relates to a method for the prophylaxis or treatment of a disease or disorder mediated by FXR, comprising administering to a subject in need thereof a therapeutically effective amount of at least one compound of general formula (I) of the present invention, or a stereoisomer, tautomer, polymorph, solvate (e.g., hydrate), pharmaceutically acceptable salt, ester, metabolite, N-oxide thereof, its chemically protected form or prodrug, or administering the pharmaceutical composition of the present invention.

In other embodiments, the present invention relates to use of at least one compound of general formula (I) of the present invention or a stereoisomer, tautomer, polymorph, solvate (e.g., hydrate), pharmaceutically acceptable salt, ester, metabolite, N-oxide thereof, its chemically protected form or prodrug, or the pharmaceutical composition of the present invention, in the manufacture of a medicament for the prophylaxis or treatment of a disease or disorder mediated by FXR.

The diseases or disorders mediated by FXR include, but are not limited to:

chronic intrahepatic or some forms of extrahepatic cholestatic conditions; liver fibrosis; obstructive or chronic inflammatory disorders of the liver; liver cirrhosis; liver steatosis and associated syndromes; cholestatic or fibrotic effects that are associated with alcohol-induced cirrhosis or with viral-borne forms of hepatitis; liver failure or liver ischemia after major liver resection; chemotherapy associated steatohepatitis (CASH); acute liver failure;

inflammatory bowel diseases, dyslipidemia, atherosclerosis, diabetes and related diseases; lipid and lipoprotein disorders; type II diabetes and clinical complications of type I and type II diabetes, including diabetic nephropathy, diabetic neuropathy, diabetic retinopathy and other observed effects of clinically manifest long term diabetes; disorders and diseases which result from chronic fatty and fibrotic degeneration due to enforced lipid and specifically triglyceride accumulation and subsequent activation of profibrotic pathways, such as Non-Alcoholic Fatty Liver Disease (NAFLD), or Non-Alcoholic Steatohepatitis (NASH); obesity or metabolic syndrome (combined conditions of dyslipidemia, diabetes and abnormally high body-mass index);

acute myocardial infarction, acute stroke or thrombosis which occurs as an endpoint of chronic obstructive atherosclerosis; non-malignant hyperproliferative disorders and malignant hyperproliferative disorders, specifically hepatocellular carcinoma, colon adenoma and polyposis, colon adenocarcinoma, breast cancer, pancreas adenocarcinoma, Barrett's esophagus and other forms of neoplastic diseases of the gastrointestinal tract and the liver.

Unless otherwise indicated, the term "treating" or "treatment", as used herein, means reversing, alleviating, inhibiting the disease or disorder to which such term applies or the progress of one or more symptoms of such disease or disorder, or preventing the disease or disorder to which such term applies or one or more symptoms of such disease or disorder.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

As used herein, the term "therapeutically effective amount" refers to the amount of a compound being administered which achieve the therapeutic effects as described above.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, and more preferably 1-150 mg, etc.

Combination Therapy

The compound of general formula (I) may be employed alone or in combination with one or more additional therapeutic agents suitable for the prophylaxis or treatment of a disease or disorder mediated by FXR. In certain embodiments, the compound of general formula (I) is combined in the pharmaceutical composition, or dosing regimen as combination therapy, with e.g., an additional therapeutic agent that has anti-hyperproliferative properties. The additional therapeutic agent may be e.g., a chemotherapeutic agent. The additional therapeutic agent of the pharmaceutical composition or dosing regimen preferably has complementary activities to the compound of general formula (I) such that they do not adversely affect each other. Such compounds are suitably present in combination in amounts that are effective for the purpose intended.

The combination therapy may be administered as a simultaneous or sequential regimen. When administered sequentially, the combination may be administered in two or more administrations. The combined administration includes coadministration, using separate pharmaceutical compositions or a single pharmaceutical composition comprising the compound of general formula (I) and the additional therapeutic agent(s), and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and additional therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimens. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, the compound of general formula (I) or a stereoisomer, tautomer, polymorph, solvate (e.g., hydrate), pharmaceutically acceptable salt, ester, metabolite, N-oxide thereof, its chemically protected form or prodrug, may be combined with the additional therapeutic agent(s) such as those described herein, as well as combined with surgical therapy and radiotherapy. Combination therapies according to the present invention thus comprise the administration of at least one compound of general formula (I) or a stereoisomer, tautomer, polymorph, solvate (e.g., hydrate), pharmaceutically acceptable salt, ester, metabolite, N-oxide thereof, its chemically protected form or prodrug, and the use of at least one additional treatment method. The amounts of the compound(s) of general formula (I) and the additional therapeutic agent(s) and the relative timings of administration will be selected in order to achieve the desired combined therapeutic effect.

Metabolites of the Compound of General Formula (I)

Also falling within the scope of the present invention are the in vivo metabolic products of the compound of general formula (I) described herein. Such products may result for example from the oxidation, reduction, hydrolysis, amidation, deamidation, esterification, enzymatic cleavage, and the like, of the administered compound. Accordingly, the present invention includes metabolites of the compound of general formula (I), including compounds produced by a process comprising contacting a compound of the present invention with a mammal for a period of time sufficient to yield a metabolic product thereof.

Metabolites typically are identified by preparing a radio-labelled (e.g., $^{14}C$ or $^{3}H$) isotope of a compound of the present invention, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compound of the present invention.

Kit

In other embodiments of the present invention, a "kit" containing materials useful for the treatment of the diseases and disorders described above is provided. The kit comprises a container comprising the compound of general formula (I) or a stereoisomer, tautomer, polymorph, solvate (e.g., hydrate), pharmaceutically acceptable salt, ester, metabolite, N-oxide thereof, its chemically protected form or prodrug as a first therapeutic agent, or the pharmaceutical composition of the present invention as a first pharmaceutical composition. In certain embodiments, the kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold the compound of general formula (I) or a formulation thereof which is effective for treating the disorder and may have a sterile access port (for example, the container may be an intravenous solution bag or a vial having a stopper pierceable by a hypodermic injection needle). The label or package insert indicates that the composition is used for treating the disorder of choice, such as cancer. In addition, the label or package insert may indicate that the patient to be treated is one having a disease or disorder such as liver cirrhosis, a hyperproliferative disorder, atherosclerosis, type I diabetes or the like. The label or package insert may also indicate that the composition can be used to treat other disorders. In other embodiments, the kit further comprises a second container containing at least one additional therapeutic agent for the prophylaxis or treatment of a disease or disorder mediated by FXR as a second therapeutic agent, or a pharmaceutical composition comprising the additional therapeutic agent as a second pharmaceutical composition. Accordingly, in certain embodiments, the kit may further comprise instructions for the administration of the first therapeutic agent or first pharmaceutical composition and, if present, the second therapeutic agent or second pharmaceutical composition. For example, if the kit comprises a first composition comprising the compound of general formula (I) and a second pharmaceutical composition comprising an additional therapeutic agent, then the kit may further comprise instructions for the simultaneous, sequential or separate administration of the first and second pharmaceutical compositions to a patient in need thereof. Alternatively, or additionally, the kit may further comprise a third container comprising a pharmaceutically acceptable buffer, such as bacteriostatic water for injection (BWFI), phosphate-buffered saline, Ringer's solution and dextrose solution. The kit may further include other materials desirable from a commercial and user standpoint, including other buffers, diluents, filters, needles for injection, and syringes.

In other embodiments, the kits are suitable for the delivery of solid oral forms of the compound of general formula (I), such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

Method for Preparing the Compound

In some embodiments, the present invention provides a method for preparing the compound of general formula (I) of the present invention, wherein the method comprises the following steps:

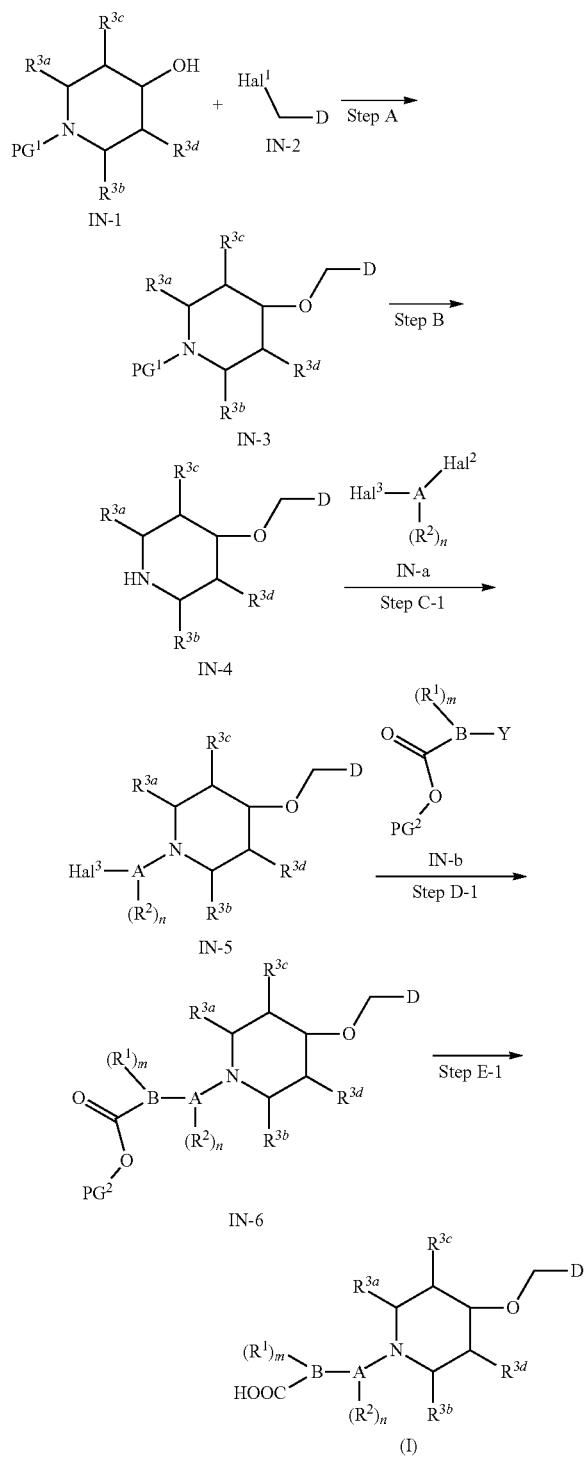

wherein:

Hal$^1$, Hal$^2$ and Hal$^3$, each independently, are same or different halogens, e.g., F, Cl, Br or I, preferably Cl or Br;

PG$^1$ is an amino protecting group, preferably tert-butyloxycarbonyl (Boc);

PG$^2$ is a carboxy protecting group, preferably C$_{1-6}$ alkyl, and more preferably methyl;

Y is a boronic acid or borate group, preferably —B(OH)$_2$ or

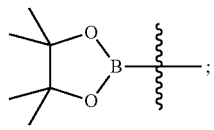 [SMILES: *B1OC(C)(C)C(C)(C)O1]

the remaining groups are as defined above;

the reaction conditions for each step are as follows:

Step A: Reacting Compound IN-1 With Compound IN-2 to Obtain Compound IN-3

The reaction is preferably performed in a suitable organic solvent. The organic solvent can be selected from the group consisting of linear or cyclic ethers (e.g., tetrahydrofuran or diethyl ether, etc.), N-methylpyrrolidone, dimethylformamide, dimethylacetamide, 1,4-dioxane, dimethyl sulfoxide and any combination thereof, while tetrahydrofuran or dimethylformamide is preferred. The reaction is preferably performed in the presence of a suitable base (e.g., an alkali metal alkoxide or carbonate) and/or a catalyst. The catalyst can be a catalyst system comprising a crown ether, which can be selected from the group consisting of 15-crown-5 and 18-crown-6; the alkali metal carbonate is e.g., potassium carbonate or cesium carbonate; the alkali metal alkoxide can be selected from the group consisting of sodium tert-butoxide, potassium tert-butoxide, sodium methoxide, potassium methoxide, sodium ethoxide, and potassium ethoxide. Preferably, the alkali metal alkoxide and catalyst are a combination of sodium tert-butoxide and/or potassium tert-butoxide with 15-crown-5 and/or 18-crown-6, preferably a combination of sodium tert-butoxide with 15-crown-5 or a combination of potassium tert-butoxide with 18-crown-6. The reaction is preferably performed at a suitable temperature. The temperature preferably is room temperature (20-30° C.) or 50-100° C. (e.g., 50-80° C.). The reaction is preferably performed for a suitable period of time, such as 1-24 hours, e.g., 5-15 hours.

Step B: Removing the PG$^1$ Group in Compound IN-3 to Obtain Compound IN-4

The reaction is preferably performed in a suitable organic solvent. The organic solvent can be selected from the group consisting of halogenated hydrocarbons (e.g., dichloromethane, chloroform, chloroethane, dichloroethane, trichloroethane), dimethylformamide, dimethylacetamide and any combination thereof, while dichloromethane is preferred. The reaction can be performed under an acidic condition, e.g., in a solution of hydrogen chloride in 1,4-dioxane; or in the presence of a suitable organic acid (e.g., carboxylic acids or halogenated acids, including but not limited to formic acid, fluoroacetic acid, difluoroacetic acid, trifluoroacetic acid, chloroacetic acid, dichloroacetic acid, trichloroacetic acid and combinations thereof, preferably trifluoroacetic acid). The reaction is preferably performed at a suitable temperature. The preferred temperature is room temperature (20-30°

C.). The reaction is preferably performed for a suitable period of time, such as 1-5 hours or 6-15 hours, e.g., 2 hours, 4 hours or overnight.

Step C-1: Reacting Compound IN-4 With Compound IN-a to Obtain Compound IN-5

In some embodiments, compound IN-5 can be obtained through a substitution reaction of compound IN-4 with compound IN-1. The substitution reaction is preferably performed in a suitable organic solvent. The organic solvent can be selected from the group consisting of dimethylformamide, dimethylacetamide, tetrahydrofuran, N-methylpyrrolidone, dimethyl sulfoxide and any combination thereof, while dimethylformamide or dimethylacetamide is preferred. The substitution reaction is preferably performed in the presence of a suitable base. Preferably, the base is an organic base (e.g., organic amines such as triethylamine, N,N-diisopropylethylamine, N-methylmorpholine or pyridine, preferably triethylamine or N,N-diisopropylethylamine) or an inorganic base (e.g., an alkali metal salt, preferably potassium carbonate). The substitution reaction is preferably performed at a suitable temperature. The temperature can be 20-150° C., e.g., 30-140° C., preferably 25° C., 50° C., 100° C. or 130° C., preferably 80° C. The substitution reaction is preferably performed for a suitable period of time, e.g., 2-24 hours, 2-18 hours or 2-12 hours, e.g., 5, 8 or 10 hours.

In other embodiments, compound IN-5 can be obtained through a coupling reaction of compound IN-4 with compound IN-a. The coupling reaction is preferably performed in the presence of a metal catalyst and a base. Preferably, the metal catalyst is a palladium metal catalyst, such as tris (dibenzylideneacetone)dipalladium, [1,1'-bis(diphenylphosphino)ferrocene]dichloropalladium, triphenylphosphinepalladium, palladium acetate, preferably tris (dibenzylideneacetone)dipalladium. The base is an inorganic base, such as potassium carbonate, cesium carbonate, sodium carbonate, sodium bicarbonate, potassium bicarbonate, preferably cesium carbonate. Preferably, the coupling reaction is performed in the presence of an organic phosphorus compound derived from biphenyl, which is selected from the group consisting of BINAP, RuPhos and XPhos, while BINAP is preferred. Preferably, the coupling reaction is performed in a suitable organic solvent, which can be selected from the group consisting of benzene, toluene and xylene, e.g., toluene. Preferably, the coupling reaction is performed under a suitable protective atmosphere (e.g., a nitrogen atmosphere). Preferably, the coupling reaction is performed at a suitable temperature, which can be 70-100° C., preferably 80° C. Preferably, the coupling reaction is performed for a suitable period of time, such as 1-3 hours, e.g., 2 hours.

Step D-1: Reacting Compound IN-5 With Compound IN-b to Obtain Compound IN-6

Preferably, compound IN-6 can be obtained through a metal-catalyzed coupling reaction of compound IN-5 with compound IN-b. The metal-catalyzed coupling reaction is performed by a conventional method. For example: compound IN-5 and compound IN-b are dissolved in a solvent (e.g., water, an organic solvent, or a mixed solvent of an organic solvent and water), a palladium catalyst and base were added, and the reaction was performed optionally under the protection of nitrogen, at a temperature between 50° C. to 120° C. (preferably 80° C. or 90° C.) for 8 to 24 hours (preferably 8 hours or 12 hours). The organic solvent is dimethylformamide, tetrahydrofuran, 1,4-dioxane, toluene or DME, etc. The palladium catalyst is tris(dibenzylideneacetone)dipalladium, [1,1'-bis(diphenylphosphino)ferrocene]dichloropalladium, triphenylphosphinepalladium, palladium acetate, preferably [1,1'-bis(diphenylphosphino) ferrocene]dichloropalladium or tris(dibenzylideneacetone) dipalladium, etc. The base preferably is an inorganic base, such as potassium carbonate, cesium carbonate, sodium carbonate, sodium bicarbonate or potassium bicarbonate, etc.

Step E-1: Removing the PG$^2$ Group in Compound IN-6 to Obtain the Compound of General Formula (I)

The reaction is preferably performed in a suitable organic solvent (the organic solvent can be selected from the group consisting of linear or cyclic ethers (e.g., tetrahydrofuran or diethyl ether, etc.), N-methylpyrrolidone, dimethylformamide, dimethylacetamide, 1,4-dioxane, dimethyl sulfoxide and any combination thereof, while tetrahydrofuran is preferred). The reaction is preferably performed in the presence of an alcohol or water and a base. The alcohol may be, e.g., methanol or ethanol. The base may be selected from the group consisting of alkali metal hydroxides, which may be selected from the group consisting of lithium hydroxide, sodium hydroxide and potassium hydroxide. The reaction is preferably performed at a suitable temperature. The temperature can be room temperature to 80° C., e.g., 25° C. or 40-60° C. The reaction is preferably performed for a suitable period of time, e.g., 2-5 hours or 6-15 hours, e.g., 2, 3 or 4 hours or overnight. In other embodiments, the present invention provides a method for preparing the compound of general formula al of the present invention, wherein the method comprises the following steps:

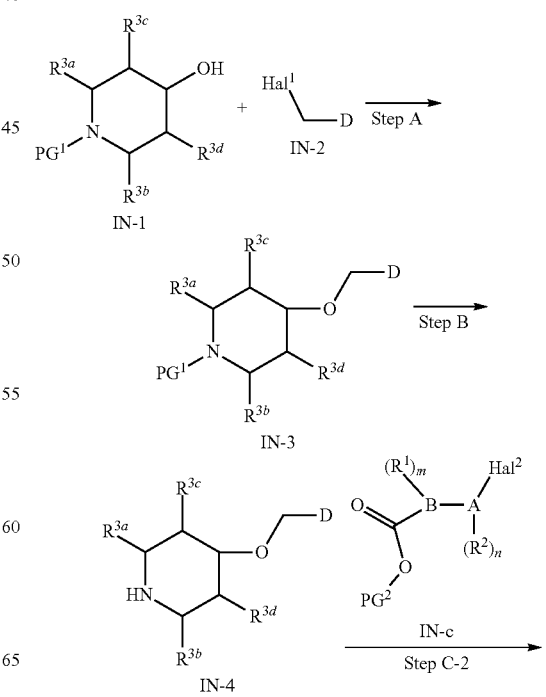

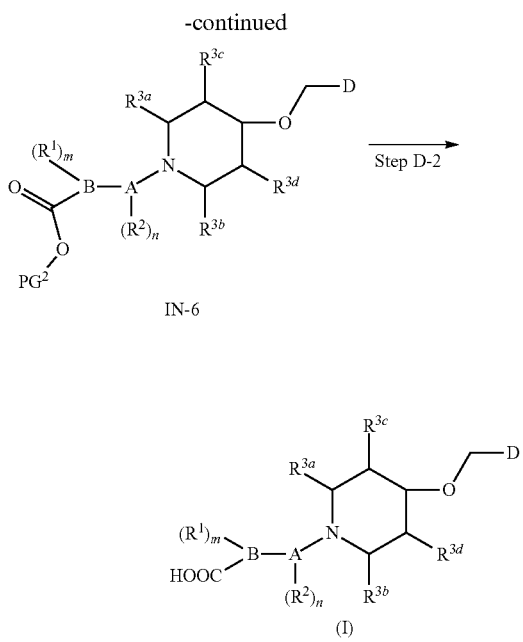

wherein each of the groups is as defined above;
the reaction conditions for each step are as follows:

Step A: Reacting Compound IN-1 With Compound IN-2 to Obtain Compound IN-3

The reaction is preferably performed in a suitable organic solvent. The organic solvent can be selected from the group consisting of linear or cyclic ethers (e.g., tetrahydrofuran or diethyl ether, etc.), N-methylpyrrolidone, dimethylformamide, dimethylacetamide, 1,4-dioxane, dimethyl sulfoxide and any combination thereof, while tetrahydrofuran or dimethylformamide is preferred. The reaction is preferably performed in the presence of a suitable base (e.g., an alkali alkoxide or carbonate) and/or a catalyst. The catalyst can be a catalyst system comprising a crown ether, which can be selected from the group consisting of 15-crown-5 and 18-crown-6; the alkali carbonate is e.g., potassium carbonate or cesium carbonate; the alkali metal alkoxide can be selected from the group consisting of sodium tert-butoxide, potassium tert-butoxide, sodium methoxide, potassium methoxide, sodium ethoxide, potassium ethoxide. Preferably, the alkali metal alkoxide and catalyst are a combination of sodium tert-butoxide and/or potassium tert-butoxide with 15-crown-5 and/or 18-crown-6, preferably a combination of sodium tert-butoxide with 15-crown-5 or a combination of potassium tert-butoxide with 18-crown-6. The reaction is preferably performed at a suitable temperature. The temperature preferably is room temperature (20-30° C.) or 50-100° C. (e.g., 50-80° C.). The reaction is preferably performed for a suitable period of time, such as 1-24 hours, e.g., 5-15 hours.

Step B: Removing the PG$^1$ Group in Compound IN-3 to Obtain Compound IN-4

The reaction is preferably performed in a suitable organic solvent. The organic solvent can be selected from the group consisting of halogenated hydrocarbons (e.g., dichloromethane, chloroform, chloroethane, dichloroethane, trichloroethane), dimethylformamide, dimethylacetamide and any combination thereof, while dichloromethane is preferred. The reaction can be performed under an acidic condition, e.g., in a solution of hydrogen chloride in 1,4-dioxane; or in the presence of a suitable organic acid (e.g., carboxylic acids or halogenated acids, including but not limited to formic acid, fluoroacetic acid, difluoroacetic acid, trifluoroacetic acid, chloroacetic acid, dichloroacetic acid, trichloroacetic acid and combinations thereof, preferably trifluoroacetic acid). The reaction is preferably performed at a suitable temperature. The temperature preferably is room temperature (20-30° C.). The reaction is preferably performed for a suitable period of time, such as 1-5 hours or 6-15 hours, e.g., 2 hours, 4 hours or overnight.

Step C-2: Reacting Compound IN-4 With Compound IN-a to Obtain Compound IN-6

The reaction is preferably performed in the presence of a metal catalyst and a base. Preferably, the metal catalyst is a palladium metal catalyst, such as tris(dibenzylideneacetone)dipalladium, [1,1'-bis(diphenylphosphino)ferrocene]dichloropalladium, triphenylphosphinepalladium, palladium acetate, preferably tris(dibenzylideneacetone)dipalladium. The base is an inorganic base, such as potassium carbonate, cesium carbonate, sodium carbonate, sodium bicarbonate, potassium bicarbonate, preferably cesium carbonate. Preferably, the coupling reaction is performed in the presence of an organic phosphorus compound derived from biphenyl, which is selected from the group consisting of BINAP, RuPhos and XPhos, preferably BINAP. Preferably, the coupling reaction is performed in a suitable organic solvent, which can be selected from the group consisting of benzene, toluene and xylene, e.g., toluene. Optionally, the coupling reaction is performed under a suitable protective atmosphere (e.g., a nitrogen atmosphere). Preferably, the coupling reaction is performed at a suitable temperature, which can be e.g., 50-100° C., preferably 80° C. Preferably, the coupling reaction is performed for a suitable period of time, such as 1-24 hours, e.g., 5-15 hours.

Step D-2: Removing the PG$^2$ Group in Compound IN-6 to Obtain the Compound of General Formula (I)

The reaction is preferably performed in a suitable organic solvent (the organic solvent can be selected from the group consisting of linear or cyclic ethers (e.g., tetrahydrofuran or diethyl ether, etc.), N-methylpyrrolidone, dimethylformamide, dimethylacetamide, 1,4-dioxane, dimethyl sulfoxide and any combination thereof, preferably is tetrahydrofuran). The reaction is preferably performed in the presence of an alcohol and a base. The alcohol may be, e.g., methanol or ethanol. The base may be selected from the group consisting of alkali metal hydroxides, which may be selected from the group consisting of lithium hydroxide, sodium hydroxide and potassium hydroxide. The reaction is preferably performed at a suitable temperature. The temperature can be room temperature to 80° C., e.g., 40-60° C. The reaction is preferably performed for a suitable period of time, such as 2-5 hours, e.g., 2, 3 or 4 hours.

In other embodiments, the present invention provides a compound of general formula (IN-6) or a pharmaceutically acceptable salt thereof,

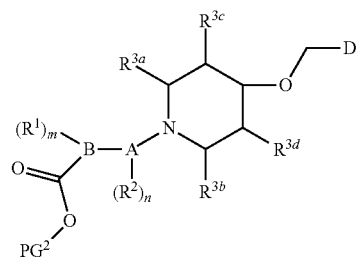
IN-6
wherein each of the groups is as defined above;
the compound is preferably selected from the group consisting of:
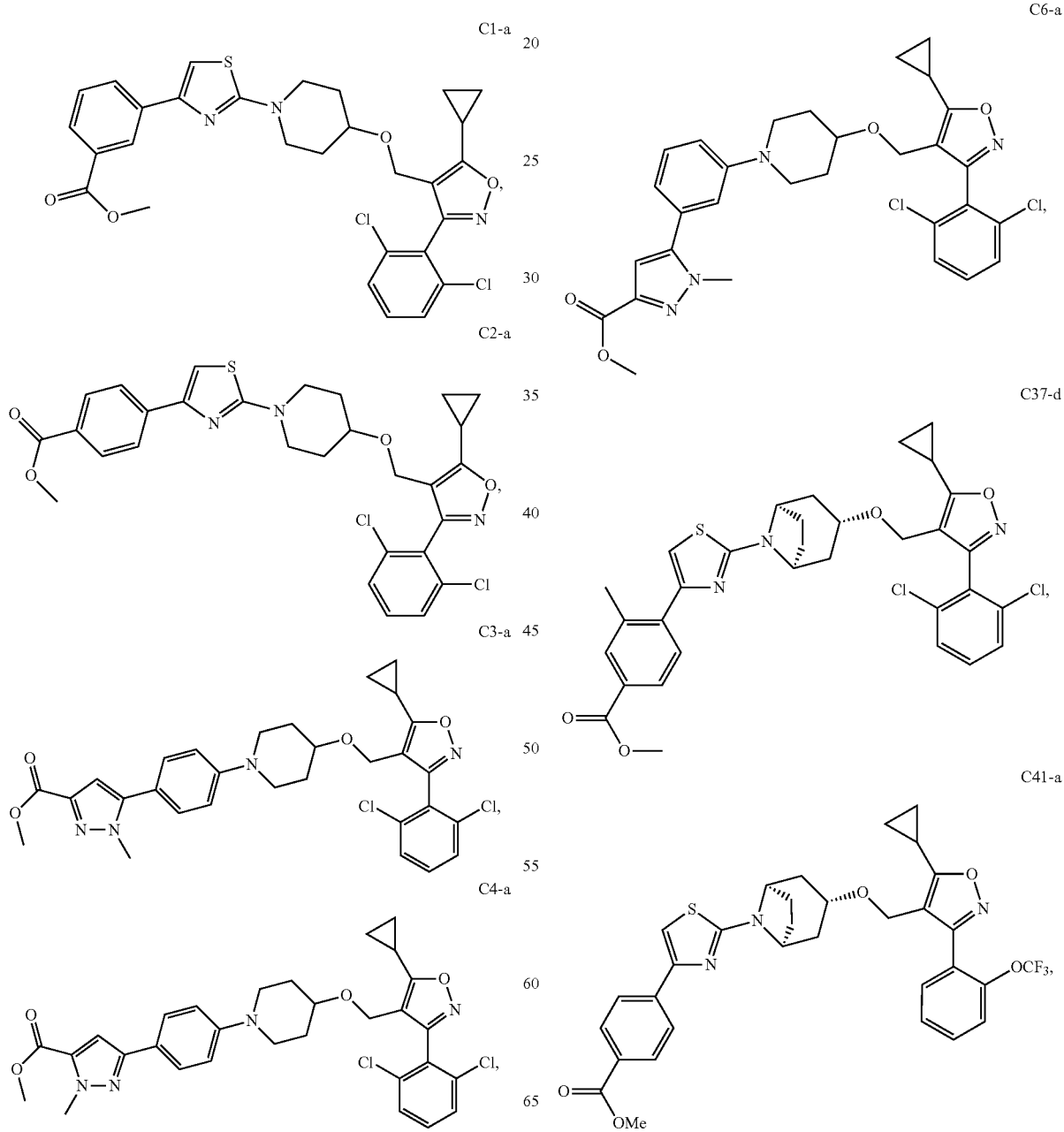

-continued
C42-a
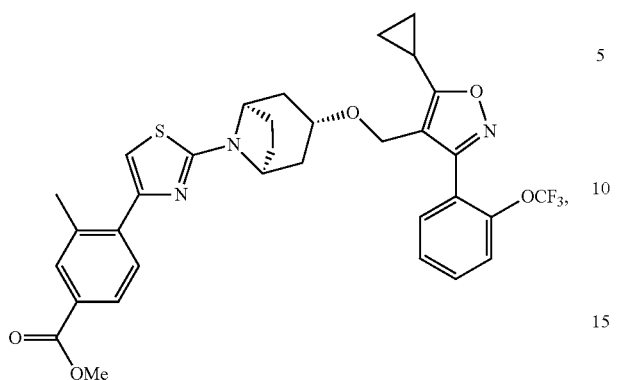
C43-a
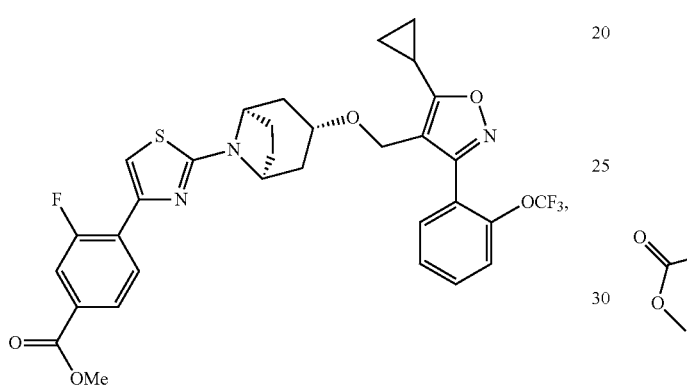
C44-a
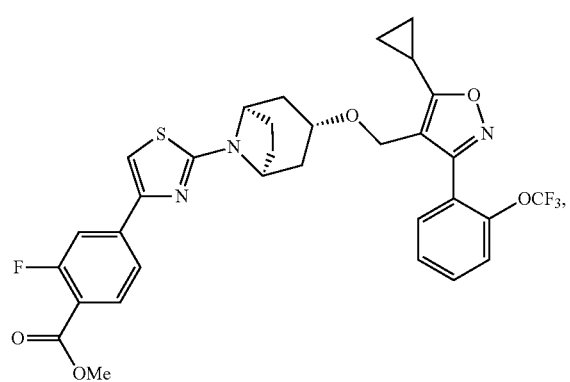
C45-a
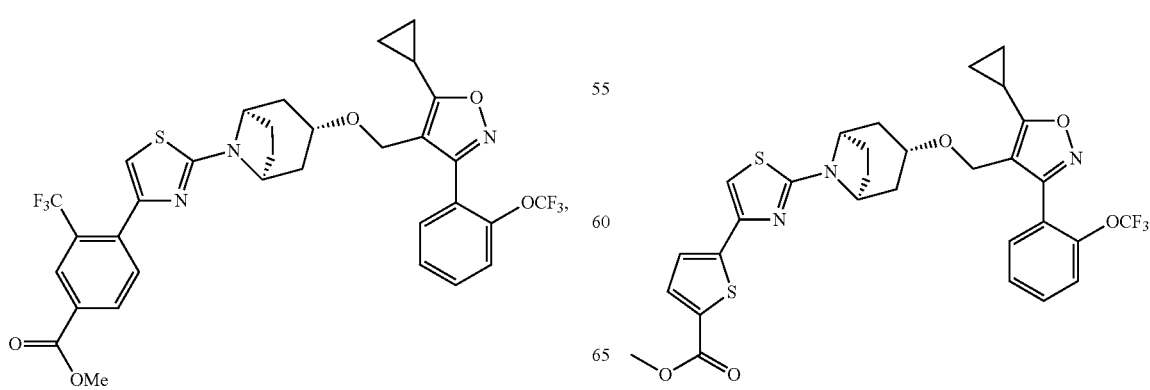
-continued
C46-a
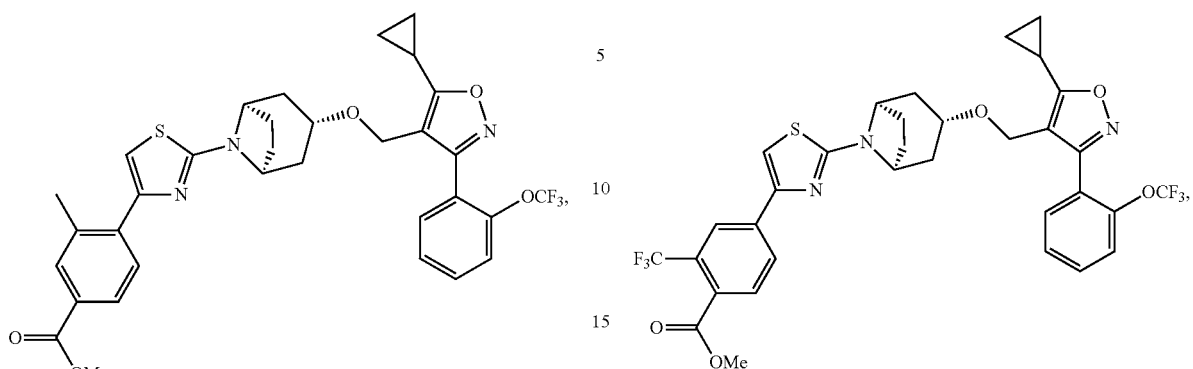
C47-a
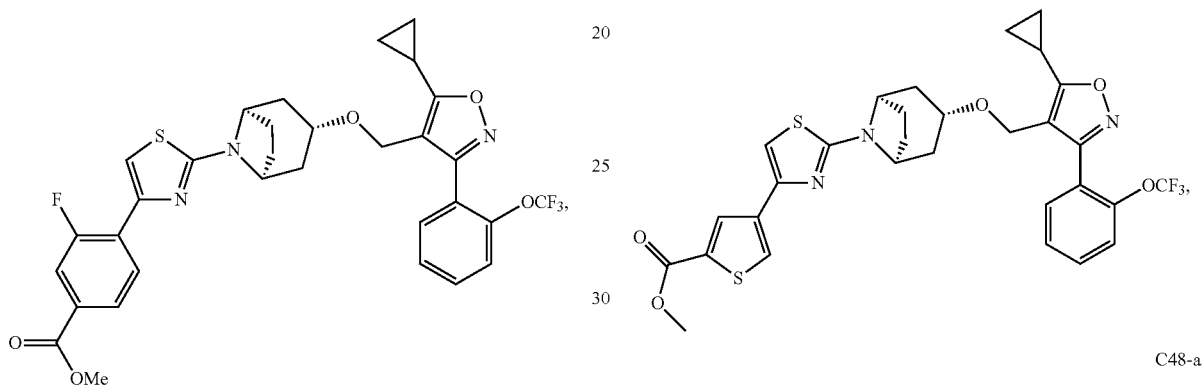
C48-a
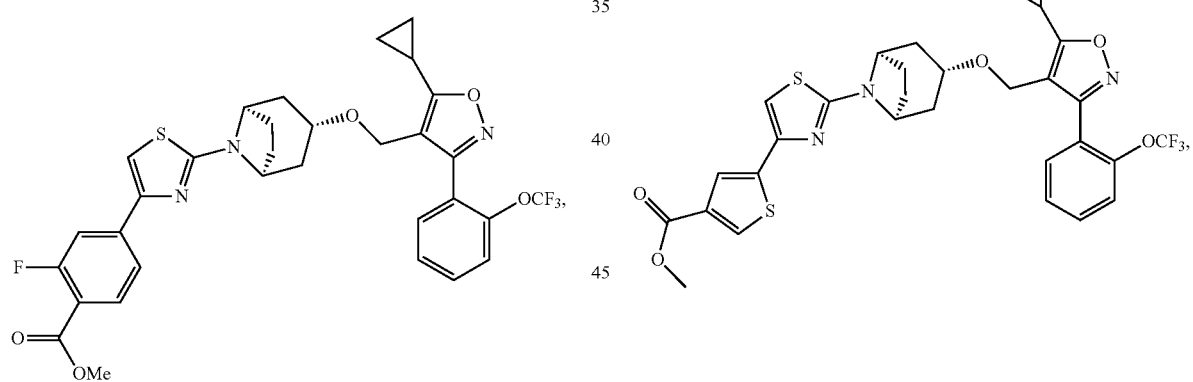
C35-a
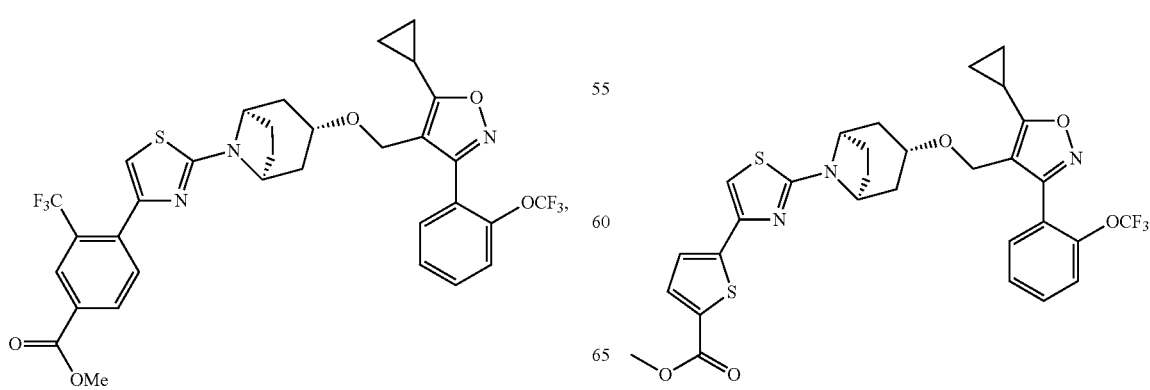
and -continued

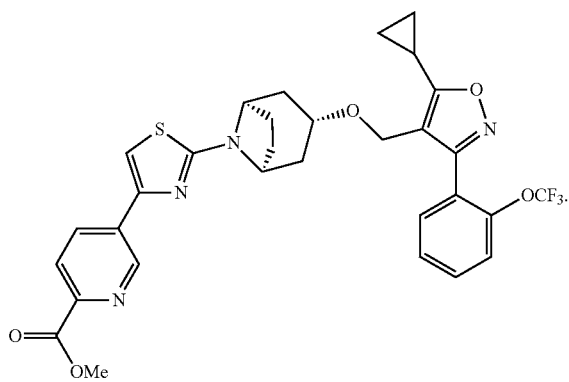

C50-a

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, and whether or not the reaction should be performed under an anhydrous or inert atmosphere, etc. can be varied to optimize the yield of the desired product and it is within their skill to do so.

The Examples provide exemplary methods for preparing the compound of general formula (I). Those skilled in the art will appreciate that other synthetic routes may be used to synthesize the compound of general formula (I). Although specific starting materials and reagents are depicted and discussed in the Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing the compound of general formula (I), protection of remote functionality (e.g., carboxyl or amino) of intermediates may be necessary. The need for such protection will vary depending on the nature of the remote functionality and the conditions of the preparation methods. The need for such protection is readily determined by one skilled in the art. For a general description of protecting groups and their use, see T. W. Greene, Protective Groups in Organic Synthesis, John Wiley & Sons, New York, 1991.

EXAMPLES

The present invention is further described with reference to the following examples, which are not provided to limit the scope of the present invention.

The structure of the compound was confirmed by nuclear magnetic resonance spectrum ($^1$H NMR) or mass spectrum (MS). $^1$H-NMR chemical shifts (δ) are expressed in parts per million (ppm). Chemical shifts are expressed in $10^{-6}$ (ppm).

MS was measured using an Agilent (ESI) mass spectrometer.

Preparative high-performance liquid chromatography was conducted on Shimadzu preparative high performance liquid chromatograph.

Thin layer chromatography (TLC) was performed with an aluminum plate (20×20 cm) produced by Merck, and thin-layer chromatography separation and purification employed GF 254 (0.4-0.5 mm).

The reaction was monitored by thin layer chromatography (TLC) or LC-MS, and the developing solvent system included dichloromethane and methanol system, n-hexane and ethyl acetate system, or petroleum ether and ethyl acetate system. It was necessary to adjust the volume ratio of the solvents, or to further add triethylamine, etc. according to the polarity of the compound, in order to achieve the separation and purification of the product.

Microwave reactions were conducted using the Biotage® Initiator+ (400 W, RT~300° C.) microwave reactor.

Silica gel (200~300 mesh) was normally employed as a stationary phase in column chromatography. The eluent system included dichloromethane and methanol system, and n-hexane and ethyl acetate system. The volume ratio of the solvents was adjusted according to the polarity of the compound; and adjustment by adding a minor amount of triethylamine can be performed.

In the following examples, the reaction temperature was room temperature (20° C.~30° C.), unless otherwise specified.

The reagents used in this application were purchased from Acros Organics, Aldrich Chemical Company or Shanghai Topbiochem LTD. etc.

In the conventional synthetic methods as well as examples and intermediate preparation examples, abbreviations respectively have the following meanings.

| Abbreviation | Meaning | Abbreviation | Meaning |
|---|---|---|---|
| TLC | Thin layer chromatography | LC-MS | liquid chromatograph-mass spectrometer |
| Boc | tert-butyloxycarbonyl | BINAP | (±)-2,2'-bis(diphenylphosphino)-1,1'-binaphthalene |
| Pd(dppf)Cl$_2$ | [1,1'-bis(diphenylphosphino)ferrocene]dichloropalladium | Pd$_2$(dba)$_3$ | tris(dibenzylidene-acetone)dipalladium |
| DMF | N,N-dimethylformamide | DME | dimethoxyethane |

Intermediate Preparation Examples

Intermediate Preparation Example 1: Preparation of 4-(((1-(4-bromothiazol-2-yl)piperidin-4-yl)oxy)methyl)-5-cyclopropyl-3-(2,6-dichlorophenyl)isoxazole (T1)

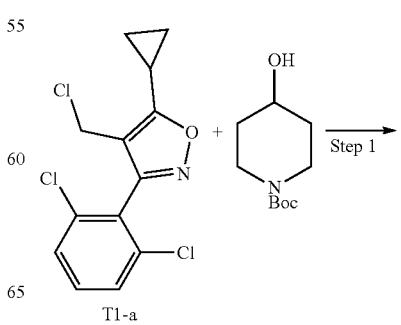

T1-a

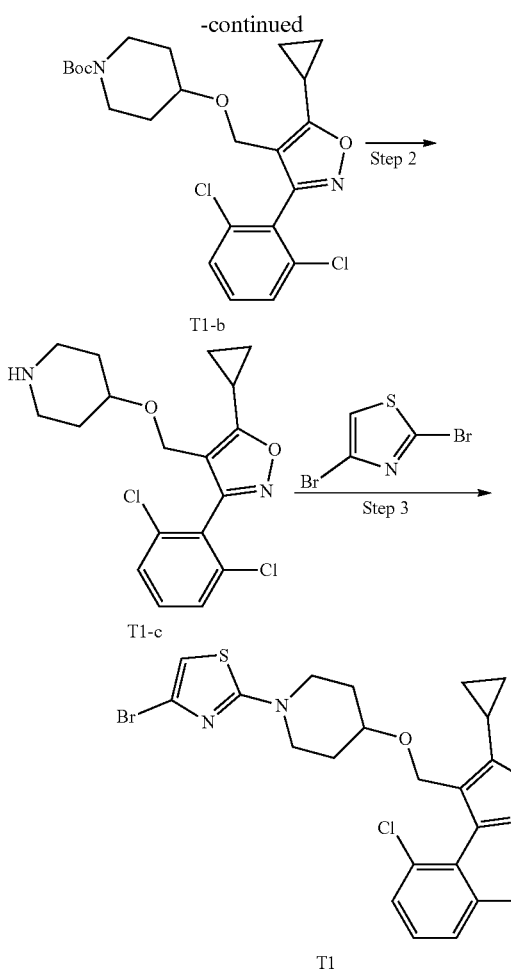

saturated sodium carbonate, and extracted with ethyl acetate. The organic phase was washed with water, dried and concentrated to afford the title compound of this step, which was used directly in the next step without purification.

Step 3: Preparation of 4-(((1-(4-bromothiazol-2-yl)piperidin-4-yl)oxy)methyl)-5-cyclopropyl-3-(2,6-dichlorophenyl)isoxazole (T1)

Compound (T1-c) (500 mg, 1.37 mmol) was dissolved in dry DMF (10 mL), and triethylamine (0.4 mL, 3 mmol) and 2,4-dibromothiazole (398 mg, 1.64 mmol) were added. The mixture was stirred at 80° C. overnight until complete reaction of the starting material indicated by TLC. The mixture was added with water and ethyl acetate, the organic phase was washed with water, dried, concentrated, and the residue was purified by column chromatography on silica gel, to afford the title compound (300 mg, yield: 42%).

Intermediate Preparation Example 2: Preparation of methyl 5-(4-bromophenyl)-1-methyl-1H-pyrazole-3-carboxylate (T2-1) and methyl 3-(4-bromophenyl)-1-methyl-1H-pyrazole-5-carboxylate (T2-2)

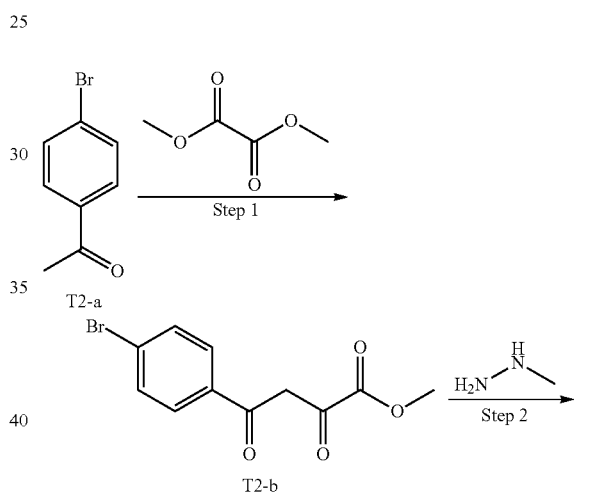

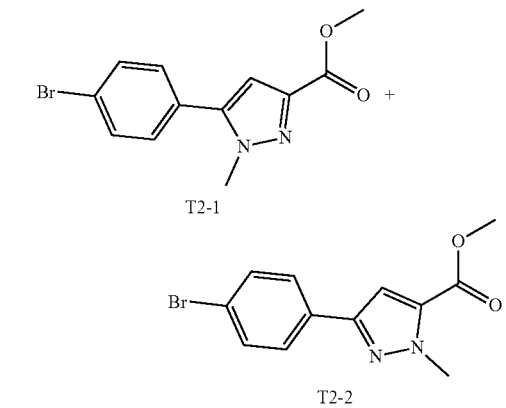

Step 1: Preparation of tert-butyl 4-((5-cyclopropyl-3-(2,6-dichlorophenyl)isoxazol-4-yl)methoxy)piperidine-1-carboxylate (T1-b)

N-Boc-4-hydroxypiperidine (1.0 g, 4.95 mmol) was dissolved in dry tetrahydrofuran (20 mL), potassium tert-butoxide (0.54 g, 5.61 mmol) was added, the reaction was stirred for 30 minutes, and 18-crown-6 (1.5 g, 5.61 mmol) and 4-(chloromethyl)-5-cyclopropyl-3-(2,6-dichlorophenyl)isoxazole (T1-a) (1.0 g, 3.31 mmol) were added. The reaction was stirred at room temperature overnight until complete reaction of the starting material indicated by TLC. The mixture was added with water and ethyl acetate. The organic phase was washed with water, dried, concentrated, and the residue was purified by column chromatography on silica gel, to afford the title compound of this step (1.2 g, yield: 78%).

Step 2: Preparation of 5-cyclopropyl-3-(2,6-dichlorophenyl)-4-((piperidin-4-yloxy)methyl)isoxazole (T1-c)

Compound (T1-b) (1.1 g, 2.36 mmol) was dissolved in dichloromethane (20 mL), and trifluoroacetic acid (5 mL) was added. The reaction was stirred at room temperature for 2 hours until complete reaction of the starting material indicated by TLC. The mixture was concentrated, and the residue was poured to ice water, adjusted to a basic pH with Step 1: Preparation of methyl 4-(4-bromophenyl)-2,4-dioxobutanoate (T2-b)

1-(4-bromophenyl)ethanone (T2-a) (1.0 g, 5 mmol) was dissolved in dry tetrahydrofuran (20 mL), sodium hydride (0.24 g, 6 mmol) was added, the reaction was stirred for 30 minutes, and dimethyl oxalate (0.65 g, 5.5 mmol) was added. The reaction was stirred at 70° C. overnight, and cooled. The mixture was added with water and ethyl acetate, the organic phase was washed with water, dried, concentrated, and the residue was purified by column chromatography on silica gel, to afford the title compound of this step (1.2 g, yield: 86%).

Step 2: Preparation of methyl 5-(4-bromophenyl)-1-methyl-1H-pyrazole-3-carboxylate (T2-1) and methyl 3-(4-bromophenyl)-1-methyl-1H-pyrazole-5-carboxylate (T2-2)

Compound (T2-b) (1.4 g, 4.93 mmol) was dissolved in ethanol (30 mL), and methylhydrazine (5 mL) was added. The reaction was stirred at 80° C. overnight, until complete reaction of the starting material indicated by TLC. The mixture was cooled, and then added with water and ethyl acetate. The organic phase was washed with water, dried, concentrated, and the residue was purified by column chromatography on silica gel, to afford compound (T2-1) (300 mg, yield: 20%) and compound (T2-2) (250 mg, yield: 17%).

Intermediate Preparation Example 3: Preparation of methyl 5-(3-bromophenyl)-1-methyl-1H-pyrazole-3-carboxylate (T3-1) and methyl 3-(3-bromophenyl)-1-methyl-1H-pyrazole-5-carboxylate (T3-2)

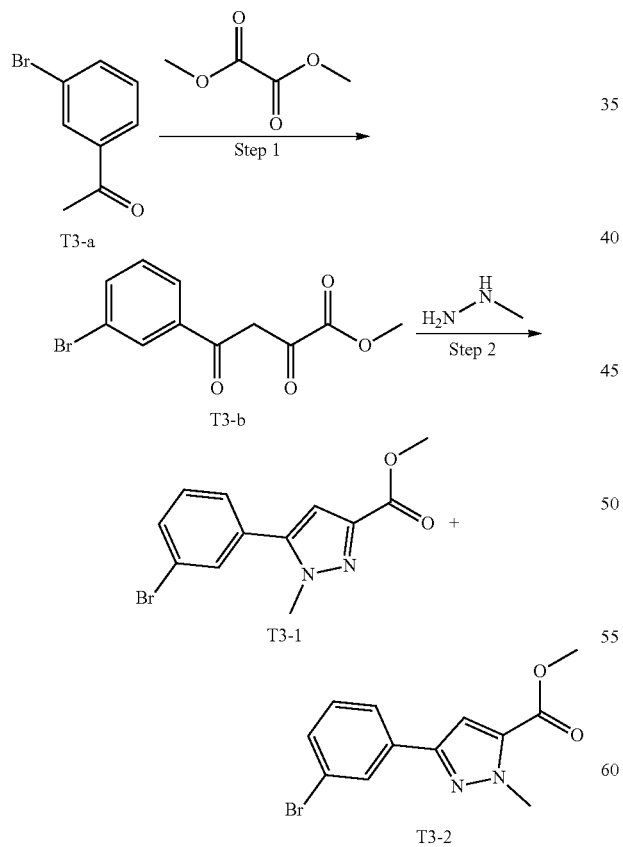

Compound (T3-1) (200 mg, yield: 13%) and compound (T3-2) (230 mg, yield: 15%) were synthesized according to the method described in Intermediate preparation example 2, except that compound (T2-a) was replaced with 1-(3-bromophenyl)ethanone (T3-a) in step 1.

Intermediate Preparation Example 4: Preparation of 4-((((1R,3r,5S)-8-(4-bromothiazol-2-yl)-8-azabicyclo[3.2.1]octan-3-yl)oxy)methyl)-5-cyclopropyl-3-(2-(trifluoromethoxy)phenyl)isoxazole (T4)

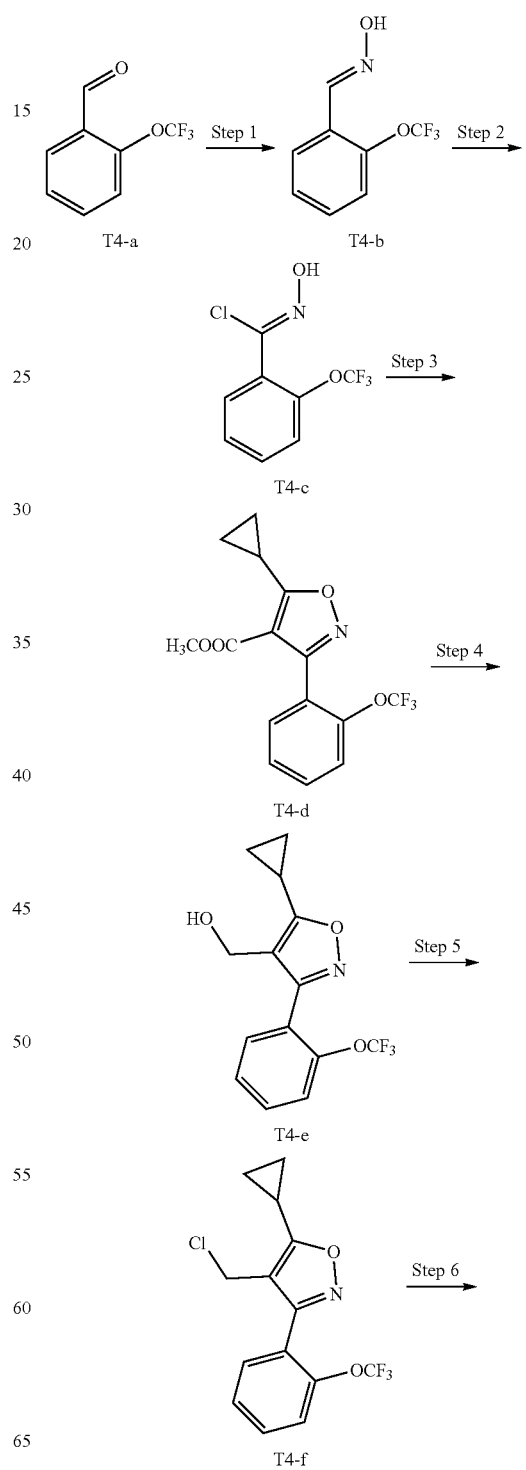

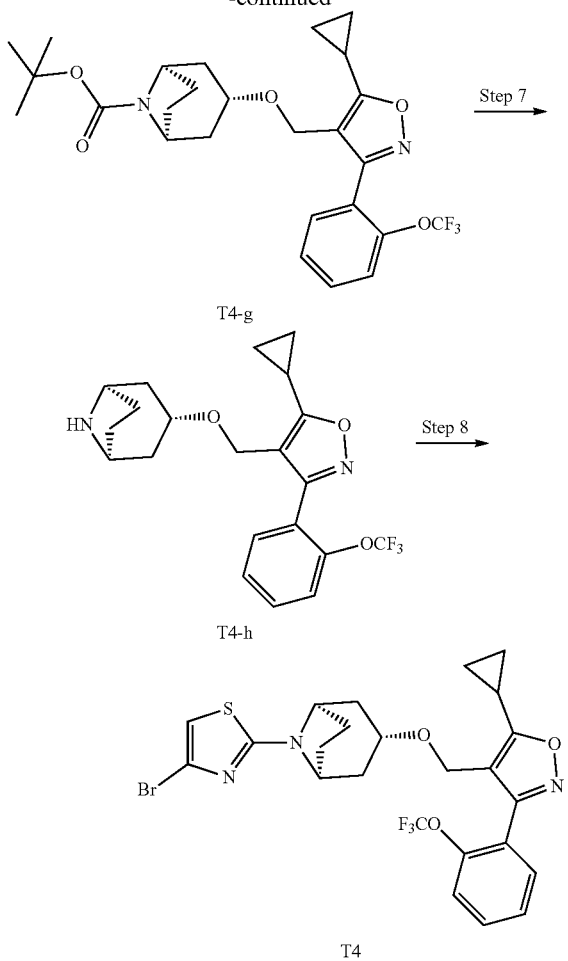

Step 3: Preparation of methyl 5-cyclopropyl-3-(2-(trifluoromethoxy)phenyl)isoxazole-4-carboxylate (T4-d)

Methyl 3-cyclopropyl-3-oxopropanoate (189.87 g, 1.34 mol) was added to compound (T4-c) (160 g, 667.84 mmol), the reaction was stirred at −5° C., triethylamine (500 mL) was added dropwise, and the reaction was performed at −5° C. overnight. The reaction solution was poured into water (20 L), and mechanically stirred for 30 minutes, to result in a solid. A yellow solid was obtained by suction filtration, and dried at 50° C. overnight, to afford compound (T4-d) (120 g, yield: 55%).

Step 4: Preparation of (5-cyclopropyl-3-(2-(trifluoromethoxy)phenyl)isoxazol-4-yl)methanol (T4-e)

Compound (T4-d) (120 g, 366.69 mmol) was dissolved in toluene, the reaction was stirred at −10° C., 2M diisobutylaluminum hydride (550 mL, 1.10 mol) was added dropwise, and the reaction was performed at room temperature overnight. The reaction solution was poured into methanol (1000 mL) with ice, water (3000 mL) was added under mechanical stirring, and suction filtration was performed to obtain a yellow solid. The filtrate was extracted with ethyl acetate (2000 mL×3), dried over anhydrous sodium sulfate (500 g), filtered, and the organic phase was rotary evaporated to dryness to afford compound (T4-e) (100 g, yield: 91%).

Step 5: Preparation of 4-(chloromethyl)-5-cyclopropyl-3-(2-(trifluoromethoxy)phenyl)isoxazole (T4-f)

Benzotriazole (59.65 g, 500.74 mmol) was dissolved in dichloromethane, the reaction was stirred at −5° C., and thionyl chloride (59.65 g, 501.39 mmol) was added dropwise. After the reaction was stirred at room temperature for half an hour, a dichloromethane solution (500 mL) of compound (T4-e) (100 g, 334.17 mmol) was added, and the reaction was performed at room temperature for 6 hours. The reaction solution was filtered with suction, and the filtrate was rotary evaporated to dryness to afford compound (T4-f) (106 g, yield: 94%).

Step 6: Preparation of tert-butyl (1R,3r,5S)-3-((5-cyclopropyl-3-(2-(trifluoromethoxy)phenyl)isoxazol-4-yl)methoxy)-8-azabicyclo[3.2.1]octane-8-carboxylate (T4-g)

Compound (T4-f) (74.77 g, 328.94 mmol) was dissolved in tetrahydrofuran (500 mL), followed by addition of 18-crown-6 (118.56 g, 448.55 mmol). The reaction was stirred at 0° C., potassium tert-butoxide (50.33 g, 448.55 mmol) was added, and then the reaction was stirred at room temperature. Tert-butyl (1R,3r,5S)-3-hydroxy-8-azabicyclo[3.2.1]octane-8-carboxylate (95 g, 299.03 mmol) was added, and the reaction was performed at room temperature overnight. The reaction solution was rotary evaporated to dryness, the residue was added with ethyl acetate (1500 mL) and water (1500 mL), the organic phase was washed twice with saturated brine (1500 mL), concentrated and purified by column chromatography on silica gel (eluent: petroleum ether/ethyl acetate=10/1–5/1), to afford compound (T4-g) (85 g, yield: 56%).

Step 7: Preparation of 4-(((1R,3r,5S)-8-azabicyclo[3.2.1]octan-3-yloxy)methyl)-5-cyclopropyl-3-(2-(trifluoromethoxy)phenyl)isoxazole (T4-h)

Compound (T4-g) (85 g, 167.15 mmol) was dissolved in a solution of dichloromethane (500 mL), followed by addi-

Step 1: Preparation of (E)-2-(trifluoromethoxy)benzaldehyde oxime (T4-b)

2-(trifluoromethoxy)benzaldehyde (T4-a) (150 g, 788.98 mmol) was dissolved in a mixed solvent of ethanol (1000 mL) and water (1000 mL), hydroxylamine hydrochloride (65.79 g, 946.77 mmol) was added under mechanical stirring, a white solid was precipitated, and a 1 M aqueous solution of sodium hydroxide (789 mL, 788.98 mmol) was further added. The reaction was performed at 25° C. for 2 hours. The mixture was added with 1 M hydrochloric acid (2000 mL) to adjust the pH of the system to about 5, and filtered with suction directly. The solid was dried at 50° C. overnight, to afford compound (T4-b) (150 g, yield: 92%).

Step 2: Preparation of (Z)-N-hydroxy-2-(trifluoromethoxy)benzimidoyl chloride (T4-c)

Compound (T4-b) (150 g, 731.23 mmol) was dissolved in DMF (1000 mL), N-chlorosuccinimide (117.17 g, 877.48 mmol) was added at 0° C. under mechanical stirring, and the reaction was performed at 0° C. for 1 hour. The reactants were added with water (2000 mL), and extracted with ethyl acetate (1000 mL×3). The organic layer was dried over anhydrous sodium sulfate (500 g), filtered and concentrated to afford compound (T4-c) (160 g, yield: 91%).

tion of a dioxane solution of hydrochloric acid (4 M, 500 mL). The reaction was performed at room temperature overnight. The reaction solution was rotary evaporated to dryness to afford compound (T4-h) (60 g, yield: 81%).

Step 8: Preparation of 4-((((1R,3r,5S)-8-(4-bromothiazol-2-yl)-8-azabicyclo[3.2.1]octan-3-yl)oxy)methyl)-5-cyclopropyl-3-(2-(trifluoromethoxy)phenyl)isoxazole (T4)

Compound (T4-h) (7 g, 15.73 mmol) was dissolved in DMF (50 mL), followed by addition of N,N-diisopropylethylamine (10.17 g, 78.67 mmol) and 2,4-dibromothiazole (4.59 g, 18.88 mmol), and the reaction was performed at 100° C. for 12 hours. The reaction solution was added with water (300 mL), extracted with ethyl acetate (1000 mL), dried over anhydrous sodium sulfate (20 g), and filtered. The organic phase, after being concentrated, was purified by column chromatography on silica gel (eluent: petroleum ether/ethyl acetate=10/1–6/1) to afford compound (T4) (2.8 g, yield: 31%).

Example 1: Preparation of 3-(2-(4-((5-cyclopropyl-3-(2,6-dichlorophenyl)isoxazol-4-yl)methoxy)piperidin-1-yl)thiazol-4-yl)benzoic acid (C1)

Step 1: Preparation of methyl 3-(2-(4-((5-cyclopropyl-3-(2,6-dichlorophenyl)isoxazol-4-yl)methoxy)piperidin-1-yl)thiazol-4-yl)benzoate (C1-a)

Compound (T1) (100 mg, 0.19 mmol) and (3-(methoxycarbonyl)phenyl)boronic acid (51 mg, 0.28 mmol) were dissolved in DME (2 mL), a 2N aqueous solution of sodium carbonate (0.14 mL) and Pd(dppf)Cl$_2$ (13.9 mg, 0.019 mmol) were added, and the reaction was performed at 80° C. for 12 hours. The reactants were then added with water, and extracted three times with ethyl acetate. The organic phases were combined, washed with saturated brine, dried over anhydrous sodium sulfate, filtered, and the concentrated residue was purified by column chromatography on silica gel to afford the title compound of this step (50 mg, yield: 45%).

MS m/z (ESI): 584.1 [M+H]$^+$.

$^1$H-NMR (400 MHz, DMSO-d$_6$) δ: 7.97-7.92 (m, 4H), 7.66-7.60 (m, 2H), 7.55-7.47 (m, 1H), 7.41 (s, 1H), 4.33 (s, 2H), 3.89 (s, 3H), 3.50-3.39 (m, 2H), 3.29-3.17 (m, 2H), 2.39-2.32 (m, 2H), 1.78-1.69 (m, 2H), 1.44-1.37 (m, 1H), 1.25-1.23 (m, 1H), 1.19-1.05 (m, 4H).

Step 2: Preparation of 3-(2-(4-((5-cyclopropyl-3-(2,6-dichlorophenyl)isoxazol-4-yl)methoxy)piperidin-1-yl)thiazol-4-yl)benzoic acid (C1)

Compound (C1-a) (20 mg, 0.034 mmol) was dissolved in methanol (2 mL) and tetrahydrofuran (1 mL), an aqueous solution of sodium hydroxide (2.74 mg, 0.068 mmol) was added, and the reaction was performed at room temperature for 2 hours. The organic solvents were then removed, the remaining aqueous phase was adjusted to acidic pH with 2N hydrochloric acid, and then extracted with ethyl acetate. The organic phase was concentrated and purified by preparative thin layer chromatography to afford the title compound (15 mg, yield: 78.9%).

MS m/z (ESI): 570.2 [M+H]$^+$.

$^1$H-NMR (400 MHz, DMSO-d$_6$) δ: 12.91 (s, 1H), 7.97-7.92 (m, 4H), 7.66-7.60 (m, 2H), 7.55-7.47 (m, 1H), 7.41 (s, 1H), 4.33 (s, 2H), 3.50-3.39 (m, 2H), 3.29-3.17 (m, 2H), 2.39-2.32 (m, 2H), 1.78-1.69 (m, 2H), 1.44-1.37 (m, 1H), 1.25-1.23 (m, 1H), 1.19-1.05 (m, 4H).

Example 2: Preparation of 4-(2-(4-((5-cyclopropyl-3-(2,6-dichlorophenyl)isoxazol-4-yl)methoxy)piperidin-1-yl)thiazol-4-yl)benzoic acid (C2)

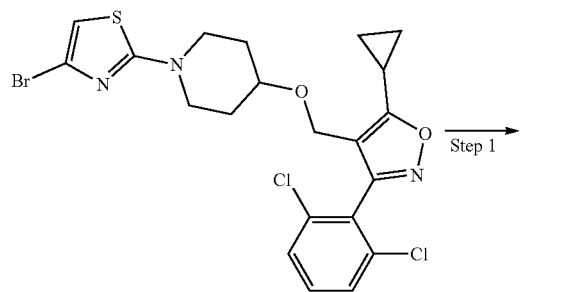

T1

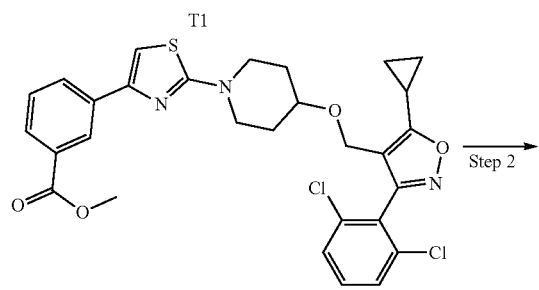

C1-a

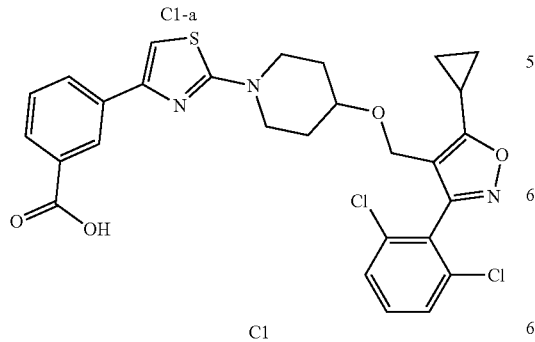

C1

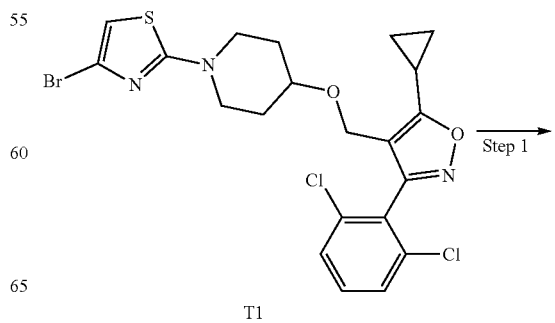

T1

-continued

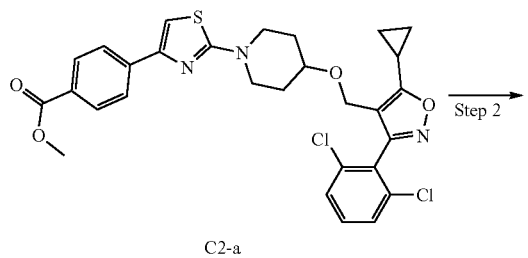

C2-a

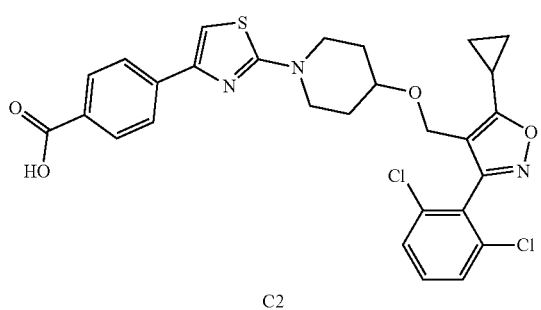

C2

Step 1: Preparation of methyl 4-(2-(4-((5-cyclopropyl-3-(2,6-dichlorophenyl)isoxazol-4-yl)methoxy)piperidin-1-yl)thiazol)-4-yl)benzoate (C2-a)

Compound (C2-a) (45 mg, yield: 40.5%) was synthesized according to the method described in step 1 of Example 1, except that compound (3-(methoxycarbonyl)phenyl)boronic acid was replaced with (4-(methoxycarbonyl)phenyl)boronic acid.

MS m/z (ESI): 584.2 [M+H]$^+$.

$^1$H-NMR (400 MHz, DMSO-d$_6$) δ: 8.39 (s, 1H), 8.05-8.06 (m, 1H), 7.86-7.84 (m, 1H), 7.62-7.60 (m, 2H), 7.54-7.48 (m, 2H), 7.36 (s, 1H), 4.33 (s, 2H), 3.89 (s, 3H), 3.49-3.39 (m, 3H), 3.25-3.19 (m, 2H), 2.39-2.32 (m, 2H), 1.76-1.67 (m, 2H), 1.45-1.35 (m, 1H), 1.16-1.08 (m, 4H).

Step 2: Preparation of 4-(2-(4-((5-cyclopropyl-3-(2,6-dichlorophenyl)isoxazol-4-yl)methoxy)piperidin-1-yl)thiazol-4-yl)benzoic acid (C2)

The title compound (30 mg, yield: 68.5%) was synthesized according to the method described in step 2 of Example 1, except that compound (C1-a) was replaced with compound (C2-a).

MS m/z (ESI): 570.1 [M+H]$^+$.

$^1$H-NMR (400 MHz, DMSO-d$_6$) δ: 13.02 (s, 1H), 8.39 (s, 1H), 8.05-8.06 (m, 1H), 7.86-7.84 (m, 1H), 7.62-7.60 (m, 2H), 7.54-7.48 (m, 2H), 7.36 (s, 1H), 4.33 (s, 2H), 3.49-3.39 (m, 3H), 3.25-3.19 (m, 2H), 2.39-2.32 (m, 2H), 1.76-1.67 (m, 2H), 1.45-1.35 (m, 1H), 1.16-1.08 (m, 4H).

Example 3

Preparation of 5-(4-(4-((5-cyclopropyl-3-(2,6-dichlorophenyl)isoxazol-4-yl)methoxy)piperidin-1-yl)phenyl)-1-methyl-1H-pyrazole-3-carboxylic acid (C3)

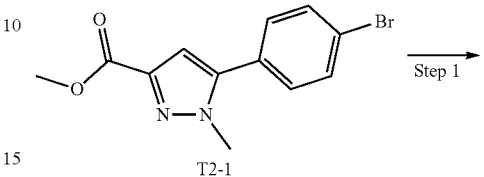

T2-1

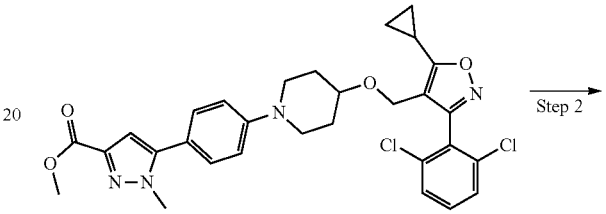

C3-a

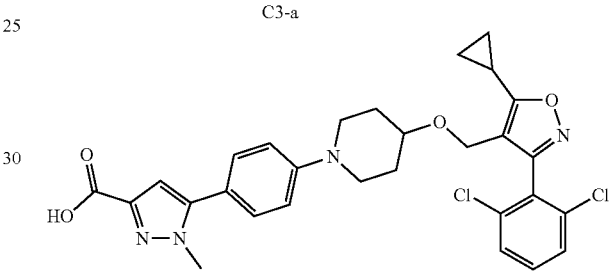

C3

Step 1: Preparation of methyl 5-(4-(4-((5-cyclopropyl-3-(2,6-dichlorophenyl)isoxazol-4-yl)methoxy)piperidin-1-yl)phenyl)-1-methyl-1H-pyrazole-3-carboxylate (C3-a)

Compound (T2-1) (98.8 mg, 0.34 mmol) and compound (T1-c) (103 mg, 0.28 mmol) were dissolved in toluene (2 mL), cesium carbonate (136.9 mg, 0.42 mmol), Pd$_2$(dba)$_3$ (1.61 mg, 0.0028 mmol) and BINAP (1.74 mg, 0.0028 mmol) were added, and the reaction was performed at 80° C. overnight. The reactants were then added with water, and extracted three times with ethyl acetate. The organic phases were combined, washed with saturated brine, dried over anhydrous sodium sulfate, filtered, and concentrated. The residue was purified by column chromatography on silica gel to afford the title compound of this step (15 mg, yield: 9.3%).

MS m/z (ESI): 581.2 [M+H]$^+$.

$^1$H-NMR (400 MHz, DMSO-d$_6$) δ: 7.61-7.58 (m, 4H), 7.53-7.50 (s, 1H), 6.94 (s, 1H), 6.88-6.86 (m, 2H), 4.30 (s, 2H), 4.06 (s, 3H), 3.87 (s, 3H), 3.27-3.23 (m, 3H), 2.84-2.80 (m, 2H), 2.34-2.32 (m, 1H), 1.72-1.68 (m, 2H), 1.35-1.33 (m, 2H), 1.16-1.09 (m, 4H).

Step 2: Preparation of 5-(4-(4-((5-cyclopropyl-3-(2,6-dichlorophenyl)isoxazol-4-yl)methoxy)piperidin-1-yl)phenyl)-1-methyl-1H-pyrazole-3-carboxylic acid (C3)

Compound (C3-a) (15 mg, 0.026 mmol) was dissolved in methanol (1 mL) and tetrahydrofuran (0.5 mL), an aqueous solution of sodium hydroxide (2.07 mg, 0.52 mmol) was added, and the reaction was performed at room temperature for 2 hours. The organic solvents were then removed, the remaining aqueous phase was adjusted to acidic pH with 2 N hydrochloric acid, and then extracted with ethyl acetate. The organic phase was concentrated, and purified on a preparative thin layer chromatography plate to afford the title compound (2 mg, yield: 13.6%).

MS m/z (ESI): 567.1 [M+H]$^+$.

$^1$H-NMR (400 MHz, DMSO-d$_6$) δ: 12.92 (s, 1H), 7.61-7.58 (m, 4H), 7.53-7.50 (s, 1H), 6.94 (s, 1H), 6.88-6.86 (m, 2H), 4.30 (s, 2H), 4.06 (s, 3H), 3.27-3.23 (m, 3H), 2.84-2.80 (m, 2H), 2.34-2.32 (m, 1H), 1.72-1.68 (m, 2H), 1.35-1.33 (m, 2H), 1.16-1.09 (m, 4H).

Example 4: Preparation of 3-(4-(4-((5-cyclopropyl-3-(2,6-dichlorophenyl)isoxazol-4-yl)methoxy)piperidin-1-yl)phenyl)-1-methyl-1H-pyrazole-5-carboxylic acid (C4)

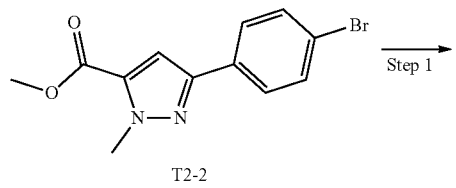

T2-2

Step 1 →

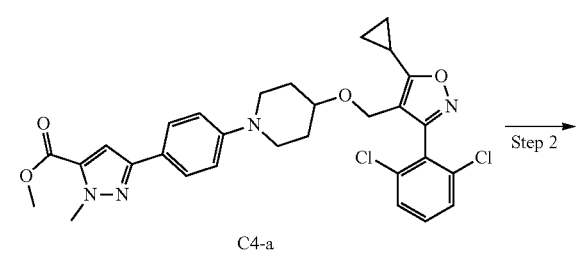

C4-a

Step 2 →

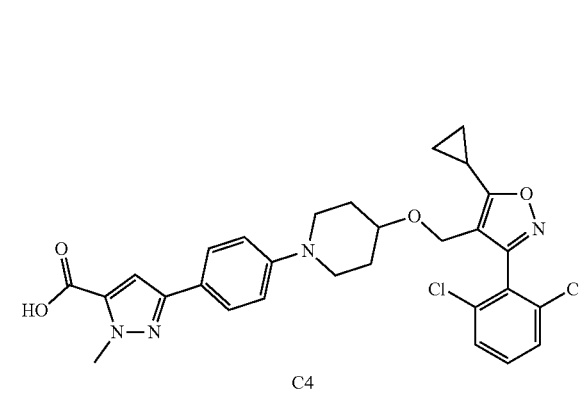

C4

Step 1: Preparation of methyl 3-(4-(4-((5-cyclopropyl-3-(2,6-dichlorophenyl)isoxazol-4-yl)methoxy)piperidin-1-yl)phenyl)-1-methyl-1H-pyrazole-5-carboxylate (C4-a)

The title compound of this step (30 mg, yield: 15.2%) was synthesized according to the method described in step 1 of Example 3, except that compound (T2-1) was replaced with compound (T2-2).

MS m/z (ESI): 581.2 [M+H]$^+$.

$^1$H-NMR (400 MHz, DMSO-d$_6$) δ: 7.62-7.59 (m, 4H), 7.54-7.50 (s, 1H), 6.94 (s, 1H), 6.88-6.86 (m, 2H), 4.31 (s, 2H), 4.11 (s, 3H), 3.87 (s, 3H), 3.27-3.23 (m, 3H), 2.84-2.80 (m, 2H), 2.34-2.32 (m, 1H), 1.72-1.68 (m, 2H), 1.35-1.33 (m, 2H), 1.16-1.09 (m, 4H).

Step 2: Preparation of 3-(4-(4-((5-cyclopropyl-3-(2,6-dichlorophenyl)isoxazol-4-yl)methoxy)piperidin-1-yl)phenyl)-1-methyl-1H-pyrazole-5-carboxylic acid (C4)

The title compound (15 mg, yield: 51%) was synthesized according to the method described in step 2 of Example 3, except that compound (C3-a) was replaced with compound (C4-a).

MS m/z (ESI): 567.1 [M+H]$^+$.

$^1$H-NMR (400 MHz, DMSO-d$_6$) δ: 12.90 (s, 1H), 7.62-7.59 (m, 4H), 7.54-7.50 (s, 1H), 6.94 (s, 1H), 6.88-6.86 (m, 2H), 4.31 (s, 2H), 4.10 (s, 3H), 3.27-3.23 (m, 3H), 2.84-2.80 (m, 2H), 2.34-2.32 (m, 1H), 1.72-1.68 (m, 2H), 1.35-1.33 (m, 2H), 1.16-1.09 (m, 4H).

Example 5: Preparation of 3-(3-(4-((5-cyclopropyl-3-(2,6-dichlorophenyl)isoxazol-4-yl)methoxy)piperidin-1-yl)phenyl)-1-methyl-1H-pyrazole-5-carboxylic acid (C5)

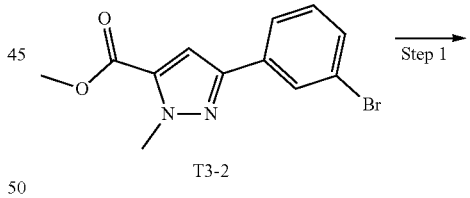

T3-2

Step 1 →

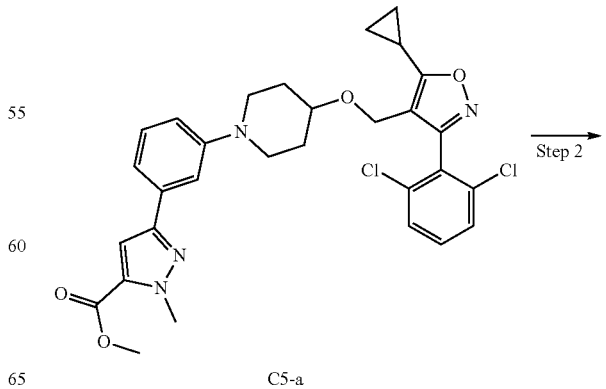

C5-a

Step 2 →

-continued

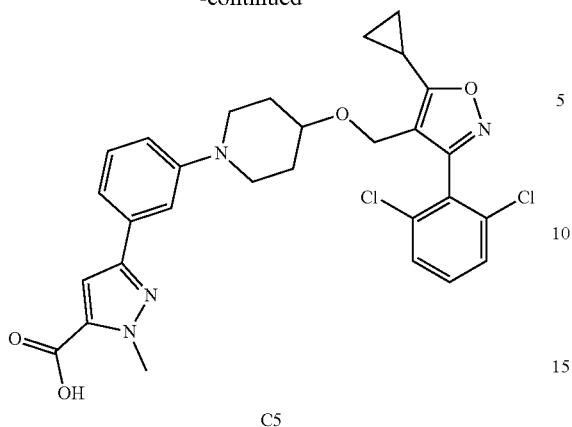

C5

Step 1: Preparation of methyl 3-(3-(4-((5-cyclopropyl-3-(2,6-dichlorophenyl)isoxazol-4-yl)methoxy)piperidin-1-yl)phenyl)-1-methyl-1H-pyrazole-5-carboxylate (C5-a)

The title compound (50 mg, yield: 25.4%) was synthesized according to the method described in step 1 of Example 3, except that compound (T2-1) was replaced with compound (T3-2).

MS m/z (ESI): 581.2 [M+H]$^+$.

$^1$H-NMR (400 MHz, DMSO-d$_6$) δ: 7.62-7.59 (m, 2H), 7.53-7.51 (s, 1H), 7.30-7.26 (m, 2H), 7.21-7.19 (m, 2H), 6.87-6.85 (m, 1H), 4.31 (s, 2H), 4.11 (s, 3H), 3.87 (s, 3H), 3.61-3.58 (m, 1H), 3.29-3.25 (m, 2H), 2.86-2.80 (m, 2H), 2.37-2.31 (m, 1H), 1.77-1.70 (m, 3H), 1.16-1.09 (m, 5H).

Step 2: Preparation of 3-(3-(4-((5-cyclopropyl-3-(2,6-dichlorophenyl)isoxazol-4-yl)methoxy)piperidin-1-yl)phenyl)-1-methyl-1H-pyrazole-5-carboxylic acid (C5)

The title compound (40 mg, yield: 82.1%) was synthesized according to the method described in step 2 of Example 3, except that compound (C3-a) was replaced with compound (C5-a).

MS m/z (ESI): 567.1 [M+H]$^+$.

$^1$H-NMR (400 MHz, DMSO-d$_6$) δ: 12.90 (s, 1H), 7.62-7.59 (m, 2H), 7.53-7.51 (s, 1H), 7.30-7.26 (m, 2H), 7.21-7.19 (m, 2H), 6.87-6.85 (m, 1H), 4.31 (s, 2H), 4.11 (s, 3H), 3.61-3.58 (m, 1H), 3.29-3.25 (m, 2H), 2.86-2.80 (m, 2H), 2.37-2.31 (m, 1H), 1.77-1.70 (m, 3H), 1.16-1.09 (m, 5H).

Example 6: Preparation of 5-(3-(4-((5-cyclopropyl-3-(2,6-dichlorophenyl)isoxazol-4-yl)methoxy)piperidin-1-yl)phenyl)-1-methyl-1H-pyrazole-3-carboxylic acid (C6)

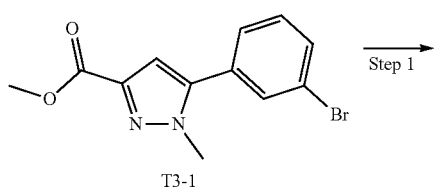

T3-1

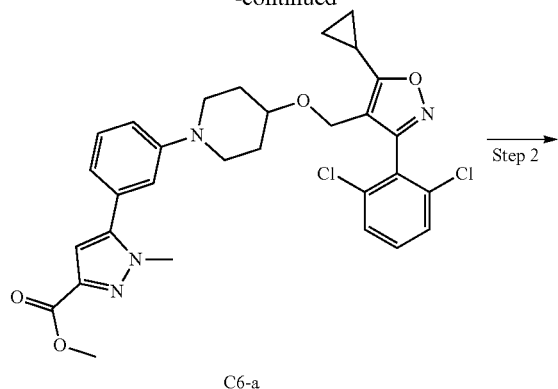

C6-a

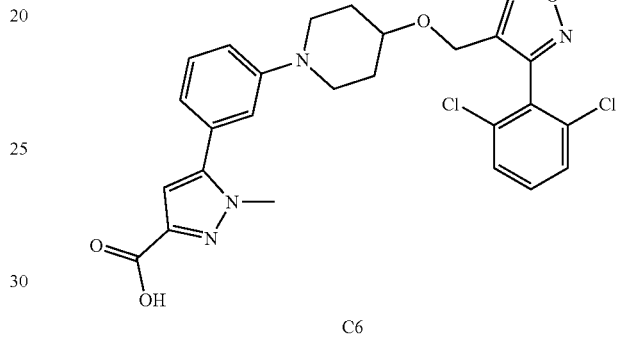

C6

Step 1: Preparation of methyl 5-(3-(4-((5-cyclopropyl-3-(2,6-dichlorophenyl)isoxazol-4-yl)methoxy)piperidin-1-yl)phenyl)-1-methyl-1H-pyrazole-3-carboxylate (C6-a)

The title compound of this step (10 mg, yield: 5.1%) was synthesized according to the method described in step 1 of Example 3, except that compound (T2-1) was replaced with compound (T3-1).

MS m/z (ESI): 581.2 [M+H]$^+$.

$^1$H-NMR (400 MHz, DMSO-d$_6$) δ: 7.63-7.59 (m, 2H), 7.52-7.51 (s, 1H), 7.30-7.26 (m, 2H), 7.21-7.19 (m, 2H), 6.87-6.85 (m, 1H), 4.31 (s, 2H), 4.08 (s, 3H), 3.89 (s, 3H), 3.61-3.58 (m, 1H), 3.29-3.25 (m, 2H), 2.86-2.80 (m, 2H), 2.37-2.31 (m, 1H), 1.77-1.70 (m, 3H), 1.16-1.09 (m, 5H).

Step 2: Preparation of 5-(3-(4-((5-cyclopropyl-3-(2,6-dichlorophenyl)isoxazol-4-yl)methoxy)piperidin-1-yl)phenyl)-1-methyl-1H-pyrazole-3-carboxylic acid (C6)

The title compound (5 mg, yield: 52.1%) was synthesized according to the method described in step 2 of Example 3, except that compound (C3-a) was replaced with compound (C6-a).

MS m/z (ESI): 567.1 [M+H]$^+$.

$^1$H-NMR (400 MHz, DMSO-d$_6$) δ: 12.89 (s, 1H), 7.63-7.59 (m, 2H), 7.52-7.51 (s, 1H), 7.30-7.26 (m, 2H), 7.21-7.19 (m, 2H), 6.87-6.85 (m, 1H), 4.31 (s, 2H), 4.08 (s, 3H), 3.61-3.58 (m, 1H), 3.29-3.25 (m, 2H), 2.86-2.80 (m, 2H), 2.37-2.31 (m, 1H), 1.77-1.70 (m, 3H), 1.16-1.09 (m, 5H).

Example 7: Preparation of 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)-3-methylbenzoic acid (C37)

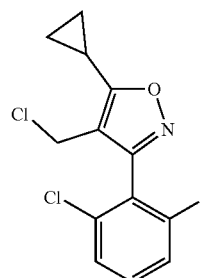

T1-a

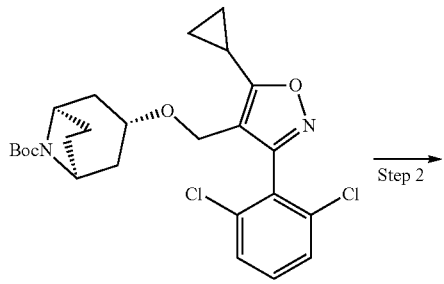

C37-a

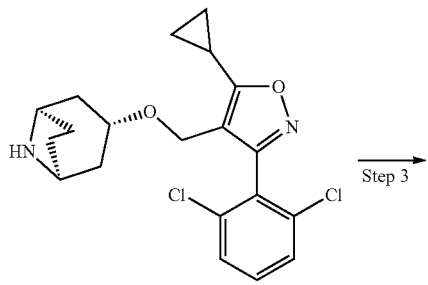

C37-b

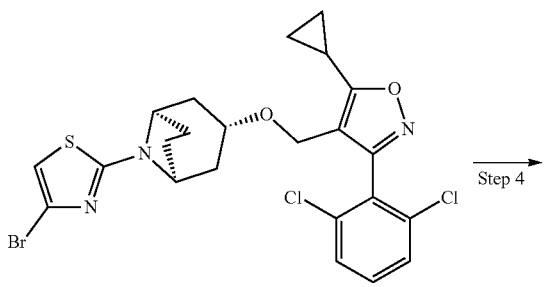

C37-c

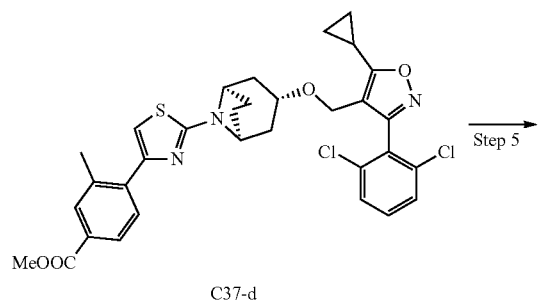

C37-d

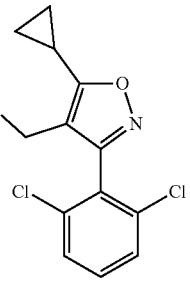

C37-d

Step 1: Preparation of tert-butyl (1R,3r,5S)-3-((5-cyclopropyl-3-(2,6-dichlorophenyl)isoxazol-4-yl)methoxy)-8-azabicyclo[3.2.1]octane-8-carboxylate (C37-a)

At room temperature, compound (T1-a) (1.0 g, 3.33 mmol) was dissolved in DMF (20 mL), after complete dissolution, potassium carbonate (0.919 g, 6.66 mmol) and tert-butyl (1R,3r,5S)-3-hydroxy-8-azabicyclo[3.2.1]octane-8-carboxylate (0.756 g, 3.33 mmol) were added under stirring, and the reaction was stirred at 65° C. overnight after the addition. A large number of white solids were precipitated in the reaction solution, and filtered. The filtrate was sequentially washed with water (50 mL) and a saturated brine solution (50 mL). The organic phase was dried over anhydrous sodium sulfate, evaporated under reduced pressure to remove the solvent, and the residue was purified by column chromatography on silica gel to afford the title compound of this step (1.4 g).
MS m/z (ESI): 494.4 [M+H]$^+$.

Step 2: Preparation of 4-(((1R,3r,5S)-8-azabicyclo[3.2.1]octan-3-yloxy)methyl)-5-cyclopropyl-3-(2,6-dichlorophenyl)isoxazole (C37-b)

Compound (C37-a) (1.4 g, 2.84 mmol) was dissolved in dichloromethane (20 mL), trifluoroacetic acid (5 mL) was added, and the reaction was performed at 30° C. for 4 hours. The reaction was monitored by LC-MS until complete reaction of the starting material, and was stopped. The reaction solution was quenched by adding a saturated aqueous solution of sodium bicarbonate (20 mL), and extracted with dichloromethane (30 mL×3). The organic phase was dried over anhydrous sodium sulfate, evaporated under reduced pressure to remove the solvent, in order to afford a crude product, which was purified by column chromatography on silica gel (eluent: petroleum ether/ethyl acetate=4/1) to afford the title compound of this step (1.01 g).
MS m/z (ESI): 394.3 [M+H]$^+$.

Step 3: Preparation of 4-((((1R,3r,5S)-8-(4-bromothiazol-2-yl)-8-azabicyclo[3.2.1]octan-3-yl)oxy)methyl)-5-cyclopropyl-3-(2,6-dichlorophenyl)isoxazole (C37-c)

At room temperature, compound (C37-b) (1.01 g, 2.57 mmol) was added to DMF (20 mL), then potassium carbonate (710 mg, 5.14 mmol) and 2,4-dibromothiazole (625 mg, 2.57 mmol) were added, and the reaction was performed at 25° C. overnight until complete reaction of the starting material. The reaction solution was added with water (20 mL), and extracted with ethyl acetate (20 mL×3). The combined organic phases were washed with water, dried over anhydrous sodium sulfate, filtered, and the crude product was purified by column chromatography on silica gel (eluent: petroleum ether/ethyl acetate=5/1) to afford the title compound of this step (830 mg).

MS m/z (ESI): 556.3 [M+H]$^+$.

Step 4: Preparation of methyl 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)-3-methylbenzoate (C37-d)

Compound (C37-c) (830 mg, 1.50 mmol) was added to DMF (20 mL), then methyl 3-methyl-4-(4,4,5,5-tetramethyl-1,3,2-dioxaborolan-2-yl)benzoate (414 mg, 1.50 mmol), potassium carbonate (414 mg, 5.14 mmol) and Pd(dppf)Cl$_2$ (163 mg, 0.2 mmol) were added, and the reaction was performed at 90° C. for 12 hours. TLC indicated the reaction was complete. The reaction was extracted with ethyl acetate (30 mL×3), the combined organic phases were washed with water, dried over anhydrous sodium sulfate, filtered, and evaporated under reduced pressure to remove the solvent. The crude product was purified by column chromatography on silica gel (eluent: petroleum ether/ethyl acetate=5/1) to afford the title compound of this step (120 mg).

MS m/z (ESI): 625.6 [M+H]$^+$.

Step 5: Preparation of 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)-3-methylbenzoic acid (C37)

At room temperature, compound (C37-d) (120 mg, 0.19 mmol) was added to tetrahydrofuran (10 mL), water (2.0 mL) and lithium hydroxide (14 mg, 0.51 mmol) were then added, and the reaction was performed at room temperature for 6 hours. The reaction continued overnight until complete reaction of the starting material. The reaction solution was adjusted to pH 5-6 with 1 N hydrochloric acid, added with water (100 mL), and then extracted with ethyl acetate (30 mL×3). The organic phase was dried over anhydrous sodium sulfate, filtered, and evaporated under reduced pressure to remove the solvent. The crude product was purified by column chromatography on silica gel (eluent: petroleum ether/ethyl acetate=2/1) to afford the title compound (20 mg).

MS m/z (ESI): 610.1 [M+H]$^+$.

$^1$H-NMR (400 MHz, CDCl$_3$) δ: 7.90-7.95 (m, 2H), 7.70 (d, J=8.0 Hz, 1H), 7.41-7.36 (m, 3H), 6.59 (s, 1H), 5.30 (s, 2H), 4.26 (s, 2H), 4.16 (s, 2H), 3.52-3.50 (m, 1H), 2.52 (s, 3H), 2.11-2.00 (m, 4H), 1.91-1.68 (m, 6H), 1.25-1.11 (m, 2H).

Example 8: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)benzoic acid (C41)

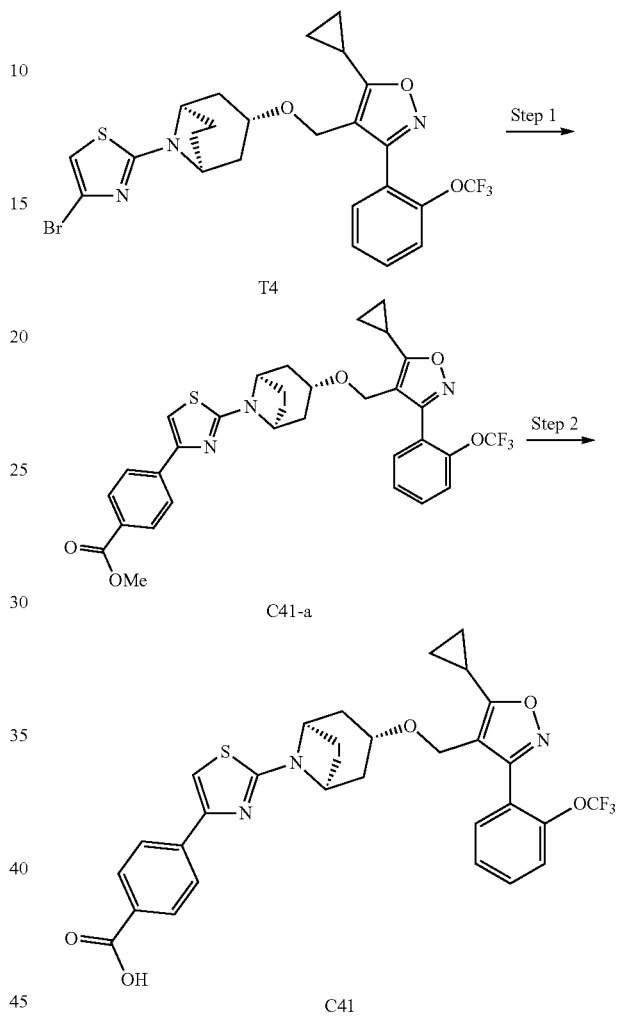

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)benzoate (C41-a)

Compound (T4) (1 g, 1.75 mmol) was dissolved in 1,4-dioxane (20 mL), followed by addition of methyl 4-(4,4,5,5-tetramethyl-1,3,2-dioxaborolan-2-yl)benzoate (532.50 mg, 1.93 mmol), [1,1'-bis(diphenylphosphino)ferrocene]dichloropalladium (143.16 mg, 195.66 μmol) and potassium carbonate (483.85 mg, 3.50 mmol) at room temperature. Replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration.

The resulting residue was purified by column chromatography on silica gel (eluent: petroleum ether/ethyl acetate=10/1–6/1) to afford the title compound of this step (1.12 g).

MS m/z (ESI): 626.1 [M+H]⁺.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)benzoic acid (C41)

Compound (C41-a) (390 mg, 625.31 μmol) was dissolved in tetrahydrofuran (5 mL), an aqueous solution of sodium hydroxide (25.01 mg, 625.31 μmol) (2 mL) was added, and the reaction was performed at 25° C. for 4 hours. The reaction solution was adjusted to pH 4 with 1 M dilute hydrochloric acid, and extracted with ethyl acetate (100 mL×3). The organic phase was dried over anhydrous sodium sulfate, filtered, concentrated, and the resulting residue was purified by column chromatography on silica gel (eluent: petroleum ether/ethyl acetate=10/1–6/1) to afford the title compound (150 mg).

MS m/z (ESI): 612.1 [M+H]⁺.

¹H-NMR (400 MHz, DMSO-d₆) δ: 7.96 (s, 1H), 7.68 (dd, J=18.6, 7.7 Hz, 1H), 7.58 (dd, J=13.9, 6.8 Hz, 1H), 7.45 (s, 1H), 4.36 (s, 1H), 4.15 (s, 1H), 2.36 (s, 1H), 2.04 (d, J=15.2 Hz, 1H), 1.82 (s, 1H), 1.70 (d, J=14.9 Hz, 1H), 1.39-1.26 (m, 1H), 1.13 (d, J=22.2 Hz, 1H).

Example 9: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-methylbenzoic acid (C42)

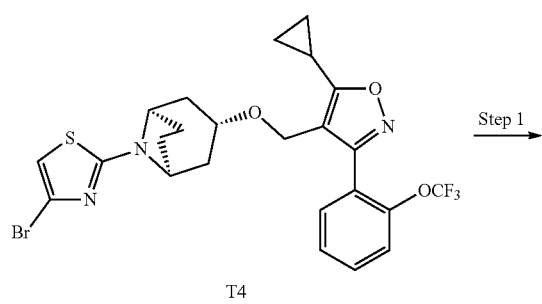

T4

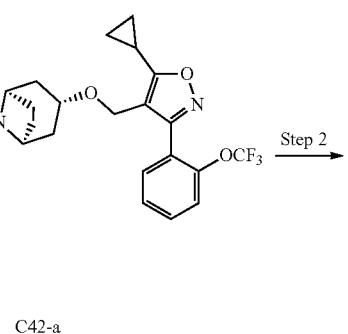

C42-a

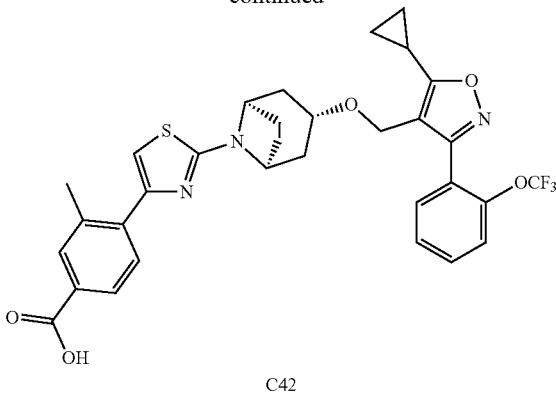

C42

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-methylbenzoate (C42-a)

Compound (T4) (500 mg, 876.55 mmol) was dissolved in 1,4-dioxane (20 mL), followed by addition of methyl 3-methyl-4-(4,4,5,5-tetramethyl-1,3,2-dioxaborolan-2-yl)benzoate (266.25 mg, 964.20 μmol), [1,1'-bis(diphenylphosphino)ferrocene]dichloropalladium (71.58 mg, 97.83 μmol) and potassium carbonate (241.93 mg, 1.75 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g) followed by concentration. The resulting residue was purified by column chromatography on silica gel (eluent: petroleum ether/ethyl acetate=10/1–6/1) to afford the title compound of this step (400 mg).

MS m/z (ESI): 640.2 [M+H]⁺.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-methylbenzoic acid (C42)

Compound (C42-a) (300 mg, 468.98 μmol) was dissolved in tetrahydrofuran (5 mL), an aqueous solution (2 mL) of sodium hydroxide (18.76 mg, 468.98 μmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, filtered, and concentrated. The resulting residue was purified by column chromatography on silica gel (eluent:petroleum ether:ethyl acetate=10:1–6:1) to afford the title compound (280 mg).

MS m/z (ESI): 612.1 [M+H]⁺.

¹H-NMR (400 MHz, DMSO-d₆) δ: 7.84 (s, 1H), 7.80 (d, J=8.1 Hz, 1H), 7.74-7.68 (m, 1H), 7.66 (d, J=6.2 Hz, 1H), 7.58 (dd, J=13.7, 6.4 Hz, 1H), 7.06 (s, 1H), 4.35 (s, 1H), 4.11 (s, 1H), 2.51 (d, J=15.3 Hz, 4H), 2.41-2.32 (m, 1H), 2.04 (d, J=14.7 Hz, 1H), 1.94 (s, 1H), 1.82 (s, 2H), 1.69 (d, J=14.6 Hz, 1H), 1.19-1.14 (m, 2H), 1.10 (m, 2H).

Example 10: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-fluorobenzoic acid (C43)

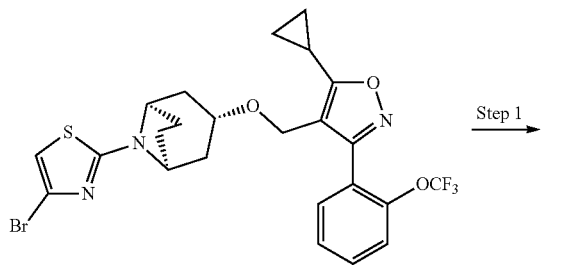

T4

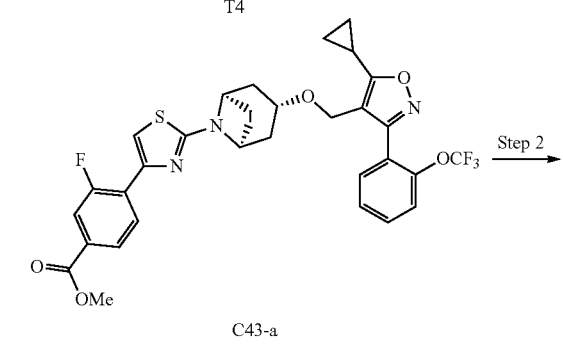

C43-a

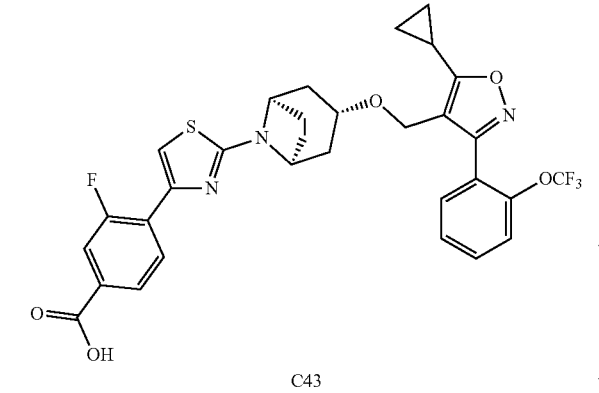

C43

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-fluorobenzoate (C43-a)

Compound (T4) (650 mg, 1.14 mmol) was dissolved in 1,4-dioxane (20 mL), followed by addition of methyl 3-fluoro-4-(4,4,5,5-tetramethyl-1,3,2-dioxaborolan-2-yl)benzoate (248.13 mg, 1.25 mmol), [1,1'-bis(diphenylphosphino)ferrocene]dichloropalladium (93.06 mg, 127.18 μmol) and potassium carbonate (314.50 mg, 2.28 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1) to afford the title compound of this step (350 mg).

MS m/z (ESI): 644.1 [M+H]$^+$.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-fluorobenzoic acid (C43)

Compound (C43-a) (390 mg, 625.31 μmol) was dissolved in tetrahydrofuran (5 mL), an aqueous solution (2 mL) of sodium hydroxide (25.01 mg, 625.31 μmol) was added, and the reaction was performed at 25° C. for 4 hours. The reaction was adjusted to pH 4 with 1M dilute hydrochloric acid, and extracted with ethyl acetate (100 mL×3). The organic phase was dried over anhydrous sodium sulfate, concentrated, and the resulting residue was purified by column chromatography on silica gel (eluent: petroleum ether/ethyl acetate=10/1–6/1) to afford the title compound (1.01 g).

MS m/z (ESI): 620.1 [M+H]$^+$.

$^1$H-NMR (400 MHz, DMSO-d$_6$) δ: 7.71 (t, J=7.8 Hz, 1H), 7.66 (d, J=7.4 Hz, 1H), 7.63-7.54 (m, 2H), 7.50 (d, J=11.7 Hz, 1H), 7.33 (s, 1H), 4.35 (s, 1H), 4.12 (s, 1H), 2.39-2.33 (m, 1H), 2.03 (d, J=14.5 Hz, 1H), 1.80 (s, 2H), 1.69 (d, J=14.7 Hz, 1H), 1.33-1.24 (m, 1H), 1.16 (m, 1H), 1.10 (m, 1H).

Example 11: Preparation of 4-(2-(1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-fluorobenzoic acid (C44)

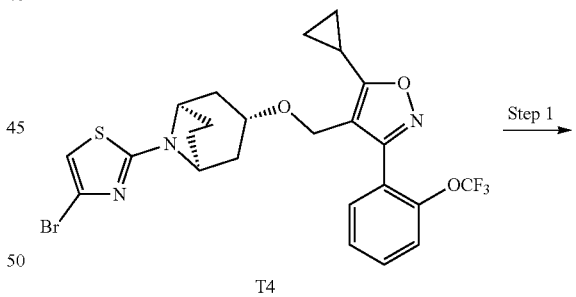

T4

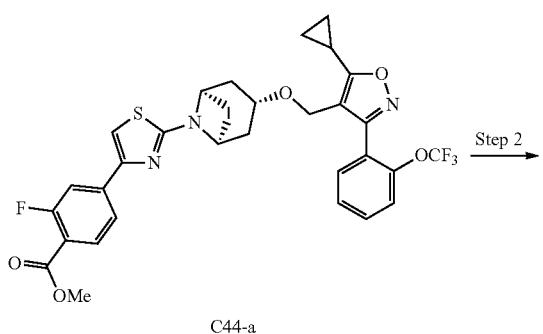

C44-a

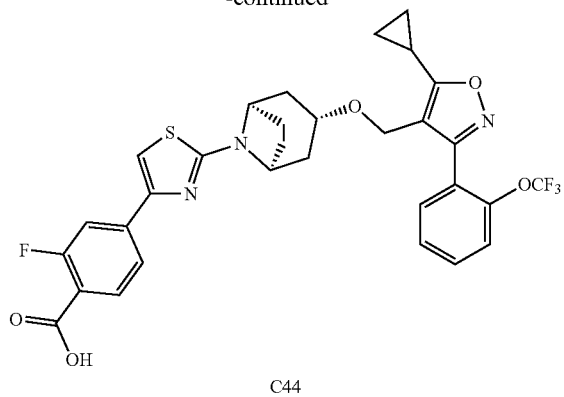

C44

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-fluorobenzoate (C44-a)

Compound (T4) (400 mg, 701.24 μmol) was dissolved in 1,4-dioxane (20 mL), followed by addition of methyl 2-fluoro-4-(4,4,5,5-tetramethyl-1,3,2-dioxaborolan-2-yl)benzoate (152.70 mg, 771.36 μmol), [1,1'-bis(diphenylphosphino)ferrocene]dichloropalladium (57.27 mg, 78.26 μmol) and potassium carbonate (193.54 mg, 1.40 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1) to afford the title compound of this step (200 mg).

MS m/z (ESI): 630.1 [M+H]+.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-fluorobenzoic acid (C44)

Compound (C44-a) (200.00 mg, 310.73 μmol) was dissolved in tetrahydrofuran (5 mL), an aqueous solution (2 mL) of sodium hydroxide (12.43 mg, 310.73 μmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, concentrated, and the resulting residue was purified by column chromatography on silica gel (eluent: petroleum ether/ethyl acetate=10/1~6/1) to afford the title compound (170 mg).

MS m/z (ESI): 620.1 [M+H]+.

1H-NMR (400 MHz, DMSO-d6) δ: 7.85 (d, J=8.1 Hz, 1H), 7.72 (dd, J=17.5, 10.3 Hz, 1H), 7.66 (d, J=7.3 Hz, 1H), 7.58 (dd, J=13.5, 6.3 Hz, 1H), 7.37 (d, J=1.9 Hz, 1H), 4.36 (s, 1H), 4.15 (s, 1H), 2.37 (d, J=4.9 Hz, 1H), 2.03 (d, J=14.7 Hz, 1H), 1.82 (s, 2H), 1.70 (d, J=14.6 Hz, 1H), 1.33-1.24 (m, 1H), 1.15 (dd, J=11.0, 6.1 Hz, 1H), 1.10 (d, J=3.0 Hz, 1H).

Example 12: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-(trifluoromethyl)benzoic acid (C45)

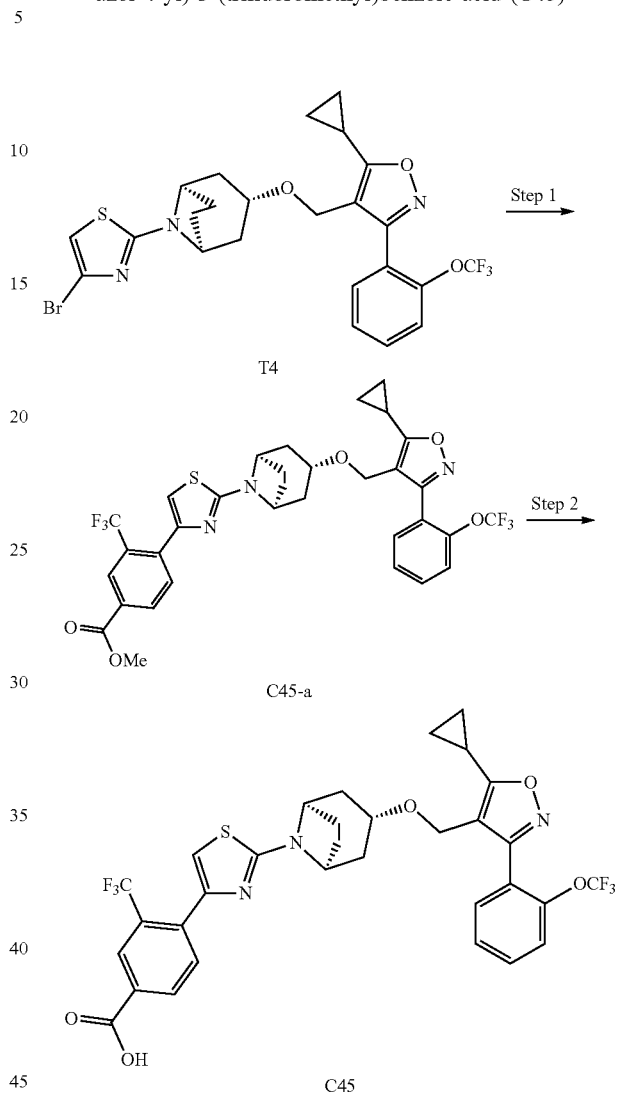

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-(trifluoromethyl)benzoate (C45-a)

Compound (T4) (800 mg, 1.40 mmol) was dissolved in 1,4-dioxane (20 mL), followed by addition of methyl 4-(4,4,5,5-tetramethyl-1,3,2-dioxaborolan-2-yl)-3-(trifluoromethyl)benzoate (509.26 mg, 1.54 mmol), [1,1'-bis(diphenylphosphino)ferrocene]dichloropalladium (114.53 mg, 156.53 μmol) and potassium carbonate (387.08 mg, 2.80 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1) to afford the title compound of this step (350 mg).

MS m/z (ESI): 693.1 [M+H]⁺.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-3-(trifluoromethyl)benzoic acid (C45)

Compound (C45-a) (350.00 mg, 504.57 µmol) was dissolved in tetrahydrofuran (5 mL), an aqueous solution (2 mL) of sodium hydroxide (20.18 mg, 504.57 µmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, filtered, concentrated, and the resulting residue was purified by column chromatography on silica gel (eluent: petroleum ether/ethyl acetate=10/1–6/1) to afford the title compound (320 mg).

MS m/z (ESI): 680.1 [M+H]⁺.

$^1$H-NMR (400 MHz, DMSO-d$_6$) δ: 7.81 (d, J=8.1 Hz, 1H), 7.70-7.61 (m, 1H), 7.55 (dd, J=12.1, 4.8 Hz, 1H), 7.03 (s, 1H), 4.33 (s, 1H), 4.05 (s, 1H), 2.33 (m), 2.05-1.97 (m, 1H), 1.79 (s, 2H), 1.65 (d, J=14.5 Hz, 1H), 1.25 (d, J=9.3 Hz, 1H), 1.13 (m, 1H), 1.08 (m, 1H).

Example 13: Preparation of 4-(2-(1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-(trifluoromethyl)benzoic acid (C46)

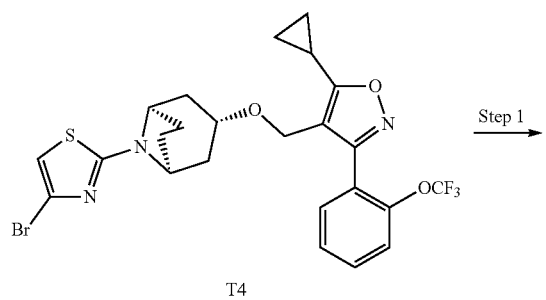

T4

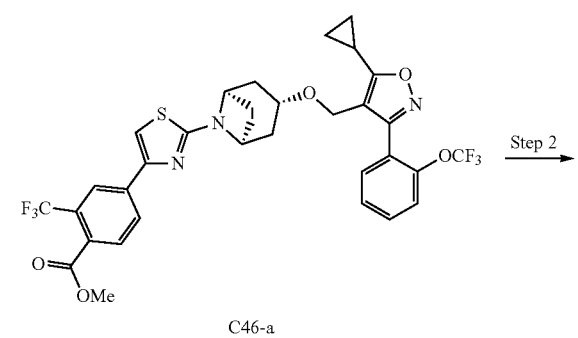

C46-a

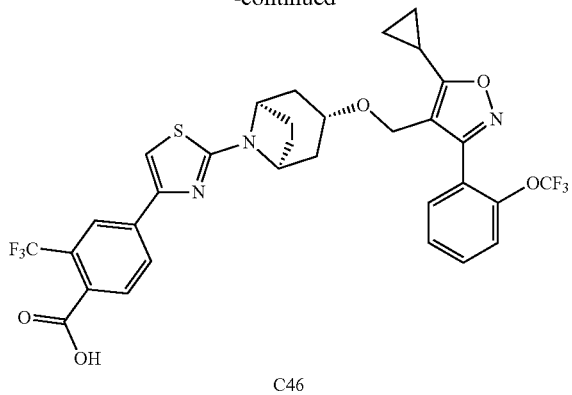

C46

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-(trifluoromethyl)benzoate (C46-a)

Compound (T4) (0.4 g, 701.24 µmol) was dissolved in 1,4-dioxane (20 mL), followed by addition of methyl 4-(4,4,5,5-tetramethyl-1,3,2-dioxaborolan-2-yl)-2-(trifluoromethyl)benzoate (277.78 mg, 841.48 µmol), [1,1'-bis(diphenylphosphino)ferrocene]dichloropalladium (57.27 mg, 70.12 µmol) and potassium carbonate (193.83 mg, 1.40 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=15/1–8/1) to afford the title compound of this step (0.36 g).

MS m/z (ESI): 694.1 [M+H]⁺.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)-2-(trifluoromethyl)benzoic acid (C46)

Compound (C46-a) (360.00 mg, 518.99 µmol) was dissolved in tetrahydrofuran (5 mL), an aqueous solution (2 mL) of sodium hydroxide (20.71 mg, 518.99 µmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, concentrated, and the resulting residue was purified by column chromatography on silica gel (eluent: petroleum ether/ethyl acetate=10/1–6/1) to afford the title compound (45 mg).

MS m/z (ESI): 680.1 [M+H]⁺.

$^1$H-NMR (400 MHz, DMSO-d$_6$) δ: 8.21 (s, 1H), 8.16 (d, J=7.3 Hz, 1H), 7.83 (d, J=7.2 Hz, 1H), 7.64 (dd, J=18.9, 11.7 Hz, 1H), 7.57 (d, J=12.8 Hz, 1H), 4.33 (s, 1H), 4.12 (s, 1H), 2.33 (s, 1H), 2.01 (d, J=12.4 Hz, 1H), 1.79 (s, 1H), 1.68 (m, 1H), 1.19-1.01 (m, 1H).

Example 14: Preparation of 4-(2-(1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylic acid (C47)

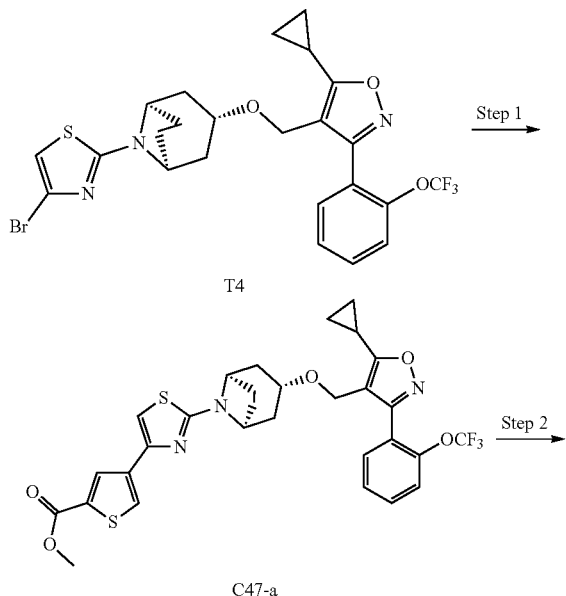

Step 1: Preparation of methyl 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylate (C47-a)

Compound (T4) (0.5 g, 876.55 μmol) was dissolved in 1,4-dioxane (20 mL), followed by addition of methyl 4-(4,4,5,5-tetramethyl-1,3,2-dioxaborolan-2-yl)thiophene-2-carboxylate (282.04 mg, 1.05 mmol), [1,1'-bis(diphenylphosphino)ferrocene]dichloropalladium (64.43 mg, 78.89 μmol) and potassium carbonate (241.93 mg, 1.75 mmol) at room temperature, replacement with nitrogen was performed for 2-3 times, and the reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1–6/1) to afford the title compound of this step (0.14 g).

MS m/z (ESI): 632.1 [M+H]$^+$.

Step 2: Preparation of 4-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylic acid (C47)

Compound (C47-a) (200.00 mg, 316.61 μmol) was dissolved in tetrahydrofuran (5 mL), an aqueous solution (2 mL) of sodium hydroxide (12.66 mg, 316.61 μmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, filtered, concentrated, and the resulting residue was purified by column chromatography on silica gel (eluent: petroleum ether/ethyl acetate=10/1–6/1) to afford the title compound of this step (0.1 g).

MS m/z (ESI): 618.1 [M+H]$^+$.

$^1$H-NMR (400 MHz, DMSO-d$_6$) δ: 8.21 (s, 1H), 8.16 (d, J=7.3 Hz, 1H), 7.83 (d, J=7.2 Hz, 1H), 7.64 (dd, J=18.9, 11.7 Hz, 1H), 7.57 (d, J=12.8 Hz, 1H), 4.33 (s, 1H), 4.12 (s, 1H), 2.33 (s, 1H), 2.01 (d, J=12.4 Hz, 1H), 1.79 (s, 1H), 1.68 (m, 1H), 1.19-1.01 (m, 1H).

Example 15: Preparation of 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-3-carboxylic acid (C48)

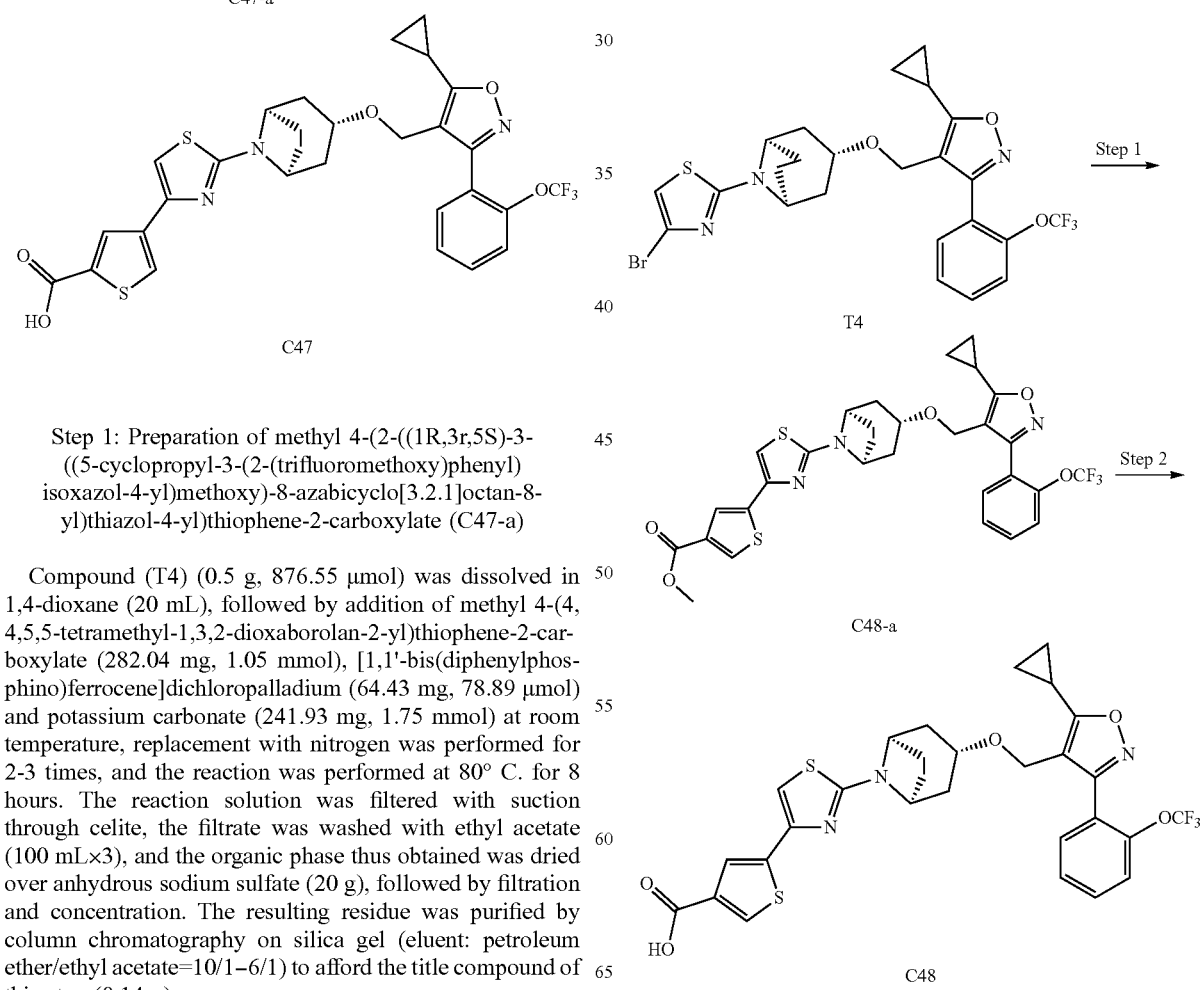

Step 1: Preparation of methyl 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-3-carboxylate (C48-a)

Compound (T4) (0.5 g, 876.55 μmol) was dissolved in 1,4-dioxane (20 mL), followed by addition of methyl 5-(4,4,5,5-tetramethyl-1,3,2-dioxaborolan-2-yl)thiophene-3-carboxylate (282.04 mg, 1.05 mmol), [1,1'-bis(diphenylphosphino)ferrocene]dichloropalladium (64.43 mg, 78.89 μmol) and potassium carbonate (241.93 mg, 1.75 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1–6/1) to afford the title compound of this step (0.2 g).

MS m/z (ESI): 632.1 [M+H]$^+$.

Step 2: Preparation of 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-3-carboxylic acid (C48)

Compound (C48-a) (140.00 mg, 221.63 μmol) was dissolved in tetrahydrofuran (5 mL), an aqueous solution (2 mL) of sodium hydroxide (8.86 mg, 221.63 μmol) was added, and the reaction was performed at 25° C. for 4 hours. The reaction was adjusted to pH 4 with 1 M dilute hydrochloric acid, and extracted with ethyl acetate (100 ml×3). The organic phase was dried over anhydrous sodium sulfate, filtered, concentrated, and the resulting residue was purified by column chromatography on silica gel (eluent: petroleum ether/ethyl acetate=10/1–6/1) to afford the title compound (70 mg).

MS m/z (ESI): 618.1 [M+H]+.

$^1$H-NMR (400 MHz, DMSO-d$_6$) δ: 8.14 (s, 1H), 7.74-7.68 (m, 1H), 7.66 (d, J=6.7 Hz, 1H), 7.58 (dd, J=13.4, 6.2 Hz, 1H), 7.26 (s, 1H), 4.35 (s, 1H), 4.09 (s, 1H), 2.36 (s, 1H), 2.01 (d, J=15.4 Hz, 1H), 1.80 (s, 2H), 1.69 (d, J=14.8 Hz, 1H), 1.16 (d, J=8.4 Hz, 1H), 1.10 (d, J=2.8 Hz, 1H).

Example 16: Preparation of 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylic acid (C35)

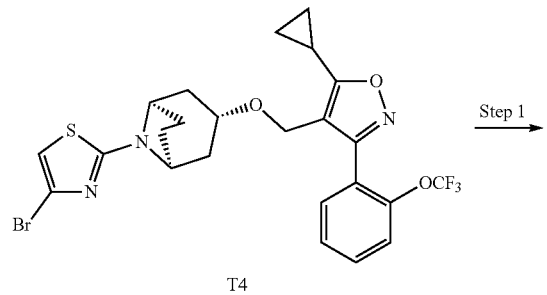

T4

Step 1 →

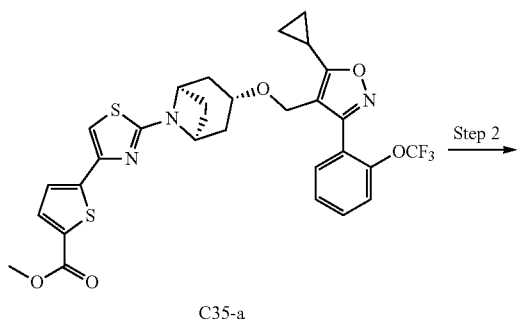

C35-a

Step 2 →

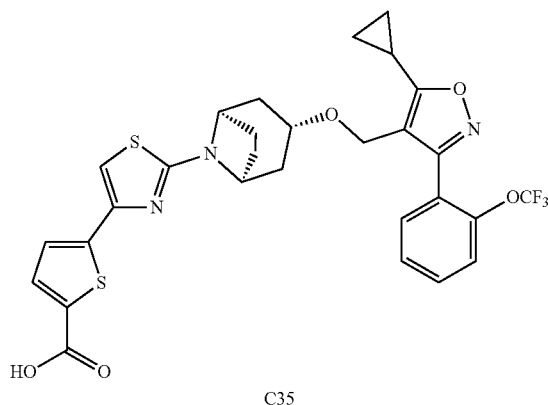

C35

Step 1: Preparation of methyl 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylate (C35-a)

Compound (T4) (709.12 mg, 1.24 mmol) was dissolved in 1,4-dioxane (20 mL), followed by addition of methyl 5-(4,4,5,5-tetramethyl-1,3,2-dioxaborolan-2-yl)thiophene-2-carboxylate (0.4 g, 1.49 mmol), [1,1'-bis(diphenylphosphino)ferrocene]dichloropalladium (90.87 mg, 111.28 μmol) and potassium carbonate (343.11 mg, 2.48 mmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1–6/1) to afford the title compound of this step (0.25 g).

MS m/z (ESI): 632.1 [M+H]+.

Step 2: Preparation of 5-(2-(((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)thiophene-2-carboxylic acid (C35)

Compound (C35-a) (200.00 mg, 316.61 µmol) was dissolved in tetrahydrofuran (5 mL), an aqueous solution (2 mL) of sodium hydroxide (12.66 mg, 316.61 µmol) was added, and the reaction was performed at 25° C. for 4 hours. The reaction was adjusted to pH 4 with 1 M dilute hydrochloric acid, and extracted with ethyl acetate (100 mL×3). The organic phase was dried over anhydrous sodium sulfate, filtered, concentrated, and the resulting residue was purified by column chromatography on silica gel (eluent: petroleum ether/ethyl acetate=10/1–6/1) to afford the title compound of this step (25 mg).

MS m/z (ESI): 618.1 [M+H]$^+$.

$^1$H-NMR (400 MHz, DMSO-d$_6$) δ: 7.65 (m, 2H), 7.56 (m, 1H), 7.44 (s, 1H), 7.31 (s, 1H), 4.33 (s, 1H), 4.07 (s, 1H), 3.52 (s, 1H), 2.33 (s, 1H), 1.99 (d, J=14.4 Hz, 1H), 1.78 (s, 2H), 1.66 (d, J=14.6 Hz, 1H), 1.13 (m, 1H), 1.08 (s, 1H).

Example 17: Preparation of 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)picolinic acid (C50)

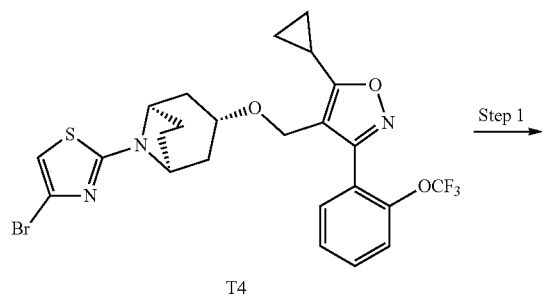

T4

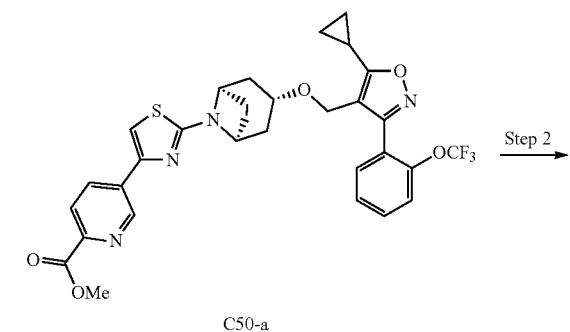

C50-a

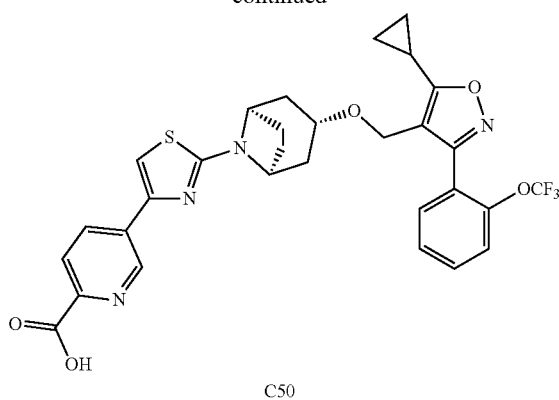

C50

Step 1: Preparation of methyl 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)picolinate (C50-a)

Compound (T4) (50 mg, 87.65 µmol) was dissolved in 1,4-dioxane (20 mL), followed by addition of methyl 5-(4,4,5,5-tetramethyl-1,3,2-dioxaborolan-2-yl)picolinate (27.67 mg, 105.19 µmol), [1,1'-bis(diphenylphosphino)ferrocene]dichloropalladium (7.16 mg, 8.77 µmol) and potassium carbonate (12.11 mg, 87.65 µmol) at room temperature, and replacement with nitrogen was performed for 2-3 times. The reaction was performed at 80° C. for 8 hours. The reaction solution was filtered with suction through celite, the filtrate was washed with ethyl acetate (100 mL×3), and the organic phase thus obtained was dried over anhydrous sodium sulfate (20 g), followed by filtration and concentration. The resulting residue was purified by column chromatography on silica gel (eluent: petroleum ether/ethyl acetate=10/1–6/1) to afford the title compound of this step (20 mg).

MS m/z (ESI): 626.1 [M+H]$^+$.

Step 2: Preparation of 5-(2-((1R,3r,5S)-3-((5-cyclopropyl-3-(2-(trifluoromethoxy)phenyl)isoxazol-4-yl)methoxy)-8-azabicyclo[3.2.1]octan-8-yl)thiazol-4-yl)picolinic acid (C50)

Compound (C50-a) (200 mg, 316.61 µmol) was dissolved in tetrahydrofuran (5 mL), an aqueous solution (2 mL) of sodium hydroxide (12.66 mg, 316.61 µmol) was added, and the reaction was performed at 25° C. for 4 hours. The reaction was adjusted to pH 4 with 1 M dilute hydrochloric acid, extracted with ethyl acetate (100 mL×3), and the organic phase was dried over anhydrous sodium sulfate, followed by filtration and concentration. The resulting residue was purified by column chromatography on silica gel (eluent: petroleum ether/ethyl acetate=10/1–6/1) to afford the title compound (25 mg).

MS m/z (ESI): 618.1 [M+H]$^+$.

$^1$H-NMR (400 MHz, DMSO-d$_6$) δ: 8.88 (s, 1H), 8.20 (dd, J=8.1, 2.1 Hz, 1H), 7.93 (d, J=8.2 Hz, 1H), 7.71-7.61 (m, 1H), 7.55 (t, J=7.5 Hz, 1H), 7.44 (s, 1H), 4.32 (s, 1H), 4.11 (s, 1H), 3.52 (s, 1H), 2.33 (dd, J=10.8, 5.9 Hz, 1H), 2.01 (d, J=13.7 Hz, 1H), 1.79 (s, 2H), 1.67 (d, J=14.5 Hz, 1H), 1.13 (m, 1H), 1.09-1.03 (m, 1H).

The compounds in following Table 1 were prepared according to synthetic methods similar to those described in above Examples 1-17:

TABLE 1

| Compound No. | Structure | Name | MS |
|---|---|---|---|
| C7 | 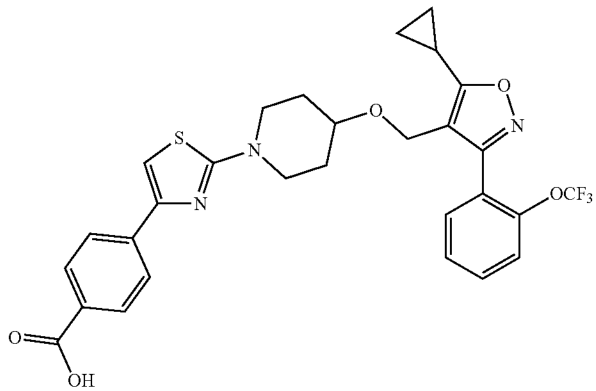 [SMILES: O=C(O)c1ccc(-c2csc(N3CCC(OCc4c(-c5ccccc5OC(F)(F)F)noc4C4CC4)CC3)n2)cc1] | 4-(2-(4-((5-cyclopropyl-3-(2-(trifluoromethoxy)phenyl)isoxazol-4-yl)methoxy)piperidin-1-yl)thiazol-4-yl)benzoic acid | MS m/z (ESI): 586 [M + H]+ |
| C8 | 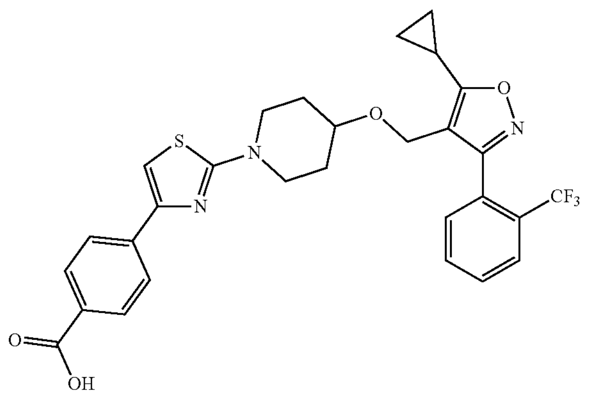 [SMILES: O=C(O)c1ccc(-c2csc(N3CCC(OCc4c(-c5ccccc5C(F)(F)F)noc4C4CC4)CC3)n2)cc1] | 4-(2-(4-((5-cyclopropyl-3-(2-(trifluoromethyl)phenyl)isoxazol-4-yl)methoxy)piperidin-1-yl)thiazol-4-yl)benzoic acid | MS m/z (ESI): 570 [M + H]+ |
| C9 | 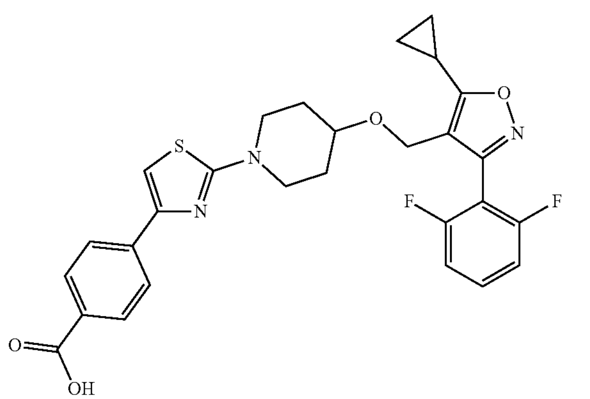 [SMILES: O=C(O)c1ccc(-c2csc(N3CCC(OCc4c(-c5c(F)cccc5F)noc4C4CC4)CC3)n2)cc1] | 4-(2-(4-((5-cyclopropyl-3-(2,6-difluorophenyl)isoxazol-4-yl)methoxy)piperidin-1-yl)thiazol-4-yl)benzoic acid | MS m/z (ESI): 538 [M + H]+ |
| C10 | 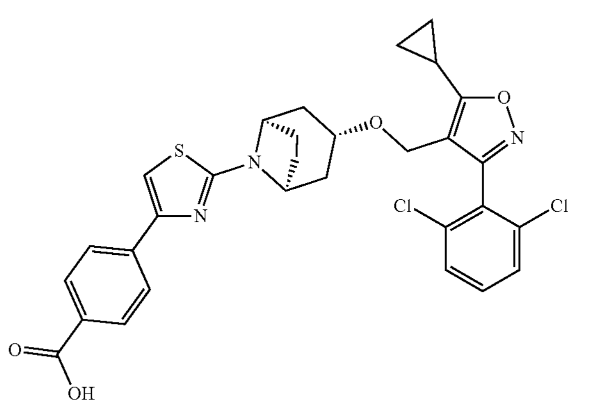 [SMILES: O=C(O)c1ccc(-c2csc(N3[C@@H]4CC[C@H]3C[C@@H](OCc3c(-c5c(Cl)cccc5Cl)noc3C3CC3)C4)n2)cc1] | 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)benzoic acid | MS m/z (ESI): 596 [M + H]+ |

TABLE 1-continued

| Compound No. | Structure | Name | MS |
|---|---|---|---|
| C11 | 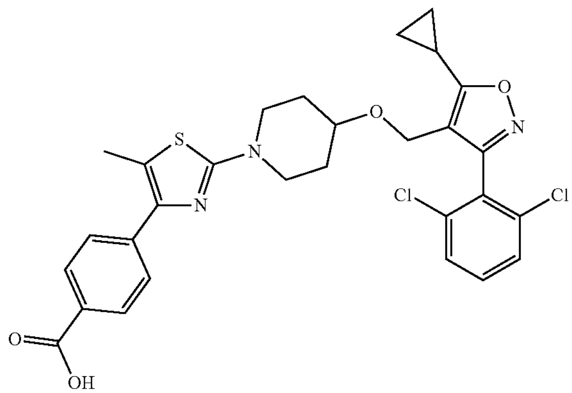 [SMILES: Cc1sc(N2CCC(OCc3c(-c4c(Cl)cccc4Cl)noc3C3CC3)CC2)nc1-c1ccc(C(=O)O)cc1] | 4-(2-(4-((5-cyclopropyl-3-(2,6-dichlorophenyl)isoxazol-4-yl)methoxy)piperidin-1-yl)-5-methylthiazol-4-yl)benzoic acid | MS m/z (ESI): 584 [M + H]+ |
| C12 | 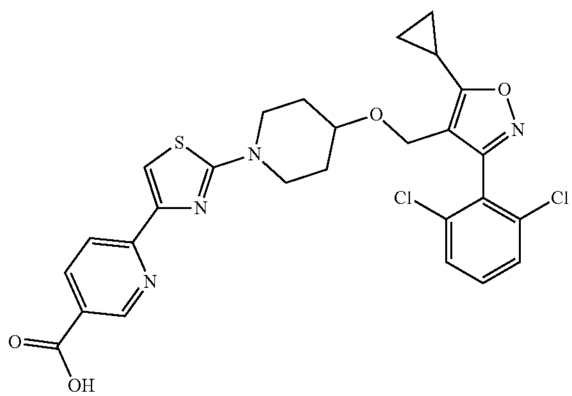 [SMILES: O=C(O)c1ccc(-c2csc(N3CCC(OCc4c(-c5c(Cl)cccc5Cl)noc4C4CC4)CC3)n2)nc1] | 6-(2-(4-((5-cyclopropyl-3-(2,6-dichlorophenyl)isoxazol-4-yl)methoxy)piperidin-1-yl)thiazol-4-yl)nicotinic acid | MS m/z (ESI): 571 [M + H]+ |
| C13 | 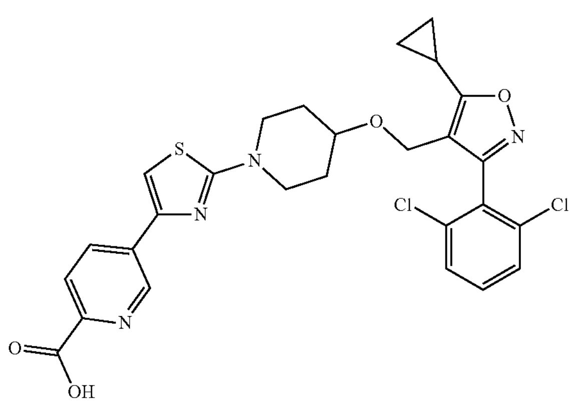 [SMILES: O=C(O)c1ccc(-c2csc(N3CCC(OCc4c(-c5c(Cl)cccc5Cl)noc4C4CC4)CC3)n2)cn1] | 5-(2-(4-((5-cyclopropyl-3-(2,6-dichlorophenyl)isoxazol-4-yl)methoxy)piperidin-1-yl)thiazol-4-yl)-2-picolinic acid | MS m/z (ESI): 571 [M + H]+ |

TABLE 1-continued

| Compound No. | Structure | Name | MS |
|---|---|---|---|
| C14 | 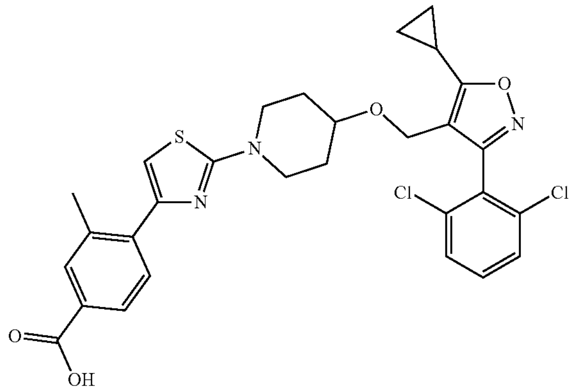 [SMILES: Cc1cc(C(=O)O)ccc1-c1csc(N2CCC(OCc3c(-c4c(Cl)cccc4Cl)noc3C3CC3)CC2)n1] | 4-(2-(4-((5-cyclopropyl-3-(2,6-dichlorophenyl)isoxazol-4-yl)methoxy)piperidin-1-yl)thiazol-4-yl)-3-methylbenzoic acid | MS m/z (ESI): 584 [M + H]+ |
| C15 | 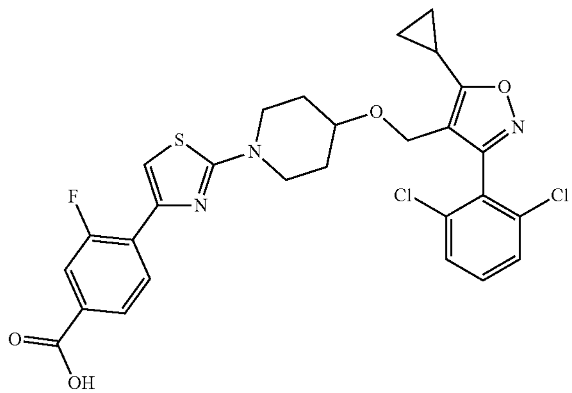 [SMILES: O=C(O)c1ccc(-c2csc(N3CCC(OCc4c(-c5c(Cl)cccc5Cl)noc4C4CC4)CC3)n2)c(F)c1] | 4-(2-(4-((5-cyclopropyl-3-(2,6-dichlorophenyl)isoxazol-4-yl)methoxy)piperidin-1-yl)thiazol-4-yl)-3-fluorobenzoic acid | MS m/z (ESI): 588 [M + H]+ |
| C16 | 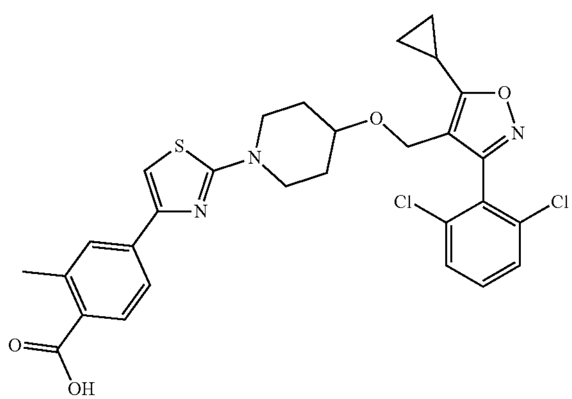 | 4-(2-(4-((5-cyclopropyl-3-(2,6-dichlorophenyl)isoxazol-4-yl)methoxy)piperidin-1-yl)thiazol-4-yl)-2-methylbenzoic acid | MS m/z (ESI): 584 [M + H]+ |
| C17 | 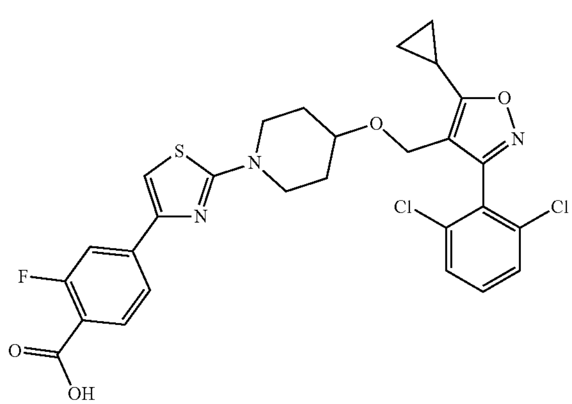 | 4-(2-(4-((5-cyclopropyl-3-(2,6-dichlorophenyl)isoxazol-4-yl)methoxy)piperidin-1-yl)thiazol-4-yl)-2-fluorobenzoic acid | MS m/z (ESI): 588 [M + H]+ |

TABLE 1-continued

| Compound No. | Structure | Name | MS |
|---|---|---|---|
| C18 | 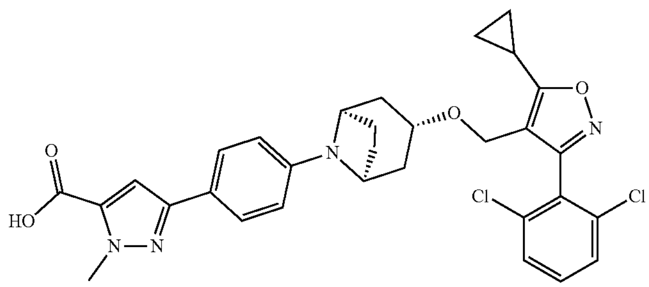 [SMILES: Cn1nc(-c2ccc(N3[C@@H]4CC[C@H]3C[C@@H](OCc3c(-c5c(Cl)cccc5Cl)noc3C3CC3)C4)cc2)cc1C(=O)O] | 3-(4-((1R,3r,5S)-3-((5-cyclopropyl-3-(2,6-dichlorophenyl)isoxazol-4-yl)methoxy)-8-azabicyclo[3.2.1]octan-8-yl)phenyl)-1-methyl-1H-pyrazole-5-carboxylic acid | MS m/z (ESI): 593 [M + H]+ |
| C19 | 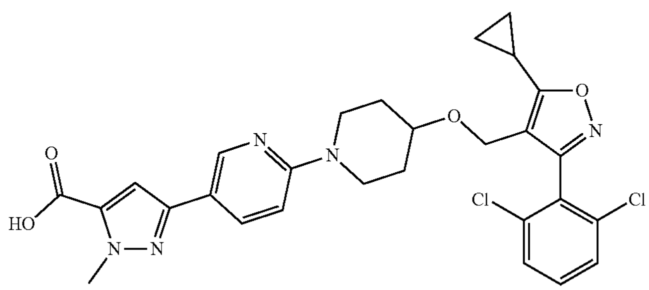 [SMILES: Cn1nc(-c2ccc(N3CCC(OCc4c(-c5c(Cl)cccc5Cl)noc4C4CC4)CC3)nc2)cc1C(=O)O] | 3-(6-(4-((5-cyclopropyl-3-(2,6-dichlorophenyl)isoxazol-4-yl)methoxy)piperidin-1-yl)pyridine-3-yl)-1-methyl-1H-pyrazole-5-carboxylic acid | MS m/z (ESI): 568 [M + H]+ |
| C20 | 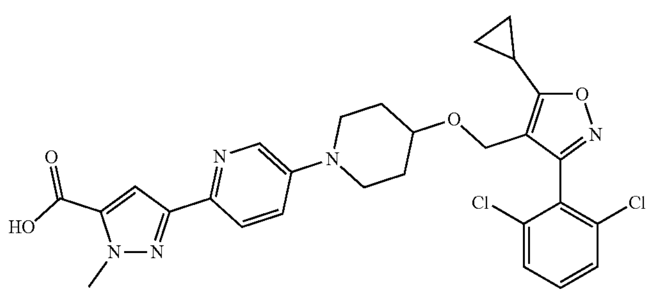 [SMILES: Cn1nc(-c2ccc(N3CCC(OCc4c(-c5c(Cl)cccc5Cl)noc4C4CC4)CC3)cn2)cc1C(=O)O] | 3-(5-(4-((5-cyclopropyl-3-(2,6-dichlorophenyl)isoxazol-4-yl)methoxy)piperidin-1-yl)pyridine-2-yl)-1-methyl-1H-pyrazole-5-carboxylic acid | MS m/z (ESI): 568 [M + H]+ |
| C21 | 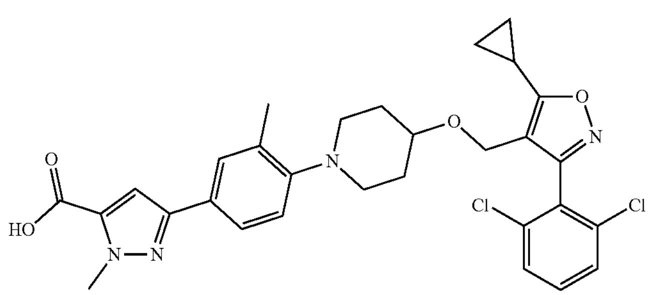 | 3-(4-(4-((5-cyclopropyl-3-(2,6-dichlorophenyl)isoxazol-4-yl)methoxy)piperidin-1-yl)-3-methylphenyl)-1-methyl-1H-pyrazole-5-carboxylic acid | MS m/z (ESI): 581 [M + H]+ |
| C22 | 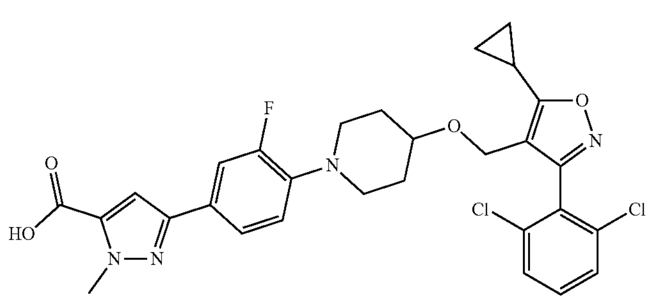 | 3-(4-(4-((5-cyclopropyl-3-(2,6-dichlorophenyl)isoxazol-4-yl)methoxy)piperidin-1-yl)-3-fluorophenyl)-1-methyl-1H-pyrazole-5-carboxylic acid | MS m/z (ESI): 585 [M + H]+ |

TABLE 1-continued

| Compound No. | Structure | Name | MS |
|---|---|---|---|
| C23 | 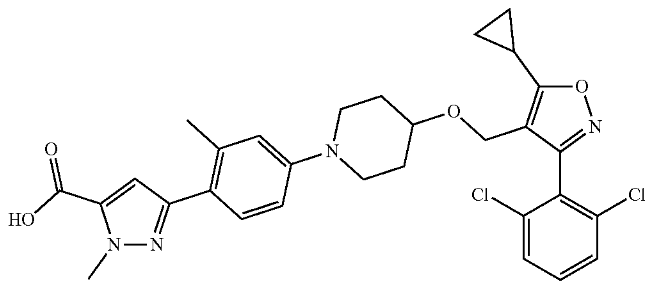 [SMILES: Cc1cc(N2CCC(OCc3c(-c4c(Cl)cccc4Cl)noc3C3CC3)CC2)ccc1-c1cc(C(=O)O)n(C)n1] | 3-(4-(4-((5-cyclopropyl-3-(2,6-dichlorophenyl)isoxazol-4-yl)methoxy)piperidin-1-yl)-2-methylphenyl)-1-methyl-1H-pyrazole-5-carboxylic acid | MS m/z (ESI): 581 [M + H]+ |
| C24 | 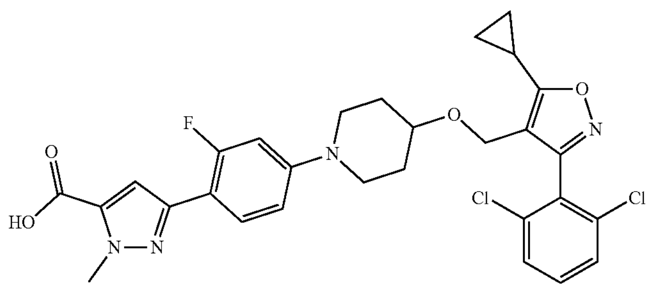 [SMILES: Cn1nc(-c2ccc(N3CCC(OCc4c(-c5c(Cl)cccc5Cl)noc4C4CC4)CC3)cc2F)cc1C(=O)O] | 3-(4-(4-((5-cyclopropyl-3-(2,6-dichlorophenyl)isoxazol-4-yl)methoxy)piperidin-1-yl)-2-fluorophenyl)-1-methyl-1H-pyrazole-5-carboxylic acid | MS m/z (ESI): 585 [M + H]+ |
| C25 | 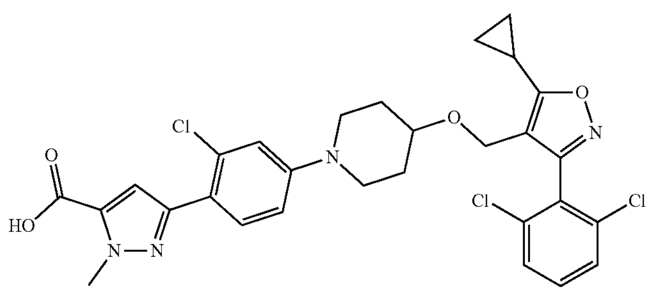 [SMILES: Cn1nc(-c2ccc(N3CCC(OCc4c(-c5c(Cl)cccc5Cl)noc4C4CC4)CC3)cc2Cl)cc1C(=O)O] | 3-(2-chloro-4-(4-((5-cyclopropyl-3-(2,6-dichlorophenyl)isoxazol-4-yl)methoxy)piperidin-1-yl)phenyl)-1-methyl-1H-pyrazole-5-carboxylic acid | MS m/z (ESI): 601 [M + H]+ |
| C26 | 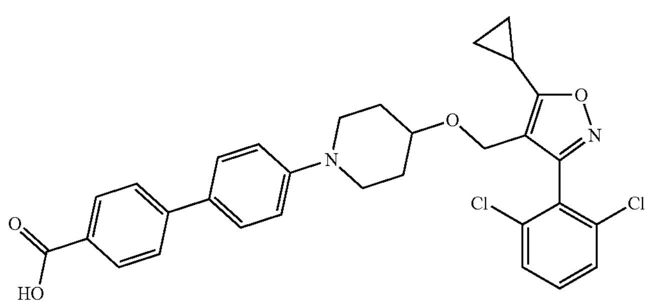 [SMILES: O=C(O)c1ccc(-c2ccc(N3CCC(OCc4c(-c5c(Cl)cccc5Cl)noc4C4CC4)CC3)cc2)cc1] | 4'-(4-((5-cyclopropyl-3-(2,6-dichlorophenyl)isoxazol-4-yl)methoxy)piperidin-1-yl)-[1,1'-biphenyl]-4-carboxylic acid | MS m/z (ESI): 563 [M + H]+ |
| C27 | 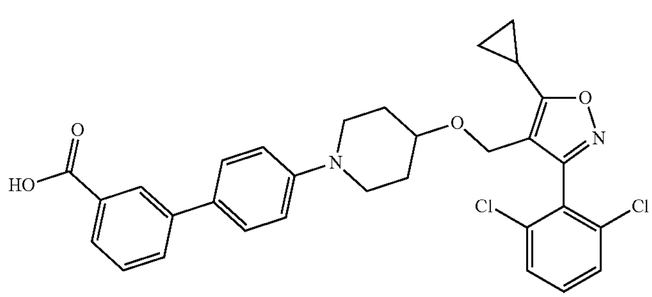 [SMILES: O=C(O)c1cccc(-c2ccc(N3CCC(OCc4c(-c5c(Cl)cccc5Cl)noc4C4CC4)CC3)cc2)c1] | 4'-(4-((5-cyclopropyl-3-(2,6-dichlorophenyl)isoxazol-4-yl)methoxy)piperidin-1-yl)-[1,1'-biphenyl]-3-carboxylic acid | MS m/z (ESI): 563 [M + H]+ |

TABLE 1-continued

| Compound No. | Structure | Name | MS |
|---|---|---|---|
| C28 | 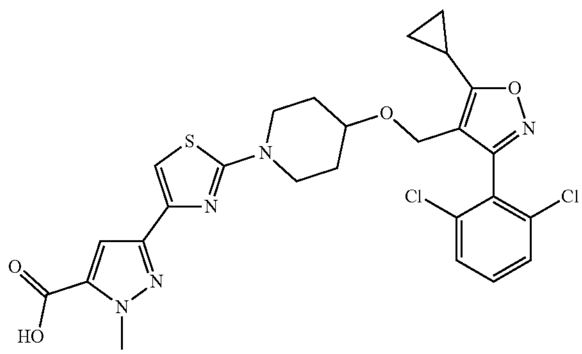 [SMILES: Cn1nc(-c2csc(N3CCC(OCc4c(-c5c(Cl)cccc5Cl)noc4C4CC4)CC3)n2)cc1C(=O)O] | 3-(2-(4-((5-cyclopropyl-3-(2,6-dichlorophenyl)isoxazol-4-yl)methoxy)piperidin-1-yl)thiazol-4-yl)-1-methyl-1H-pyrazole-5-carboxylic acid | MS m/z (ESI): 574 [M + H]$^+$ |
| C29 | 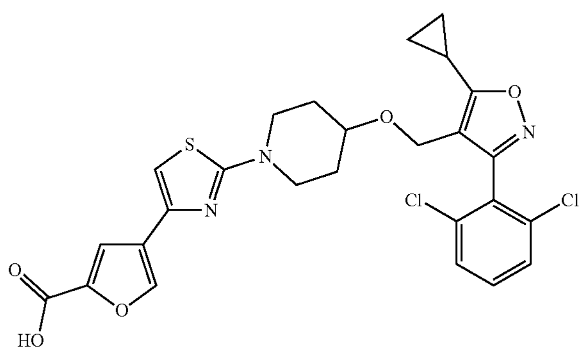 [SMILES: O=C(O)c1cc(-c2csc(N3CCC(OCc4c(-c5c(Cl)cccc5Cl)noc4C4CC4)CC3)n2)cs1] | 4-(2-(4-((5-cyclopropyl-3-(2,6-dichlorophenyl)isoxazol-4-yl)methoxy)piperidin-1-yl)thiazol-4-yl)furan-2-carboxylic acid | MS m/z (ESI): 560 [M + H]$^+$ |
| C30 | 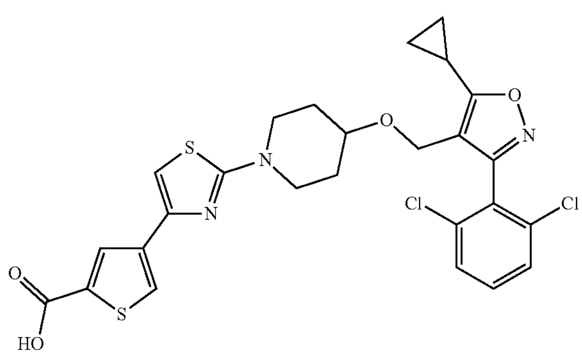 | 4-(2-(4-((5-cyclopropyl-3-(2,6-dichlorophenyl)isoxazol-4-yl)methoxy)piperidin-1-yl)thiazol-4-yl)thiophene-2-carboxylic acid | MS m/z (ESI): 576 [M + H]$^+$ |
| C31 | 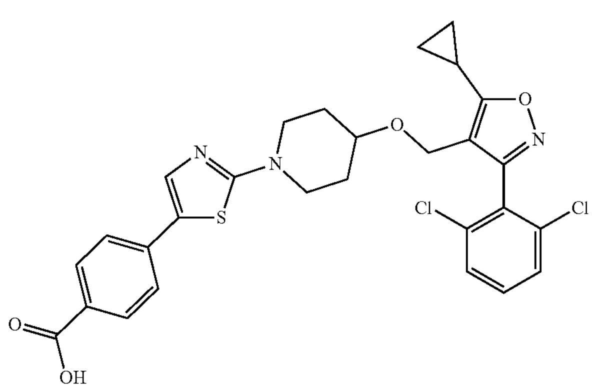 [SMILES: O=C(O)c1ccc(-c2cnc(N3CCC(OCc4c(-c5c(Cl)cccc5Cl)noc4C4CC4)CC3)s2)cc1] | 4-(2-(4-((5-cyclopropyl-3-(2,6-dichlorophenyl)isoxazol-4-yl)methoxy)piperidin-1-yl)thiazol-5-yl)benzoic acid | MS m/z (ESI): 570 [M + H]$^+$ |

TABLE 1-continued

| Compound No. | Structure | Name | MS |
|---|---|---|---|
| C32 | 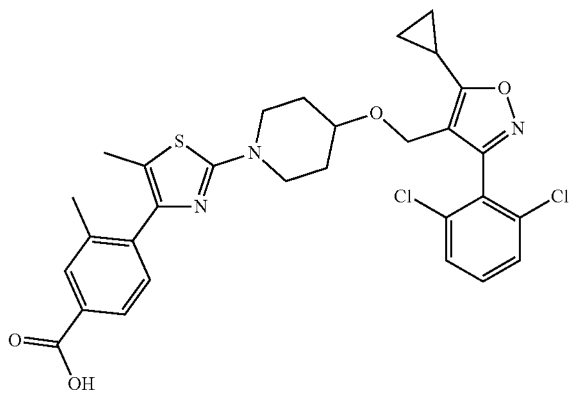 [SMILES: Cc1cc(C(=O)O)ccc1-c1nc(N2CCC(OCc3c(-c4c(Cl)cccc4Cl)noc3C3CC3)CC2)sc1C] | 4-(2-(4-((5-cyclopropyl-3-(2,6-dichlorophenyl)isoxazol-4-yl)methoxy)piperidin-1-yl)-5-methylthiazol-4-yl)-3-methylbenzoic acid | MS m/z (ESI): 598 [M + H]$^+$ |
| C33 | 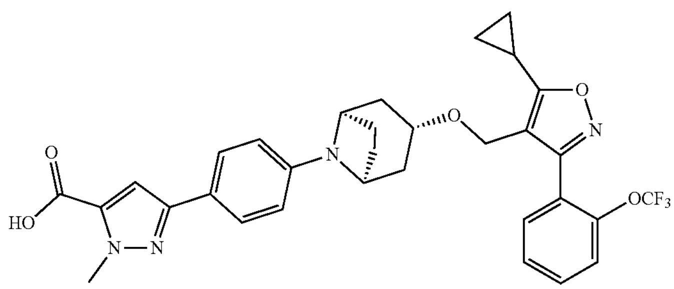 [SMILES: Cn1nc(-c2ccc(N3[C@@H]4CC[C@H]3C[C@@H](OCc3c(-c5ccccc5OC(F)(F)F)noc3C3CC3)C4)cc2)cc1C(=O)O] | 3-(4-((1R,3r,5S)-3-((5-cyclopropyl-3-(2-(trifluoromethoxy)phenyl)isoxazol-4-yl)methoxy)-8-azabicyclo[3.2.1]octan-8-yl)phenyl)-1-methyl-1H-pyrazole-5-carboxylic acid | MS m/z (ESI): 609 [M + H]$^+$ |
| C34 | 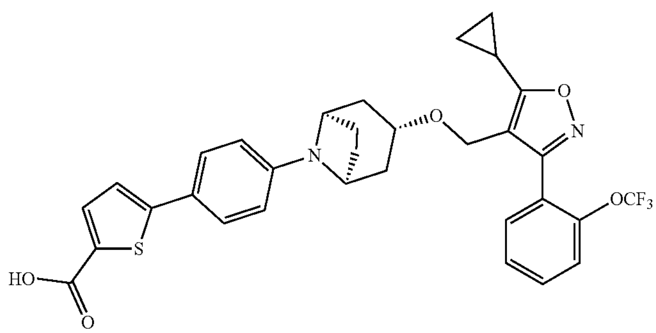 [SMILES: O=C(O)c1ccc(-c2ccc(N3[C@@H]4CC[C@H]3C[C@@H](OCc3c(-c5ccccc5OC(F)(F)F)noc3C3CC3)C4)cc2)s1] | 5-(4-((1R,3r,5S)-3-((5-cyclopropyl-3-(2-(trifluoromethoxy)phenyl)isoxazol-4-yl)methoxy)-8-azabicyclo[3.2.1]octan-8-yl)phenyl)thiophene-2-carboxylic acid | MS m/z (ESI): 611 [M + H]$^+$ |
| C36 | 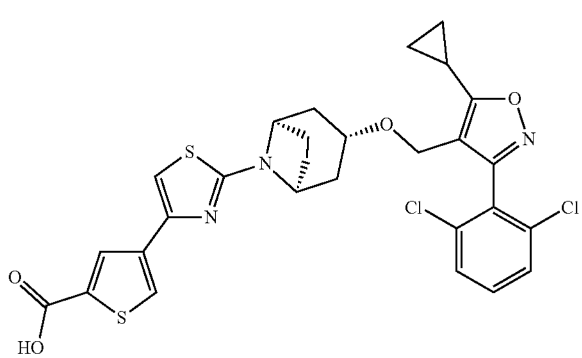 [SMILES: O=C(O)c1cc(-c2csc(N3[C@@H]4CC[C@H]3C[C@@H](OCc3c(-c5c(Cl)cccc5Cl)noc3C3CC3)C4)n2)cs1] | 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)thiophene-2-carboxylic acid | MS m/z (ESI): 602 [M + H]$^+$ |

TABLE 1-continued

| Compound No. | Structure | Name | MS |
|---|---|---|---|
| C38 | 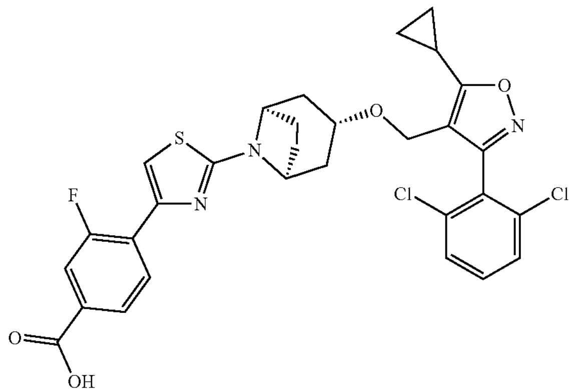 [SMILES: O=C(O)c1ccc(-c2csc(N3[C@@H]4CC[C@H]3C[C@@H](OCc3c(-c5c(Cl)cccc5Cl)noc3C3CC3)C4)n2)c(F)c1] | 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)-3-fluorobenzoic acid | MS m/z (ESI): 614 [M + H]+ |
| C39 | 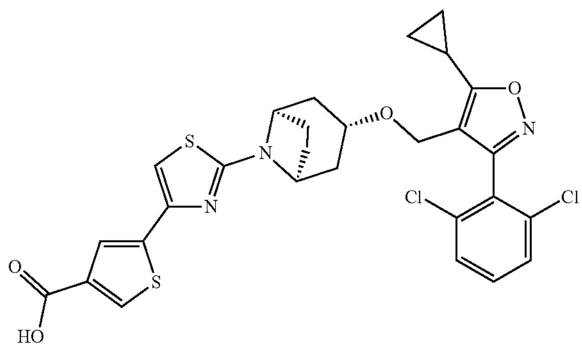 [SMILES: O=C(O)c1csc(-c2csc(N3[C@@H]4CC[C@H]3C[C@@H](OCc3c(-c5c(Cl)cccc5Cl)noc3C3CC3)C4)n2)c1] | 5-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)thiophene-3-carboxylic acid | MS m/z (ESI): 602 [M + H]+ |
| C40 | 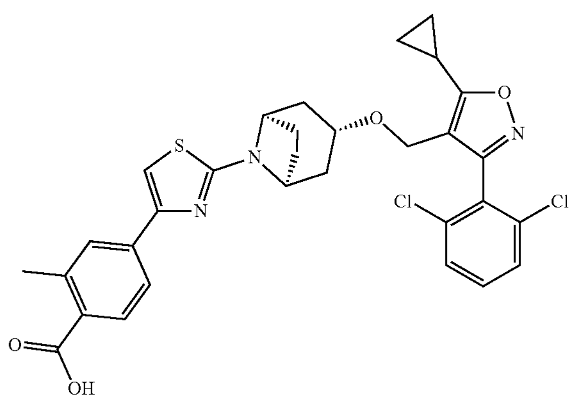 [SMILES: Cc1cc(-c2csc(N3[C@@H]4CC[C@H]3C[C@@H](OCc3c(-c5c(Cl)cccc5Cl)noc3C3CC3)C4)n2)ccc1C(=O)O] | 4-(2-((1R,3r,5S)-3-((5-cyclopropyl-3-(2,6-dichlorophenyl)isoxazol-4-yl)methoxy)-8-azabicyclo[3.2.1]octan-8-yl)thiazol-4-yl)-2-methylbenzoic acid | MS m/z (ESI): 610 [M + H]+ |
| C49 | 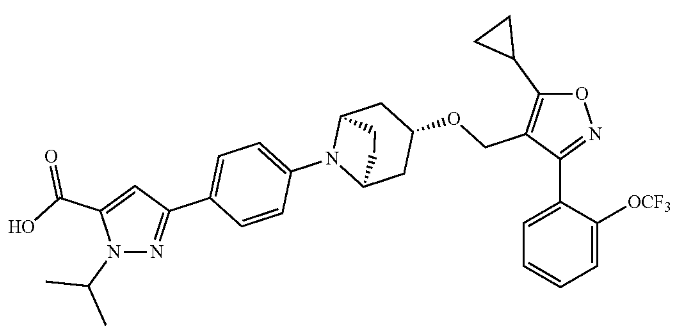 [SMILES: CC(C)n1nc(-c2ccc(N3[C@@H]4CC[C@H]3C[C@@H](OCc3c(-c5ccccc5OC(F)(F)F)noc3C3CC3)C4)cc2)cc1C(=O)O] | 3-(4-((1R,3r,5S)-3-((5-cyclopropyl-3-(2-(trifluoromethoxy)phenyl)isoxazol-4-yl)methoxy)-8-azabicyclo[3.2.1]octan-8-yl)phenyl)-1-isopropyl-1H-pyrazole-5-carboxylic acid | MS m/z (ESI): 637 [M + H]+ |

Biological Assay

Experimental Example 1. Bile Acid Receptor FXR Coactivator Binding Assay

1. Test Method

The Invitrogen•LanthaScreen™ TR-FRET Farnesoid X Receptor Coactivator Assay kit was employed to determine the activation effect of the compounds on FXR.

After the receptor was incubated with the test compound at various concentrations at room temperature, the fluorescent-labeled coactivator short peptides and terbium-labeled antibody were added, and the FRET signal was detected after the reaction was complete at room temperature. The group without the receptor protein was employed as a blank, the activation effect ($EC_{50}$) and maximum activation effect signal value (Emax) of the test compounds on FXR were calculated according to the four-parameter fitting equation:

$$y = E\min + (E\max - E\min)/(1+(x/EC_{50})^{(-\text{Hillslope})})$$

wherein y is the FRET binding signal, Emax and Emin respectively are the upper and lower asymptotic estimates of the fitted curve, x is the logarithmic concentration of the compound, and Hillslope is the slope of the curve.

In addition, taking chenodeoxycholic acid (i.e., CDCA) as a positive control, the relative activation effect of the compound tested in the present application was calculated according to the following equation:

$$\text{Relative activation effect (\%)} = (E\max/E\max') \times 100\%$$

wherein Emax represents the maximum activation effect value of the compound tested in the present application, and Emax' represents the maximum activation effect value of CDCA, both of them are calculated according to the equation as described above.

2. Test Results

TABLE 2

| Compound No. | $EC_{50}$ (μM) |
|---|---|
| CDCA | 4.43 ± 0.84 |
| C1 | 0.178 ± 0.021 |
| C2 | 0.012 ± 0.004 |
| C3 | 0.042 ± 0.007 |
| C4 | 0.010 ± 0.001 |
| C6 | 0.206 ± 0.018 |
| C35 | 0.013 ± 0.003 |
| C37 | 0.015 ± 0.001 |
| C44 | 0.022 ± 0.005 |
| C45 | 0.110 ± 0.021 |
| C46 | 0.002 ± 0.001 |
| C50 | 0.031 ± 0.008 |

$EC_{50}$ of the compounds tested in the present application on FXR

According to the data in Table 2, the compounds tested have lower $EC_{50}$ values (0.002-0.206 μM), compared with chenodeoxycholic acid (CDCA) ($EC_{50}$ value: 4.43 μM), indicating that the compounds of the present invention have a better activation effect on FXR.

TABLE 3

Relative activation effect of the compounds tested in the present application on FXR

| Compound No. | Relative activation effect |
|---|---|
| CDCA | 100% |
| C2 | 101% |
| C4 | 102% |
| C35 | 152% |
| C37 | 139% |
| C44 | 137% |
| C45 | 113% |
| C46 | 196% |
| C50 | 177% |

According to the data in Table the maximum activation effect values of the compounds tested in the present application are comparable or higher than that of chenodeoxycholic acid (CDCA), indicating that the compounds of the present invention have a good maximum activation effect on FXR.

Taken together, the $EC_{50}$ values and relative activation effect data in Tables 2 and 3 indicate that the compounds of the present invention have a good activation effect on FXR.

The remaining compounds of the present invention also have good $EC_{50}$ values and relative activation effects, that is, they have good activation activity and maximum activation effect on FXR.

Experimental Example 2. Luciferase Reporter Gene Assay

1. Test Method

Human embryonic kidney cells HEK293 were cultured in a DMEM medium containing 10% FBS. Plasmids were cotransfected to allow the cells to have over expression of FXR and human BSEP luciferase reporter genes. The transfected cells were digested, resuspended, counted, and plated in a multi-well plate. 10 μL of the test compound at various concentrations was added to the multi-well plate to result in final concentrations of 64 μM, 16 μM, 4 μM, 1 μM, 0.25 μM, 0.0625 μM, 0.0156 μM, 0.0039 μM, 0.000975 μM, 0.000244 μM, 0 μM, and the final concentration of DMSO was 0.5%. After the test compound was incubated with the cells for 18 hours, the Brigh-Glo™ detection reagent was added, and the chemical light unit value (RLU) was detected by a multifunctional automatic microplate reader. Taking the signal value of the blank well (without the test compound) as 100%, the relative signal percentage (%) at each concentration of the test compound was calculated. The SigmaPlot 10 software was employed to fit the $EC_{50}$ and the maximum activation effect Emax (relative signal percentage) of the test compounds using a four-parameter model.

2. Test Results

The test results are shown in Table 4 below.

TABLE 4

| Compound No. | $EC_{50}$ (μM) | Emax |
|---|---|---|
| C2 | 0.02 ± 0.01 | 248% |
| C4 | 0.04 ± 0.01 | 255% |
| C35 | 0.091 ± 0.038 | 378% |
| C37 | 0.006 ± 0.002 | 411% |
| C41 | 0.058 ± 0.023 | 252% |

TABLE 4-continued

| Compound No. | EC$_{50}$ (μM) | Emax |
|---|---|---|
| C42 | 0.033 ± 0.018 | 320% |
| C43 | 0.037 ± 0.019 | 343% |
| C44 | 0.021 ± 0.006 | 322% |
| C46 | 0.014 ± 0.005 | 301% |
| C47 | 0.019 ± 0.007 | 370% |
| C48 | 0.039 ± 0.017 | 382% |

According to the data in Table 4, in the in vitro cell assay, the compounds tested in the present application have EC$_{50}$ values between 0.006 μM and 0.091 μM and Emax values greater than 200%. It is shown that the compounds of the present invention have good FXR activation activity in the in vitro cell assay.

The remaining compounds of the present invention also have good EC$_{50}$ and Emax values, that is, they have good FXR activation activity in the in vitro cell assay.

Experimental Example 3: Study on Pharmacokinetics (PK) and Liver Tissue Distribution in Rats The test compound was administered to male SD rats by intravenous (IV) and by gavage (PO), and the pharmacokinetics and liver tissue distribution characteristics of the test compound were evaluated. The doses of the IV and PO administration were respectively 1 mg/kg and 5 mg/kg. The vehicle for IV was 5% DMSO:5% Solutol:90% physiological saline, and the vehicle for PO was 0.5% MC. Blood and liver were collected at various time points after the IV and PO administration. The blood was treated with EDTA. K$_2$ for anticoagulation, and was centrifuged to obtain a plasma sample; the liver was homogenized and stored at −80° C. The plasma and liver samples were analyzed by LC-MS/MS after being subjected to protein precipitation.

By employing the WinNonlin 6.3 software, the pharmacokinetic parameters were calculated according to a non-compartment model. The results are shown in Tables 5 and 6.

TABLE 5

Pharmacokinetic parameters of the test compound administered by IV in rats

| Compound No. | Administration route | Dosage mg/kg | AUC$_{last}$ h*ng/mL | C$_{max}$ ng/mL |
|---|---|---|---|---|
| C2 | IV | 1 | 2409 ± 108 | 4343 ± 172 |

According to the data in Table 5, after IV administration of compound C2 of the present invention at a dose of 1 mg/kg, the AUC$_{last}$ in rats is 2409±108 h*ng/mL and the C$_{max}$ is 4343±172 ng/mL, indicating that compound C2 of the present invention administered by IV in rats has good drug exposure.

TABLE 6

Pharmacokinetic parameters of the test compound administered by PO in rats

| Compound No. | Administration route | Dosage | AUC$_{last}$ | C$_{max}$ |
|---|---|---|---|---|
| C2 | PO | 5 mg/kg | 1177 ± 304 h*ng/mL (blood) | 252 ± 30 ng/mL (blood) |

TABLE 6-continued

Pharmacokinetic parameters of the test compound administered by PO in rats

| Compound No. | Administration route | Dosage | AUC$_{last}$ | C$_{max}$ |
|---|---|---|---|---|
| C2 | PO | 5 mg/kg | 14941 ± 4276 h*ng/g (liver) | 3367 ± 830 ng/g (liver) |

According to the data in Table 6, after PO administration of compound C2 of the present invention at a dose of 5 mg/kg, the AUC$_{last}$ in the blood and liver of the rats are respectively 1177±304 h*ng/mL and 14941±4276 h*ng/g, and the C$_{max}$ in the blood and liver of the rats are respectively 252±30 ng/mL and 3367±830 ng/g, indicating that compound C2 of the present invention administered by PO in rats has certain drug exposure and a significant liver enrichment effect.

Taken together, the data in Tables 5 and 6 indicate the compound of Example 2 of the present invention administered by IV in rats has good plasma drug exposure, and the compound administered by PO in rats has certain drug exposure and significant liver enrichment effect.

The remaining compounds of the present invention also have good AUC$_{last}$ and C$_{max}$ values, and thus have good pharmacokinetic properties in rats.

When applied as a drug for a disease mediated by FXR, the compound of the present invention exhibits a good effect in terms of drug safety, and shows good drug activity and in vivo metabolic advantages is respect of pharmacodynamics or pharmacokinetics in animals or in vitro.

Experimental Example 4: Liver Microsomal Stability Test

Test Method

The test compound (50 μL) was mixed with the liver microsome (100 μL) of each species, after pre-incubation at 37° C. for 5 minutes, NADPH (50 μL) was added, and the incubation was performed for 0, 30, and 60 minutes. The incubation concentrations of the test compound, NADPH, and liver microsomal enzyme were 1 μM, 1 mM, and 0.5 mg/mL, respectively. Ice-cold acetonitrile (200 μL) was added to stop the reaction, and an appropriate volume of the internal standard was then added. After the vortex and centrifugation process, the supernatant was obtained and detected.

Detection Method

LC-MS/MS, wherein the mass spectrometer was API 5500, and the liquid chromatograph was Shimadzu LC-30AD system. The chromatographic column was Hypersil GOLD C18, 1.9 μm particle size, 50×2.1 mm; mobile phase A was water+0.1% formic acid, phase B was acetonitrile; flow rate was 0.55 mL/min, and column temperature was 40° C. The ion source was an ESI source positive ion mode, and the scanning mode is multiple reaction monitoring (MRM).

By determining the concentrations of the samples at different incubation time, the rate constant was obtained by plotting "Ln (amount of the remained drug %)" versus "incubation time". The half-life and liver clearance rate of the drug were then calculated, and were used to evaluate the metabolic stability of the drug in liver microsome.

Test Results

TABLE 7

Liver microsomal stability test

Liver microsomal stability of compound C46

| Species | $T_{1/2}$ (min) | $CL_{int\ (liver)}$ ml/min/kg |
|---|---|---|
| rat | 963 | 0.96 |
| mouse | 150 | 15.3 |
| dog | 259 | 8.03 |

Conclusion: according to the experimental data in Table 7, compound C46 of the present invention has a good clearance rate in liver microsome, and the clearance rate in human liver microsome is 14.9 ml/min/kg, indicating good clearance.

In addition to those embodiments described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A compound of general formula (I) or a stereoisomer, tautomer, polymorph, solvate, pharmaceutically acceptable salt, ester, or N-oxide thereof,

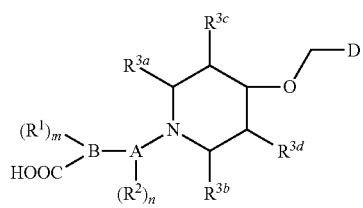

(I)

wherein:

A is thiazolylene;

B is selected from the group consisting of $C_{6-10}$ aryl and 5- to 10-membered heteroaryl containing 1, 2, 3 or 4 heteroatoms independently selected from the group consisting of N, O and S;

D is

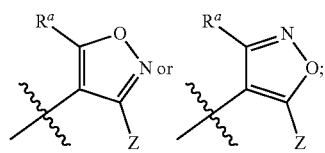

Z is

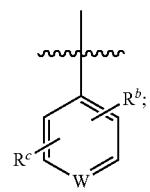

W is selected from the group consisting of N and $CR^d$;

$R^a$ is selected from the group consisting of hydrogen, $C_{1-6}$ alkyl, $C_{2-6}$ alkenyl, $C_{2-6}$ alkynyl, $C_{3-8}$ cycloalkyl, 3- to 14-membered heterocyclyl, $C_{1-6}$ alkyl-O—, $C_{1-6}$ haloalkyl, $C_{3-8}$ halocycloalkyl and $C_{1-6}$ haloalkyl-O—;

$R^b$, $R^c$ and $R^d$ are each independently selected from the group consisting of hydrogen, halogen, hydroxyl, cyano, —$NH_2$, nitro, $C_{1-6}$ alkyl, $C_{1-6}$ haloalkyl, $C_{1-6}$ alkyl-O—, $C_{1-6}$ haloalkyl-O—, $C_{3-8}$ cycloalkyl, $C_{3-8}$ halocycloalkyl, $C_{3-8}$ cycloalkyl-O— and $C_{3-8}$ halocycloalkyl-O—;

$R^1$ and $R^2$ are each independently selected from the group consisting of hydrogen, halogen, cyano, hydroxyl, —$NH_2$, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl, $C_{3-8}$ halocycloalkyl, $C_{1-6}$ alkyl-NH— and $(C_{1-6}$ alkyl$)_2$-N—;

$R^{3a}$, $R^{3b}$, $R^{3c}$ and $R^{3d}$ are each independently selected from the group consisting of hydrogen, halogen, cyano, hydroxyl, —$NH_2$, oxo, $C_{1-6}$ alkyl, $C_{1-6}$ haloalkyl, $C_{1-6}$ hydroxyalkyl, $C_{1-6}$ alkyl-O—, $C_{1-6}$ haloalkyl-O—, $C_{3-8}$ cycloalkyl and $C_{3-8}$ halocycloalkyl; alternatively, any two of $R^{3a}$, $R^{3b}$, $R^{3c}$ and $R^{3d}$ together form $C_{1-6}$ alkylene;

m and n are each independently 0, 1, 2, 3 or 4; and the above alkyl, alkylene, alkenyl, alkynyl, cycloalkyl, heterocyclyl, aryl and heteroaryl are each optionally substituted with 1, 2, or 3 substituents independently selected from the group consisting of halogen, hydroxyl, oxo, cyano, —$NH_2$, nitro, $C_{1-6}$ alkyl, $C_{1-6}$ haloalkyl, $C_{1-6}$ alkyl-O—, $C_{1-6}$ haloalkyl-O—, $C_{3-6}$ cycloalkyl, $C_{3-6}$ halocycloalkyl, $C_{1-6}$ alkyl-NH—, $(C_{1-6}$ alkyl$)_2$-N—, $C_{1-6}$ hydroxyalkyl, cyano-$C_{1-6}$ alkyl, 3- to 14-membered heterocyclyl, $C_{6-14}$ aryl and 5- to 14-membered heteroaryl.

2. The compound according to claim 1, or a stereoisomer, tautomer, polymorph, solvate, pharmaceutically acceptable salt, ester, or N-oxide thereof, wherein A is selected from the group consisting of

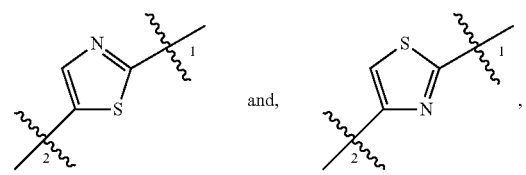 [SMILES: *c1cnc(*)s1 ; *c1csc(*)n1]

attached to the ring nitrogen atom in general formula (I) at either of the two positions labeled 1 or 2, and attached to group B at the other position.

3. The compound according to claim 1, or a stereoisomer, tautomer, polymorph, solvate, pharmaceutically acceptable salt, ester, or N-oxide thereof, wherein B is selected from the group consisting of phenyl and 5- to 6-membered heteroaryl containing 1, 2, 3 or 4 heteroatoms independently selected from the group consisting of N, O and S.

4. The compound according to claim 1, or a stereoisomer, tautomer, polymorph, solvate, pharmaceutically acceptable salt, ester, or N-oxide thereof, wherein the group

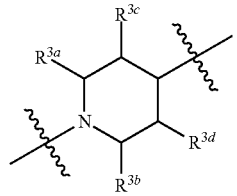

in general formula (I) is

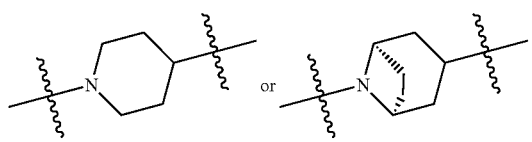

5. The compound according to claim 1, or a stereoisomer, tautomer, polymorph, solvate, pharmaceutically acceptable salt, ester, or N-oxide thereof, wherein the compound is a compound of general formula (Ia):

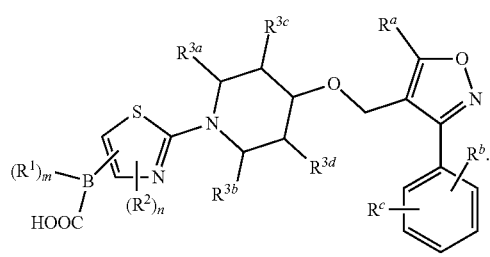

(Ia)

6. The compound according to claim 1, or a stereoisomer, tautomer, polymorph, solvate, pharmaceutically acceptable salt, ester, or N-oxide thereof, wherein the compound is selected from the group consisting of:

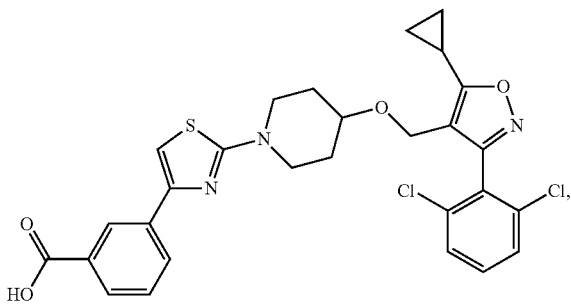

C1

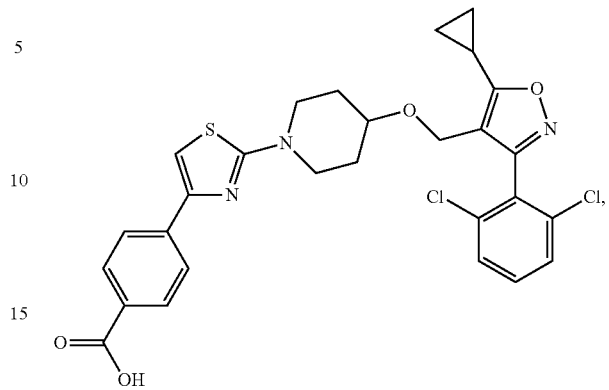

C2

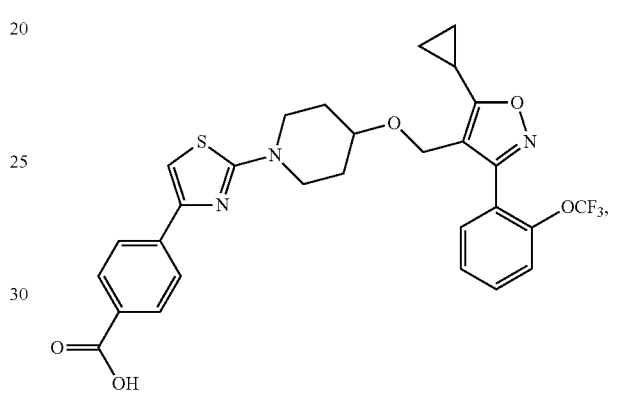

C7

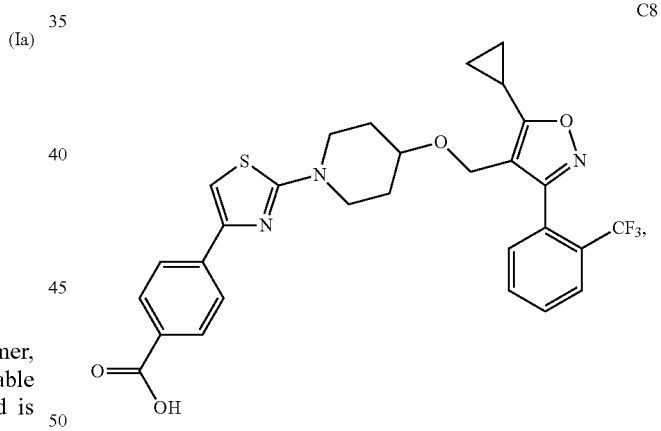

C8

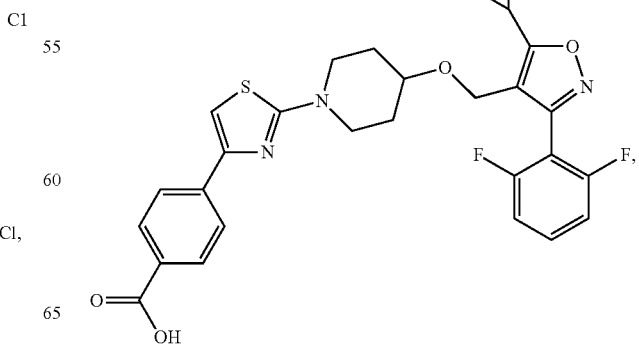

C9

101
-continued
C10
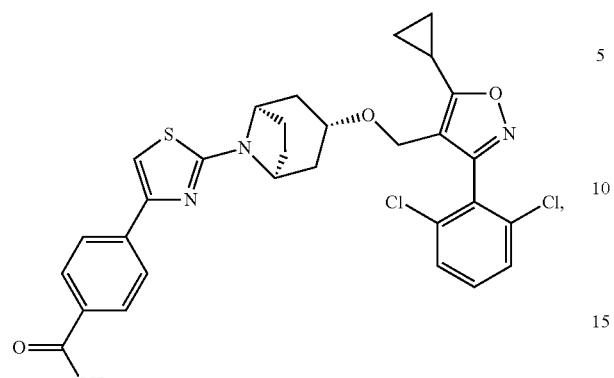
C11
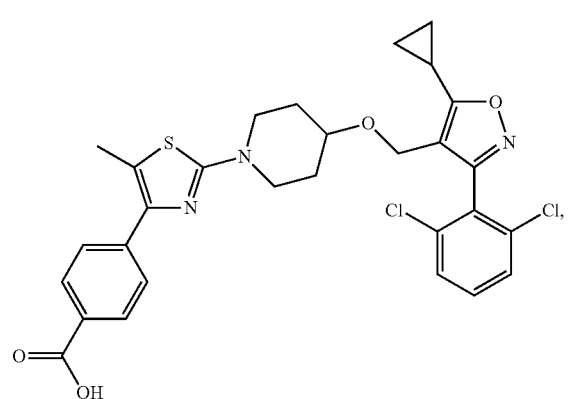
C12
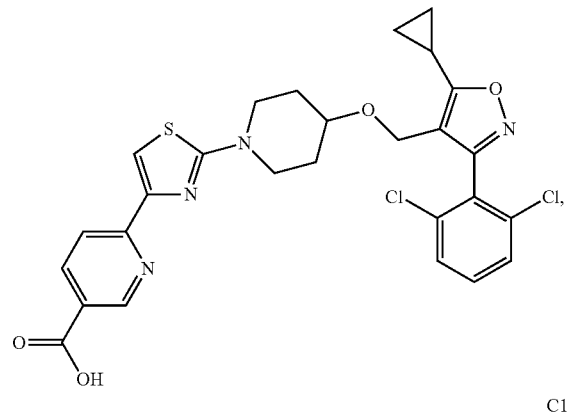
C13
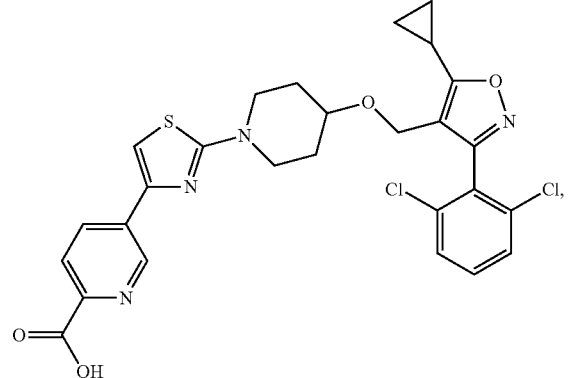
102
-continued
C14
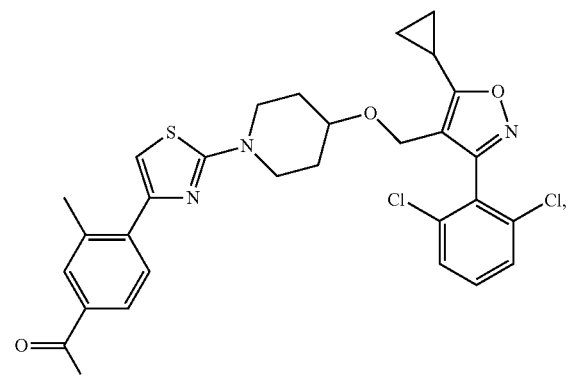
C15
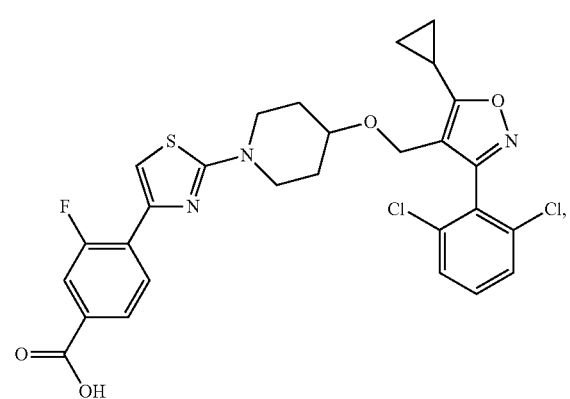
C16
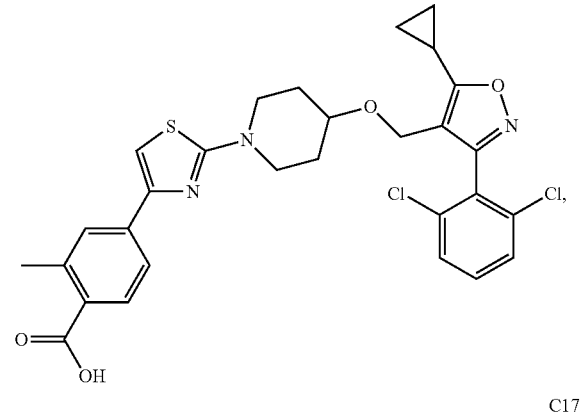
C17

103
-continued
C28
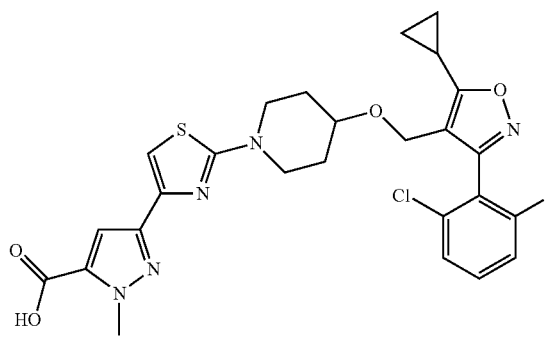
C29
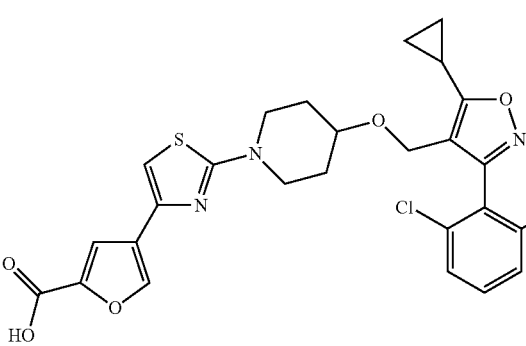
C30
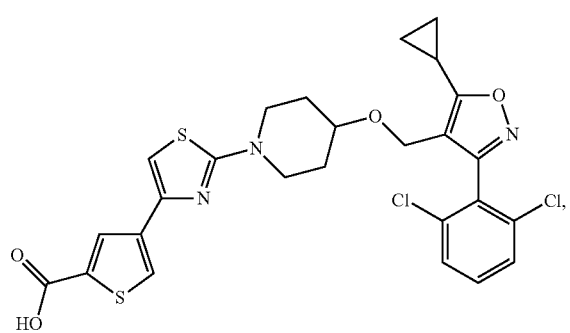
C31
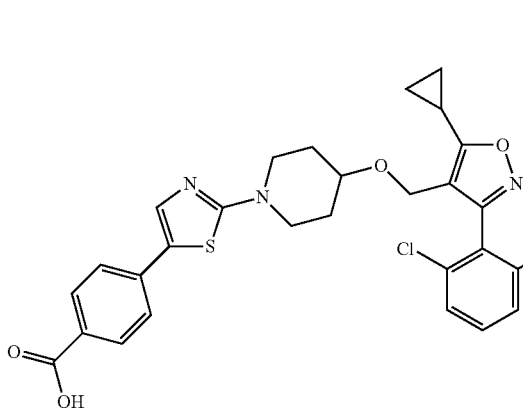
104
-continued
C32
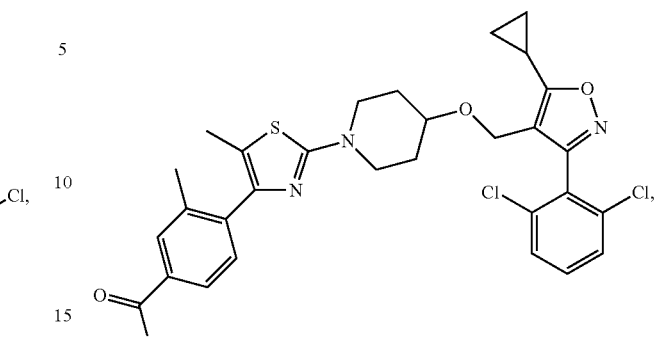
C35
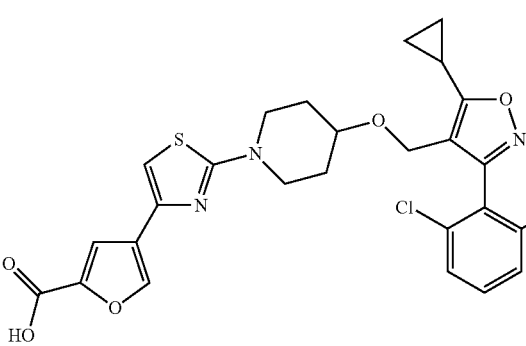
C36
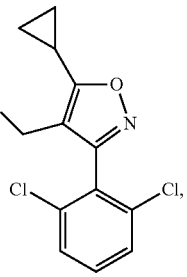
C37
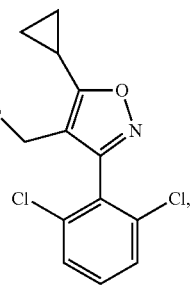

-continued
C38
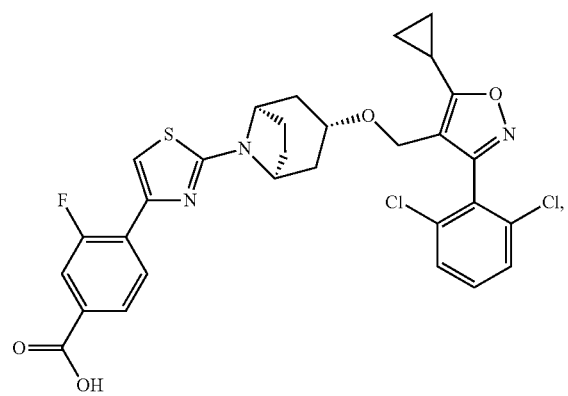
C39
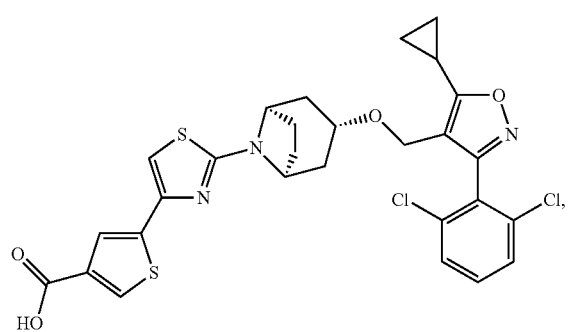
C40
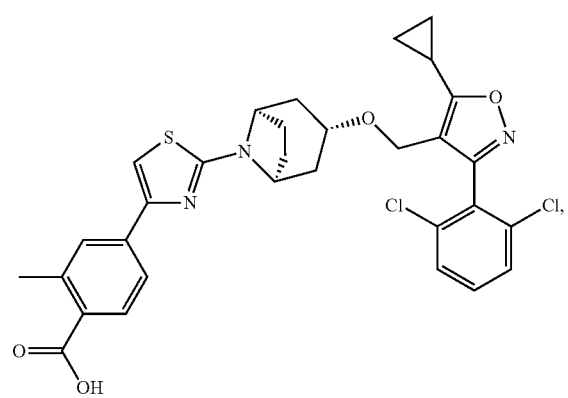
C41
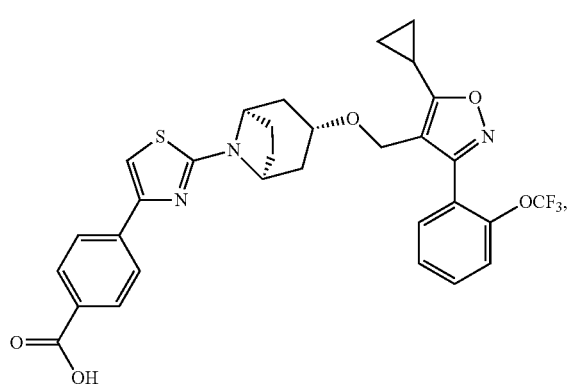
-continued
C42
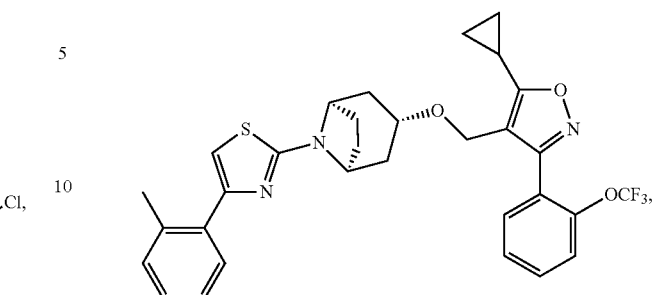
C43
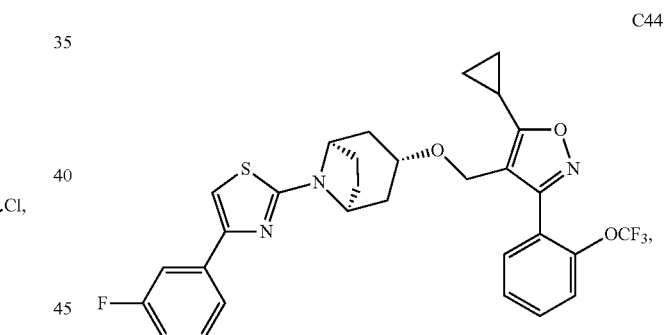
C44
C45
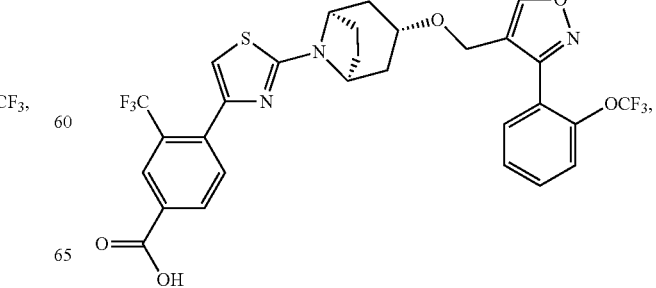

-continued

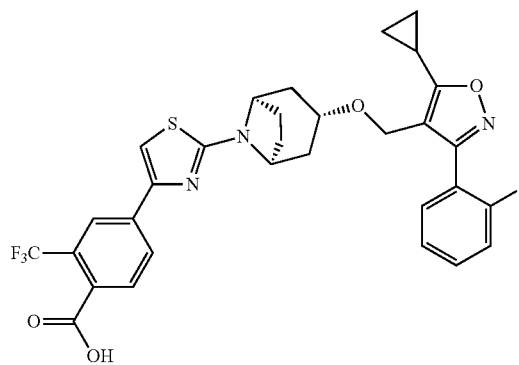
C46

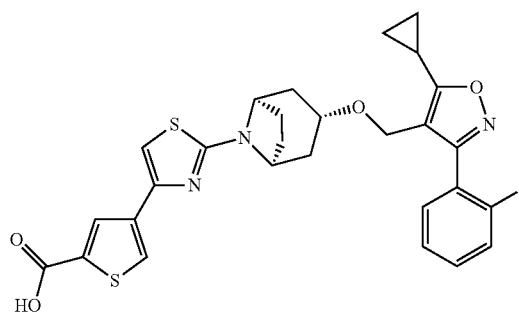
C47

C48

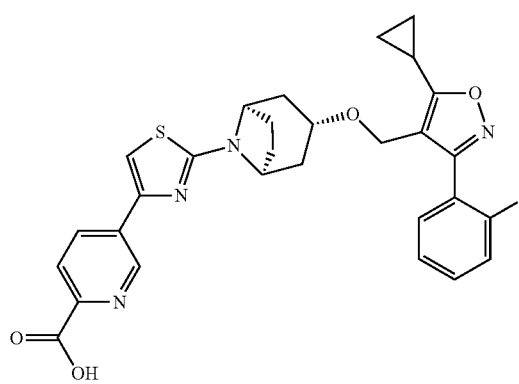
and

C50

7. A pharmaceutical composition comprising at least one compound according to claim 1, or a stereoisomer, tautomer, polymorph, solvate, pharmaceutically acceptable salt, ester, or N-oxide thereof, and one or more pharmaceutically acceptable carriers.

8. The pharmaceutical composition according to claim 7, which is in a form selected from the group consisting of tablet, capsule, lozenge, hard candy, powder, spray, cream, salve, suppository, gel, paste, lotion, ointment, aqueous suspension, injectable solution, elixir, and syrup.

9. A kit, the kit comprising:
a) a first container containing at least one compound according to claim 1, or a stereoisomer, tautomer, polymorph, solvate, pharmaceutically acceptable salt, ester, or N-oxide thereof, as a first therapeutic agent;
b) an optional second container containing at least one additional therapeutic agent as a second therapeutic agent, or a pharmaceutical composition comprising the additional therapeutic agent as a second pharmaceutical composition; and
c) an optional package insert.

10. A method for preparing the compound of general formula (I) according to claim 1, wherein the method comprises the following steps:

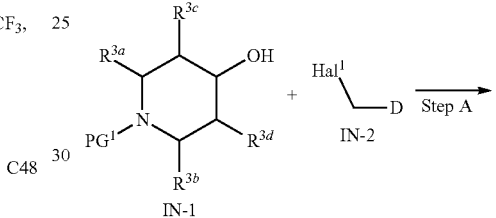

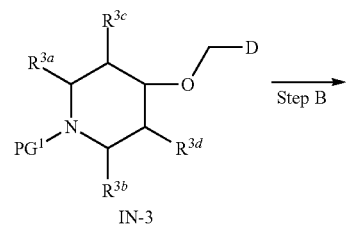

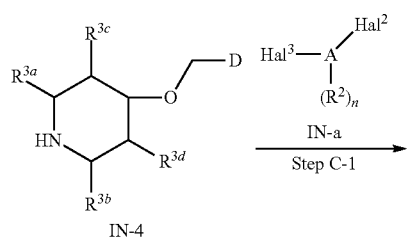

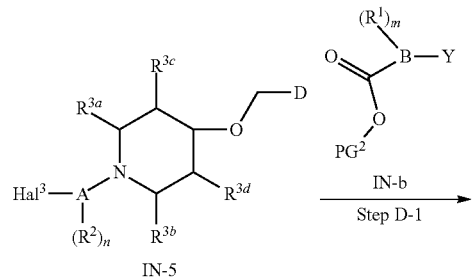

-continued

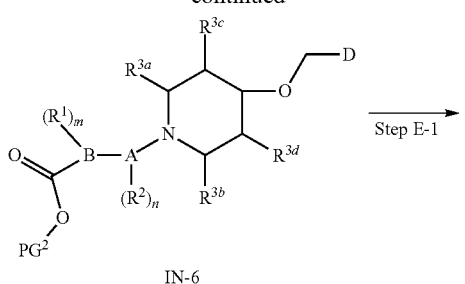

IN-6

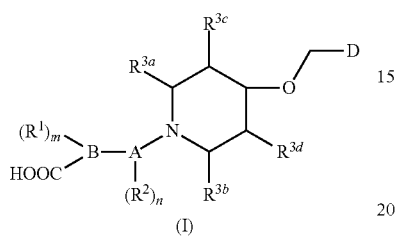

(I)

wherein:

Hal¹, Hal² and Hal³, each independently, are same or different halogens;

PG¹ is an amino protecting group;

PG² is a carboxy protecting group;

Y is a boronic acid or borate group;

the remaining groups are as defined in claim 1;

the reaction conditions for each step are as follows:

step A: reacting compound IN-1 with compound IN-2 to obtain compound IN-3;

step B: removing the PG¹ group in compound IN-3 to obtain compound IN-4;

step C-1: reacting compound IN-4 with compound IN-a to obtain compound IN-5;

step D-1: reacting compound IN-5 with compound IN-b to obtain compound IN-6; and step E-1: removing the PG² group in compound IN-6 to obtain the compound of general formula (I);

alternatively, the method comprises the following steps:

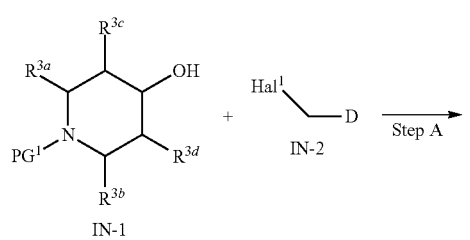

IN-1

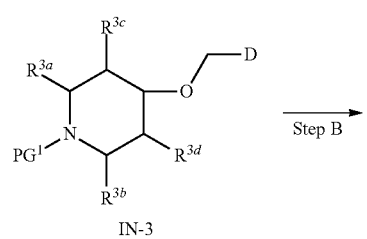

IN-3

-continued

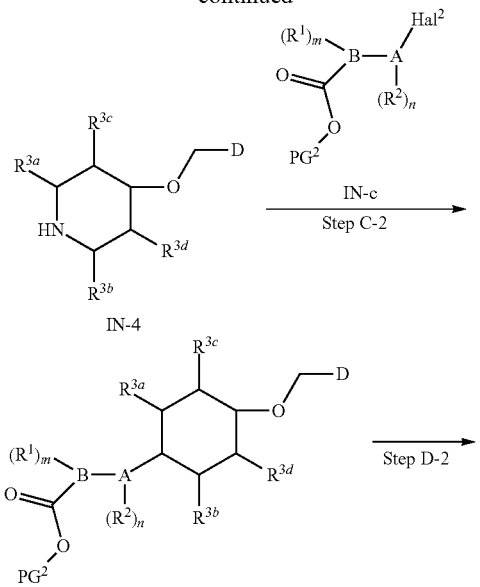

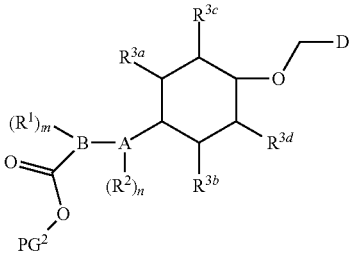

IN-6

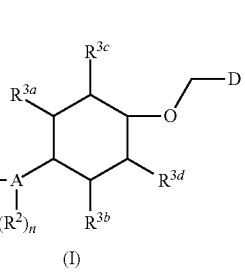

(I)

wherein each of the groups is as defined above;

the reaction conditions for each step are as follows:

step A: reacting compound IN-1 with compound IN-2 to obtain compound IN-3;

step B: removing the PG¹ group in compound IN-3 to obtain compound IN-4;

step C-2: reacting compound IN-4 with compound IN-c to obtain compound IN-6; and step D-2: removing the PG² group in compound IN-6 to obtain the compound of general formula (I).

11. A pharmaceutical composition comprising at least one compound according to claim 5 or a stereoisomer, tautomer, polymorph, solvate, pharmaceutically acceptable salt, ester, or N-oxide thereof, and one or more pharmaceutically acceptable carriers.

12. A pharmaceutical composition comprising at least one compound according to claim 6 or a stereoisomer, tautomer, polymorph, solvate, pharmaceutically acceptable salt, ester, or N-oxide thereof, and one or more pharmaceutically acceptable carriers.

13. The pharmaceutical composition according to claim 11, which is in a form selected from the group consisting of tablet, capsule, lozenge, hard candy, powder, spray, cream, salve, suppository, gel, paste, lotion, ointment, aqueous suspension, injectable solution, elixir, and syrup.

14. The pharmaceutical composition according to claim 12, which is in a form selected from the group consisting of tablet, capsule, lozenge, hard candy, powder, spray, cream, salve, suppository, gel, paste, lotion, ointment, aqueous suspension, injectable solution, elixir, and syrup.

15. A kit comprising:
a) a first container containing at least one compound according to claim 5 or a stereoisomer, tautomer, polymorph, solvate, pharmaceutically acceptable salt, ester, or N-oxide thereof, as a first therapeutic agent;
b) an optional second container containing at least one additional therapeutic agent as a second therapeutic agent, or a pharmaceutical composition comprising the additional therapeutic agent as a second pharmaceutical composition; and
c) an optional package insert.

16. A kit comprising:
a) a first container containing at least one compound according to claim 6 or a stereoisomer, tautomer, polymorph, solvate, pharmaceutically acceptable salt, ester, or N-oxide thereof, as a first therapeutic agent;
b) an optional second container containing at least one additional therapeutic agent as a second therapeutic agent, or a pharmaceutical composition comprising the additional therapeutic agent as a second pharmaceutical composition; and
c) an optional package insert.

\* \* \* \* \*